(12) United States Patent
Dai et al.

(10) Patent No.: US 8,123,357 B2
(45) Date of Patent: *Feb. 28, 2012

(54) WAVEFRONT PROPAGATION FROM ONE PLANE TO ANOTHER

(75) Inventors: Guangming Dai, Fremont, CA (US); Charles E. Campbell, Berkeley, CA (US); Li Chen, San Jose, CA (US); Huawei Zhao, Irvine, CA (US); Dimitri Chernyak, Sunnyvale, CA (US)

(73) Assignee: Amo Manufacturing USA, LLC., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/023,871

(22) Filed: Feb. 9, 2011

(65) Prior Publication Data

US 2011/0134391 A1 Jun. 9, 2011

Related U.S. Application Data

(60) Continuation of application No. 12/421,246, filed on Apr. 9, 2009, now Pat. No. 7,931,374, which is a division of application No. 11/736,353, filed on Apr. 17, 2007, now Pat. No. 7,547,102, and a continuation-in-part of application No. 11/032,469, filed on Jan. 7, 2005, now Pat. No. 7,296,893.

(60) Provisional application No. 60/826,636, filed on Sep. 22, 2006, provisional application No. 60/550,514, filed on Mar. 3, 2004.

(51) Int. Cl.
*A61B 3/00* (2006.01)
*A61B 3/10* (2006.01)

(52) U.S. Cl. ............. 351/246; 351/205; 351/208; 606/4
(58) Field of Classification Search ................. 351/205, 351/246, 247

See application file for complete search history.

(56) References Cited

U.S. PATENT DOCUMENTS

| | | | |
|---|---|---|---|
| 4,437,733 | A | 3/1984 | Takahashi et al. |
| 5,379,110 | A | 1/1995 | Matsui et al. |
| 6,550,917 | B1 | 4/2003 | Neal et al. |
| 6,786,603 | B2 | 9/2004 | Altmann |
| 6,817,714 | B2 | 11/2004 | Altmann |

(Continued)

FOREIGN PATENT DOCUMENTS

WO WO 01/85016 A 11/2001

(Continued)

OTHER PUBLICATIONS

Klein, Stanley A., "Optimal Corneal Ablation for Eyes with Arbitrary Hartmann-Shack Aberrations," J. Opt. Soc. Am. A, vol. 15 (Sep. 1998), No. 9, pp. 2580-2588.

(Continued)

*Primary Examiner* — Jordan Schwartz

(57) ABSTRACT

The present invention provides methods, systems and software for scaling optical aberration measurements of optical systems. In one embodiment, the present invention provides a method of reconstructing optical tissues of an eye. The method comprises transmitting an image through the optical tissues of the eye. Aberration data from the transmitted image is measured across the optical tissues of the eye at a first plane. A conversion algorithm is applied to the data, converting it to corrective optical power data that can be used as a basis for constructing a treatment for the eye at a second plane.

7 Claims, 20 Drawing Sheets

U.S. PATENT DOCUMENTS

| | | |
|---|---|---|
| 7,281,797 B2 | 10/2007 | Yamaguchi et al. |
| 7,296,893 B2 | 11/2007 | Dai |
| 7,547,102 B2 | 6/2009 | Dai |
| 7,726,813 B2 | 6/2010 | Dai |
| 2003/0163122 A1 | 8/2003 | Sumiya |
| 2003/0189690 A1 | 10/2003 | Mihashi et al. |
| 2004/0057010 A1 | 3/2004 | Altmann |
| 2004/0260275 A1 | 12/2004 | Liang et al. |
| 2007/0195265 A1 | 8/2007 | Dreher et al. |
| 2007/0211214 A1 | 9/2007 | Dai |
| 2007/0285617 A1 | 12/2007 | Mills et al. |
| 2008/0198331 A1 | 8/2008 | Azar et al. |
| 2009/0168019 A1* | 7/2009 | Tuan .................. 351/206 |
| 2009/0231546 A1 | 9/2009 | Dai |
| 2010/0179793 A1* | 7/2010 | Chernyak et al. .......... 703/2 |
| 2010/0234833 A1 | 9/2010 | Dai |

FOREIGN PATENT DOCUMENTS

| | | |
|---|---|---|
| WO | WO 2004/028356 A | 4/2004 |

OTHER PUBLICATIONS

Liang et al., "Objective Measurement of Wave Abberations of the Human Eye With the Use of a Hartmann-Shack wave-front sensor," Optical Society of America, A. Jul. 1994, 11:7, pp. 1949-1957.

* cited by examiner

WAVEFRONT PROPAGATION FROM ONE PLANE TO ANOTHER

CROSS-REFERENCE TO RELATED APPLICATIONS

This application is a continuation of U.S. patent application Ser. No. 12/421,246, filed Apr. 9, 2009, which is a divisional of U.S. patent application Ser. No. 11/736,353, filed Apr. 17, 2007, which also claims the benefit of U.S. patent application Ser. No. 60/826,636 filed Sep. 22, 2006, and which is a continuation-in-part of U.S. patent application Ser. No. 11/032,469 filed Jan. 7, 2005, which claims the benefit of U.S. Patent No. 60/550,514 filed Mar. 3, 2004. The full disclosure of each of these filings is incorporated herein by reference.

BACKGROUND OF THE INVENTION

The present invention generally relates to scaling optical aberration measurements of optical systems. More particularly, the invention relates to improved methods and systems for processing optical power measurements taken at a first plane and converting those power measurements to corrective optical power measurements that can be used at a second plane. The present invention may be useful in any of a variety of ocular treatment modalities, including ablative laser eye surgery, contact lenses, spectacles, intraocular lenses, and the like.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, and the like.

Known corneal correction treatment methods have generally been successful in correcting standard vision errors, such as myopia, hyperopia, astigmatism, and the like. However, as with all successes, still further improvements would be desirable. Toward that end, wavefront measurement systems are now available to accurately measure the refractive characteristics of a particular patient's eye. One exemplary wavefront technology system is the VISX WaveScan® System, which uses a Hartmann-Shack wavefront lenslet array that can quantify aberrations throughout the entire optical system of the patient's eye, including first- and second-order sphero-cylindrical errors, coma, and third and fourth-order aberrations related to coma, astigmatism, and spherical aberrations.

Wavefront-driven vision correction has become a top choice for higher quality vision, after a series of significant development in the research of the wavefront technology (Liang, J. et al., *J. Opt. Soc. Am. A* 11:1949-1957 (1994); Liang, J. et al., *J. Opt. Soc. Am. A* 14:2873-2883 (1997); Liang, J. et al., *J. Opt. Soc. Am. A* 14:2884-2892 (1997); Roorda, A. et al., *Nature* 397:520-522 (1999)). Although the ocular aberrations can be accurately captured, several factors need to be considered when they are corrected using, say, the refractive surgical technique. The first of such factors is the relative geometric transformation between the ocular map when the eye is examined and the ocular map when the eye is ready for laser ablation. Not only can the eye have x- and y-shift between the two maps, but it can also have possible cyclo-rotations (Walsh, G. *Ophthal. Physiol. Opt.* 8:178-182 (1988); Wilson, M. A. et al., *Optom. Vis. Sci.* 69:129-136 (1992); Donnenfeld, E. *J. Refract. Surg.* 20:593-596 (2004) Chernyak, D. A. *J. Cataract. Refract. Surg.* 30:633-638 (2004)). Such problems have been studied by Guirao et al. (Guirao, A. et al., *J. Opt. Soc. Am. A* 18:1003-1015 (2001)). Another problem deals with the pupil size change (Goldberg, K. A. et al., *J. Opt. Soc. Am. A* 18:2146-2152 (2001); Schwiegerling, J. *J. Opt. Soc. Am. A* 19:1937-1945 (2002); Campbell, C. E. *J. Opt. Soc. Am. A* 20:209-217 (2003)) using Zernike representation (Noll, R. J. *J. Opt. Soc. Am.* 66:203-211 (1976); Born, M. et al., Principles of Optics, 7th ed. (Cambridge University Press, 1999)). Because of the analytical nature and the popularity of Zernike polynomials, this problem has inspired an active research recently (Dai, G.-m. *J. Opt. Soc. Am. A* 23:539-543 (2006); Shu, H. et al., *J. Opt. Soc. Am. A* 23:1960-1968 (2006); Janssen, A. J. E. M. et al., *J. Microlith., Microfab., Microsyst.* 5:030501 (2006); Bará, S. et al., *J. Opt. Soc. Am. A* 23:2061-2066 (2006); Lundström, L. et al., *J. Opt. Soc. Am. A* (accepted)).

Wavefront measurement of the eye may be used to create a high order aberration map or wavefront elevation map that permits assessment of aberrations throughout the optical pathway of the eye, e.g., both internal aberrations and aberrations on the corneal surface. The aberration map may then be used to compute a custom ablation pattern for allowing a surgical laser system to correct the complex aberrations in and on the patient's eye. Known methods for calculation of a customized ablation pattern using wavefront sensor data generally involves mathematically modeling an optical surface of the eye using expansion series techniques. More specifically, Zernike polynomials have been employed to model the optical surface, as proposed by Liang et al., in *Objective Measurement of Wave Aberrations of the Human Eye with the Use of a Hartmann-Shack Wave front Sensor*, Journal Optical Society of America, July 1994, vol. 11, No. 7, pp. 1949-1957, the entire contents of which is hereby incorporated by reference. Coefficients of the Zernike polynomials are derived through known fitting techniques, and the refractive correction procedure is then determined using the shape of the optical surface of the eye, as indicated by the mathematical series expansion model.

There is yet another problem that remains unaddressed. Optical measurements such as wavefront measurements are often taken at a measurement plane, whereas optical treatments may be needed at a treatment plane that is different from the measurement plane. Thus, power adjustments are often used when devising optical treatments for patients. For example, power adjustments can be used by optometrists when prescribing spectacles for patients. Typically, refractive measurements are made by an optometer at a measurement plane some distance anterior to the eye, and this distance may not coincide with the spectacle plane. Thus, the measured power corresponding to the measurement plane may need to be converted to a corrective power corresponding to the spectacle or treatment plane. Similarly, when wavefront measurements are obtained with wavefront devices, in many cases the measured map is conjugated to the pupil plane, which is not the same as the corneal plane or spectacle plane. To enhance the effectiveness of a refractive surgical procedure, vertex correction may be needed to adjust the power of the measured maps. Yet there remains a lack of efficient methods and systems for such power conversions. In other words, when the ocular aberrations are captured, they are often on the exit pupil plane. However, when the correction is applied, it is often on a different plane. For example, for refractive surgery, it is on the corneal plane. For contact lens, it is on the anterior surface of the contact lens. For intraocular lens, it is on the lens plane. And for spectacles, it is on the spectacle plane. Traditionally, for low order spherocylindrical error, a vertex correction formula can be applied (Harris, W. F. *Optom. Vis. Sci.* 73:606-612 (1996); Thibos, L. N. *S. Afr. Optom.* 62:111-113 (2003)), for example, to archive the power correction for the so-called conventional treatment for refractive surgery. The same formula can be applied to the power calculation for vision correction using the contact lens, intraocular lens, and spectacles. However such formulas may not be useful in some cases, for example where there are high order ocular aberrations to be corrected. Hence, new formulas are needed to represent the ocular aberrations when they are propagated to a new plane.

Therefore, in light of above, it would be desirable to provide improved methods and systems for processing optical data taken at a measurement plane and converting that optical data to corrective optical data that can be used at a treatment plane.

BRIEF SUMMARY OF THE INVENTION

The present invention provides methods and systems for processing optical power measurements taken at a first plane and converting those power measurements to corrective optical power measurements that can be used at a second plane.

In wavefront-driven vision correction, although ocular aberrations are often measured on the exit pupil plane, the correction is applied on a different surface. Thus there is a need for new systems and methods that account for the changes occurring in the propagated wavefront between two surfaces in vision correction. Advantageously, embodiments of the present invention provide techniques, based on geometrical optics and Zernike polynomials for example, to characterize wavefront propagation from one plane to another. In some embodiments, properties such as the boundary and the magnitude of the wavefront can change after the propagation. The propagation of the wavefront can be nonlinear. Taylor monomials can be effectively used to realize the propagation. Approaches used to identify propagation of low order aberrations can be verified with a classical vertex correction formula. Approaches used to identify propagation of high order aberrations can be verified with Zemax®. These techniques can be used with the propagation of common optical aberrations, for example. Advantageously, the techniques described herein provide improved solutions for wavefront driven vision correction by refractive surgery, contact lens, intraocular lens, and spectacles.

Embodiments encompass techniques for treating an ocular wavefront when it is propagated from one plane or surface to another. Zernike polynomials can be used to represent the ocular wavefront; they are orthonormal over circular pupils (Born, M. et al., Principles of Optics, 7th ed. (Cambridge University Press, 1999)). Taylor monomials can be used for the calculation of the wavefront slopes (Riera, P. R. et al., *Proc. SPIE* 4769, R. C. Juergens, ed., 130-144 (2002); Dai, G.-m. *J. Opt. Soc. Am. A* 23:1657-1666 (2006); Dai, G.-m. *J. Opt. Soc. Am. A* 23:2970-2971 (2006)). In some embodiments, Taylor monomials can be used for wavefront propagation. Before and after the propagation, Zernike polynomials can be converted to and from Taylor monomials using available conversion formulas (Dai, G.-m. *J. Opt. Soc. Am. A* 23:1657-1666 (2006)). Some embodiments encompass the use of an ordering convention for Zernike polynomials such as the ANSI standard (American National Standard Institute, *Methods for reporting optical aberrations of eyes*, ANSI Z80.28-2004 (Optical Laboratories Association, 2004), Annex B, pp. 1928). It has been discovered that in some embodiments, high order aberrations may undergo certain changes as a result of wavefront propagation. For example, high order aberrations such as coma may present an elliptical, a bi-elliptical, a four-fold elliptical, or another noncircular shape or boundary. Embodiments provide solutions to the current needs for wavefront propagation techniques. Embodiments include approaches for addressing low and high order ocular aberrations as they propagate. Embodiments also encompass verification techniques for low order and high order aberration approaches. Further, embodiments include the propagation of wavefronts with single-term aberrations.

In a first aspect, embodiments of the present invention provide a method of calculating a refractive treatment shape for ameliorating a vision condition in an eye of a patient. The method can include, for example, determining a measurement surface aberration corresponding to a measurement surface of the eye, where the measurement surface aberration includes a measurement surface boundary and a measurement surface magnitude. The method can also involve determining a propagation distance between the measurement surface of the eye and a treatment surface, and determining a treatment surface aberration based on the measurement surface aberration and the propagation distance. The treatment surface aberration can include a treatment surface boundary and a treatment surface magnitude. The method can also include calculating the refractive treatment shape based on the treatment surface aberration. In some cases, the refractive treatment shape is configured to ameliorate a high order aberration of the measurement surface aberration. In some cases, a difference between the treatment surface magnitude and the measurement surface magnitude is proportional to the propagation distance. In some cases, a difference between the treatment surface magnitude and the measurement surface magnitude is proportional to a direction factor. In some cases, a difference between the treatment surface magnitude and the measurement surface magnitude is inversely proportional to a dimension of the measurement surface boundary. In some cases, a difference between the treatment surface magnitude and the measurement surface magnitude is inversely proportional to a squared radius of the measurement surface boundary. The measurement surface of the eye can correspond to a pupil plane of the eye, and the treatment surface can correspond to a corneal plane or a spectacle plane of the eye. In some aspects, the measurement surface aberration includes a wavefront measurement surface aberration, and the treatment surface aberration includes a wavefront treatment surface aberration. In some aspects, the measurement surface boundary includes a wavefront measurement surface boundary, and the treatment surface boundary includes a wavefront treatment surface boundary. A measurement surface magnitude may include a set of measurement surface coefficients, and a treatment surface magnitude may include a set of treatment surface coefficients. Optionally, a measurement surface magnitude may include a set of measurement surface wavefront coefficients, and a treatment surface magnitude may include a set of treatment surface wavefront coefficients.

In another aspect, embodiments of the present invention encompass methods of calculating a refractive treatment shape for ameliorating a vision condition in an eye of a patient. A method may include, for example, determining a first wavefront measurement corresponding to the pupil plane of the eye, where the first wavefront measurement includes a first wavefront boundary and a first set of wavefront coefficients. The method may also include determining a propagation distance between the pupil plane of the eye and a treatment surface, and determining a propagated wavefront measurement corresponding to the treatment surface based on the first wavefront measurement and the propagation distance. The propagated wavefront measurement can include a second wavefront boundary and a second set of wavefront coefficients. The method may also include calculating the refractive treatment shape based on the propagated wavefront measurement. In some cases, the treatment surface corresponds to a corneal surface, a spectacle surface, a scleral lens surface, a contact lens surface, or an intraocular lens surface. Methods may also involve applying the refractive treatment shape to the eye of the patient to ameliorate the vision condition. In some cases, the e refractive treatment shape is applied to the eye of the patient in a selected treatment modality. The example, the method can encompass ablating a corneal surface of the eye to provide a corneal surface shape that corresponds to the refractive treatment shape, providing the patient with a contact lens that has a shape that corresponds to the refractive treatment shape, providing the patient with a spectacle that has a shape that corresponds to the refractive treatment shape, providing the patient with a scleral lens that has a shape that corresponds to the refractive treatment shape, or providing the patient with an intraocular lens that has a shape that corresponds to the refractive treatment shape.

In some aspects, embodiments of the present invention include systems for generating a refractive treatment shape for ameliorating a vision condition in an eye of a patient. A system may include, for example, an input module that accepts a measurement surface aberration corresponding to a measurement surface of the eye, where the measurement surface aberration includes a measurement surface boundary and a measurement surface magnitude. The system can also include a transformation module that derives a treatment surface aberration corresponding to a treatment surface of the eye. The treatment surface aberration may be based on the measurement surface aberration and a propagation distance between the measurement surface and a treatment surface. The treatment surface aberration may include a treatment surface boundary and a treatment surface magnitude. A system may also include an output module that generates the refractive treatment shape based on the treatment surface aberration. In some system embodiments, a difference between the treatment surface magnitude and the measurement surface magnitude is proportional to the propagation distance. In some embodiments, a difference between the treatment surface magnitude and the measurement surface magnitude is proportional to a direction factor. In some embodiments, a difference between the treatment surface magnitude and the measurement surface magnitude is inversely proportional to a dimension of the measurement surface boundary. In some embodiments, a difference between the treatment surface magnitude and the measurement surface magnitude is inversely proportional to a squared radius of the measurement surface boundary. A treatment surface can correspond to a corneal surface, a spectacle surface, a scleral lens surface, a contact lens surface, or an intraocular lens surface, for example.

In a further aspect, embodiments of the present invention encompass methods for characterizing an electromagnetic field that is propagated from a first surface to a second surface, and systems for carrying out such methods. Exemplary methods may involve determining a first surface characterization of the electromagnetic field corresponding to the first surface, where the first surface characterization includes a first surface field strength. Methods may also involve determining a propagation distance between the first surface and a second surface, and determining a second surface characterization of the electromagnetic field based on the first surface characterization and the propagation distance. In some cases, the second surface characterization includes a second surface field strength. In some cases, the first surface field strength includes a first surface field phase, and the second surface field strength includes a second surface field phase.

In one aspect, the present invention provides a method of determining a refractive treatment shape for ameliorating a vision condition in a patient. The method comprises measuring a wavefront aberration of an eye of the patient in order to provide a measurement surface aberration, deriving a treatment surface aberration of the eye based on the measurement surface aberration, and determining the refractive treatment shape based on the treatment surface aberration of the eye. The wavefront aberration can correspond to a measurement surface that is disposed at or near a pupil plane of the eye, and the treatment surface aberration can correspond to a treatment surface that is disposed at or near an anterior surface of a cornea of the eye. The treatment surface aberration may be derived using a difference between the measurement surface and the treatment surface.

In another aspect, the present invention provides a method of ameliorating a vision condition in a patient. The method comprises measuring a wavefront aberration of an eye of the patient in order to provide a measurement surface aberration, deriving a treatment surface aberration of the eye from the measurement surface aberration, determining a refractive treatment shape based on the treatment surface aberration of the eye, and applying the refractive treatment shape to the eye of the patient to ameliorate the vision condition. The wavefront aberration can correspond to a measurement surface that is disposed at or near a pupil plane of the eye. The treatment surface aberration can correspond to a treatment surface that is disposed at or near an anterior corneal surface of the eye, or a treatment surface that corresponds to a spectacle plane of the eye. Relatedly, the treatment surface may be disposed posterior to a pupil plane of the eye. The treatment surface aberration may be based on a difference between the measurement surface and the treatment surface.

In a related aspect, the refractive treatment shape can be applied to the eye of the patient in a variety of treatment modalities. For example, the treatment shape can be applied by ablating a corneal surface of the patient to provide a corneal surface shape that corresponds to the refractive treatment shape. The treatment shape may also be applied by providing the patient with a contact lens that has a shape that corresponds to the refractive treatment shape. Further, the treatment shape may be applied by providing the patient with a spectacle lens that has a shape that corresponds to the refractive treatment shape. What is more, the treatment shape can be applied by providing the patient with an intra-ocular lens that has a shape that corresponds to the refractive treatment shape.

In another aspect, the present invention provides a system for generating a refractive treatment shape for ameliorating a vision condition in an eye of a patient. The system comprises an input module that accepts a measurement surface aberration, a transformation module that derives a treatment surface aberration based on the measurement surface aberration, and an output module that generates the refractive treatment shape based on the treatment surface aberration. The measurement surface aberration may be based on a wavefront aberration of the eye. The wavefront aberration can correspond to a measurement surface that is disposed at or near a pupil plane of the eye. The treatment surface aberration can correspond to a treatment surface that is disposed at or near an anterior corneal surface of the eye, or a treatment surface that corresponds to a spectacle plane of the eye. Relatedly, the treatment surface may be disposed posterior to a pupil plane of the eye. The treatment surface aberration may be based on a difference between the measurement surface and the treatment surface.

In another aspect, the present invention provides a system for ameliorating a vision condition in an eye of a patient. The system comprises an input module that accepts a measurement surface aberration, a transformation module that derives a treatment surface aberration based on the measurement surface aberration, an output module that generates a refractive treatment shape based on the treatment surface aberration, and a laser system that directs laser energy onto the eye according to the refractive treatment shape so as to reprofile a surface of the eye from an initial shape to a subsequent shape, the subsequent shape having correctively improved optical properties for ameliorating the vision condition. The measurement surface aberration may be based on a wavefront aberration of the eye. The wavefront aberration can correspond to a measurement surface that is disposed at or near a pupil plane of the eye, and the treatment surface aberration can correspond to a treatment surface that is disposed at or near an anterior surface of a cornea of the eye. The treatment surface aberration can be derived based on a difference between the measurement surface and the treatment surface.

In some aspects, the treatment surface aberration may be a treatment surface wavefront map. In other aspects, the measurement surface aberration may be a measurement surface wavefront map. The treatment surface wavefront map may be derived at least in part by local slope scaling of the measurement surface wavefront map. In still other aspects, the treatment surface wavefront map may be derived at least in part by applying a scaling factor of $1/(1+Pd)$ to a slope of the measurement surface wavefront map, where P represents a local curvature of the measurement surface wavefront map and d represents a difference between the measurement surface and the treatment surface. In a related aspect, a difference between the measurement surface and a retinal surface of the eye corresponds to a first vertex measure, and a difference between the treatment surface and the retinal surface of the eye corresponds to a second vertex measure. P may be based on a second derivative of the measurement surface wavefront map. P may also be based on a pupil radius of the eye.

In some aspects, the treatment surface wavefront map can be derived according to an iterative Fourier reconstruction algorithm. What is more, the measurement surface aberration may reflect low order and/or high order aberrations of the eye of the patient.

In another aspect, the present invention provides a system for generating a prescription for ameliorating a vision condition in an eye of a patient. The system comprises an input that accepts irregular aberration data corresponding to an aberration measurement surface adjacent a pupil plane of the eye, a transformation module that derives a treatment surface aberration corresponding to a treatment surface that is disposed adjacent an anterior surface of a cornea of the eye, and an output module that generates the prescription based on the treatment surface aberration. The treatment surface aberration can be derived from the irregular aberration data using a difference between the measurement surface and the treatment surface.

In one aspect, embodiments of the present invention provide a method of calculating a refractive treatment shape for ameliorating a vision condition in an eye of a patient. The method can include determining a first wavefront measurement corresponding to the pupil plane of the eye. The first wavefront measurement can include a first wavefront boundary and a first set of wavefront coefficients. The method can also include determining a propagation distance between the pupil plane of the eye and a treatment surface, and determining a propagated wavefront measurement corresponding to the treatment surface based on the first wavefront measurement and the propagation distance. The propagated wavefront measurement can include a second wavefront boundary and a second set of wavefront coefficients. The method can also include calculating the refractive treatment shape based on the propagated wavefront measurement. In some cases, the treatment surface corresponds to a corneal surface, a spectacle surface, a scleral lens surface, a contact lens surface, or an intraocular lens surface.

In another aspect, embodiments of the present invention provide a method of ameliorating a vision condition in an eye of a patient. The method includes determining a first wavefront measurement corresponding to the pupil plane of the eye. The first wavefront measurement can include a first wavefront boundary and a first set of wavefront coefficients. The method can also include determining a propagation distance between the pupil plane of the eye and a treatment surface, and determining a propagated wavefront measurement corresponding to the treatment surface based on the first wavefront measurement and the propagation distance. The propagated wavefront measurement can include a second wavefront boundary and a second set of wavefront coefficients. The method can also include calculating the refractive treatment shape based on the propagated wavefront measurement, and applying the refractive treatment shape to the eye of the patient to ameliorate the vision condition. In some cases, the refractive treatment shape is applied to the eye of the patient in a treatment modality such as ablating a corneal surface of the eye to provide a corneal surface shape that corresponds to the refractive treatment shape, providing the patient with a contact lens that has a shape that corresponds to the refractive treatment shape, providing the patient with a spectacle that has a shape that corresponds to the refractive treatment shape, providing the patient with a scleral lens that has a shape that corresponds to the refractive treatment shape, or providing the patient with an intraocular lens that has a shape that corresponds to the refractive treatment shape.

In still another aspect, embodiments of the present invention provide a system for generating a refractive treatment shape for ameliorating a vision condition in an eye of a patient. The system can include an input module that accepts a first wavefront measurement corresponding to the pupil plane of the eye. The first wavefront measurement can include a first wavefront boundary and a first set of wavefront coefficients. The system can also include a transformation module that derives a propagated wavefront measurement. The propagated wavefront measurement can correspond to a treatment surface of the eye and include a second wavefront boundary and a second set of wavefront coefficients. The propagated wavefront measurement can be derived from the first wavefront measurement using a propagation distance between the first wavefront measurement and the treatment surface. The system can also include an output module that generates the refractive treatment shape based on the propagated wavefront measurement.

These and other aspects will be apparent in the remainder of the figures, description, and claims.

DETAILED DESCRIPTION OF THE INVENTION

The present invention provides methods, software, and systems for processing optical power measurements taken at a first plane and converting those power measurements to corrective optical power measurements that can be used at a second plane.

The present invention is generally useful for enhancing the accuracy and efficacy of laser eye surgical procedures, such as photorefractive keratectomy (PRK), phototherapeutic keratectomy (PTK), laser in situ keratomileusis (LASIK), and the like. The present invention can provide enhanced optical accuracy of refractive procedures by improving the methodology for processing measured optical errors of the eye and hence calculate a more accurate refractive ablation program. In one particular embodiment, the present invention is related to therapeutic wavefront-based ablations of pathological eyes.

The present invention can be readily adapted for use with existing laser systems, wavefront measurement systems, and other optical measurement devices. While the systems, software, and methods of the present invention are described primarily in the context of a laser eye surgery system, it should be understood the present invention may be adapted for use in alternative eye treatment procedures, systems, or modalities, such as spectacle lenses, intraocular lenses, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy.

Figure 1:
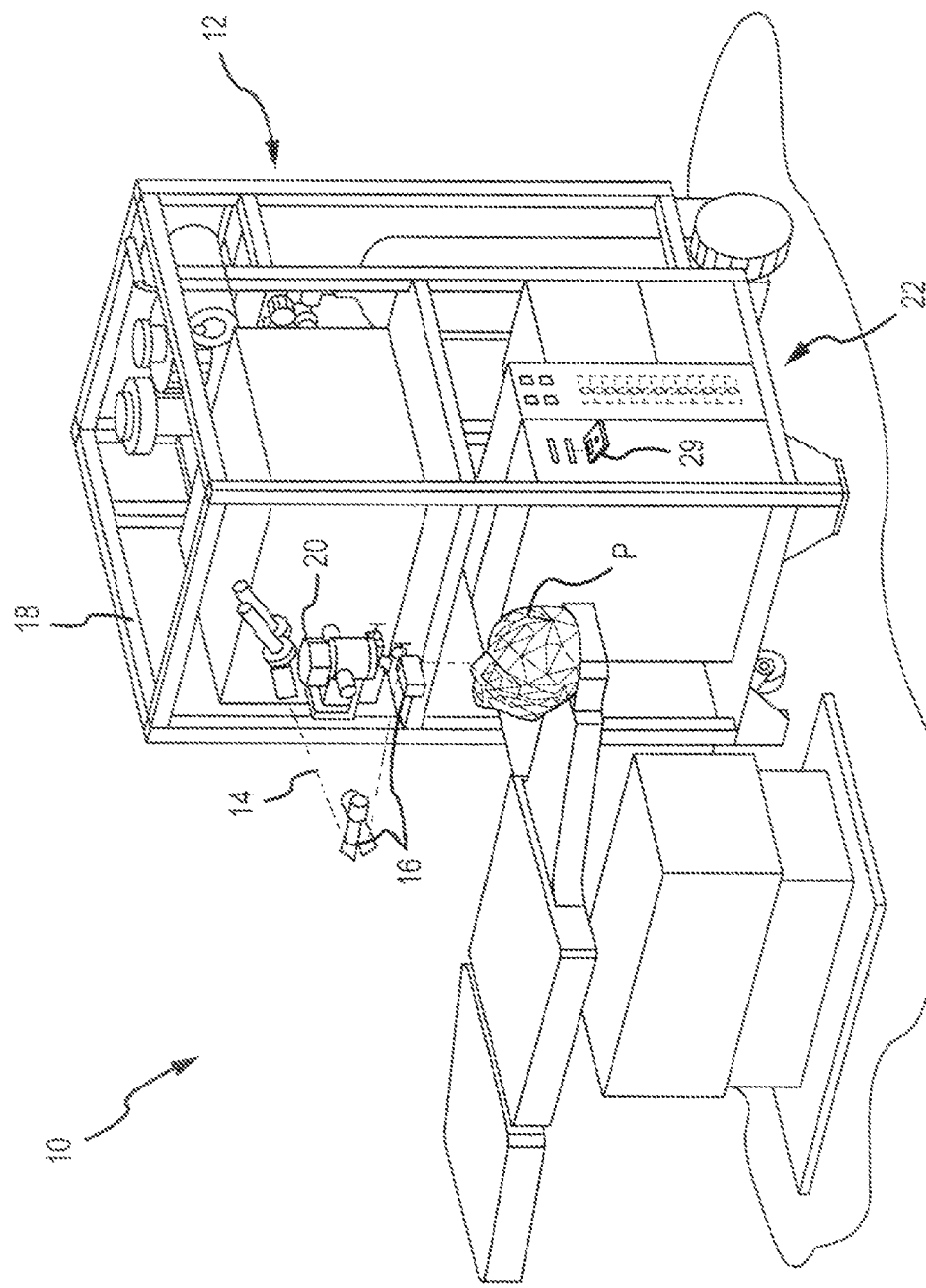
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 215 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Basis data can be further characterized for particular lasers or operating conditions, by taking into account localized environmental variables such as temperature, humidity, airflow, and aspiration.

Figure 2:
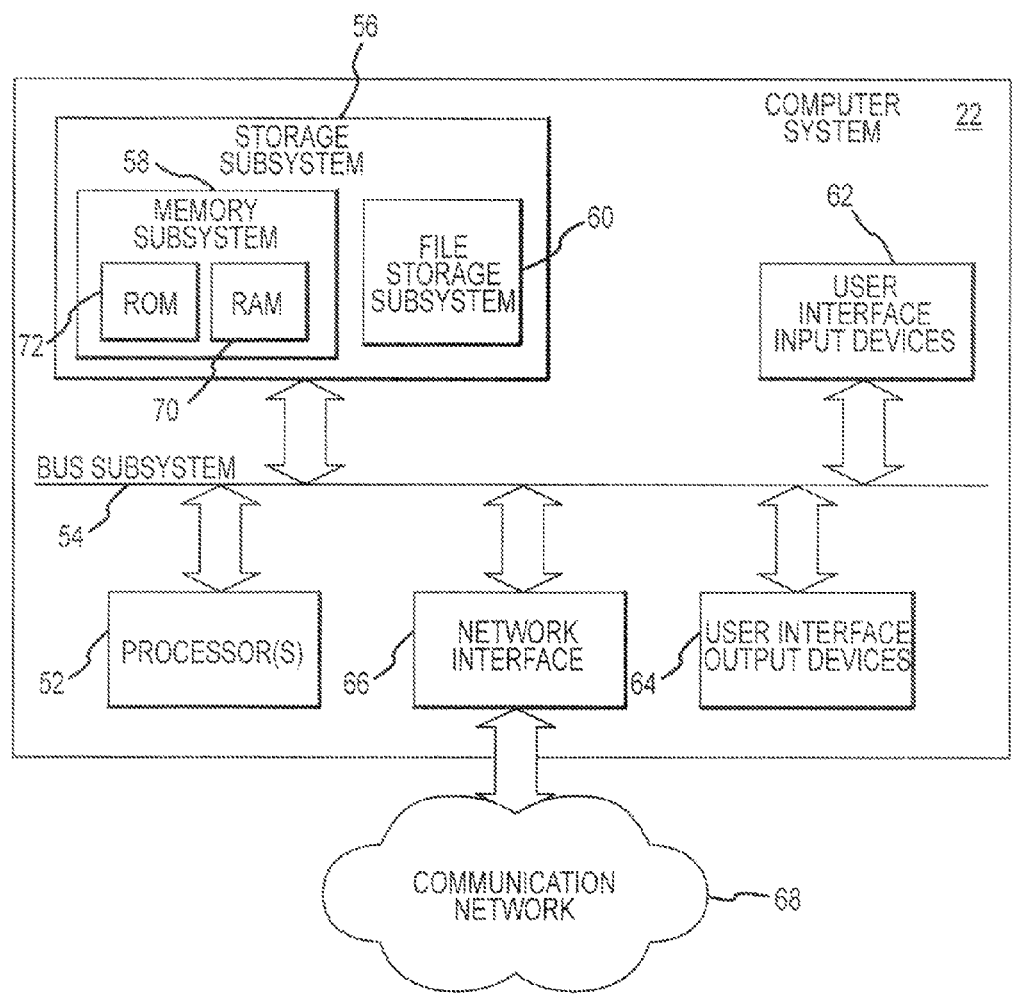
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
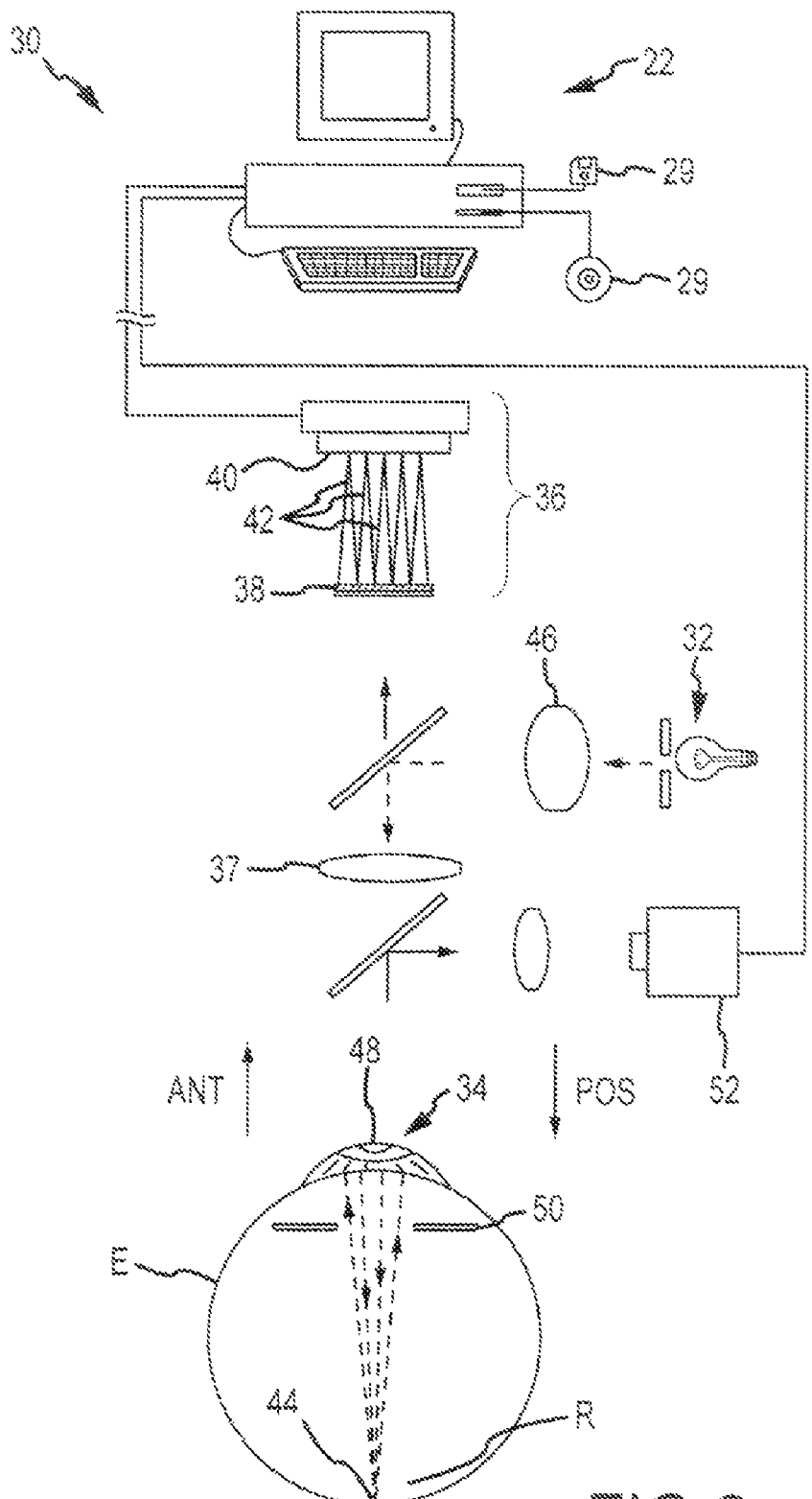
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
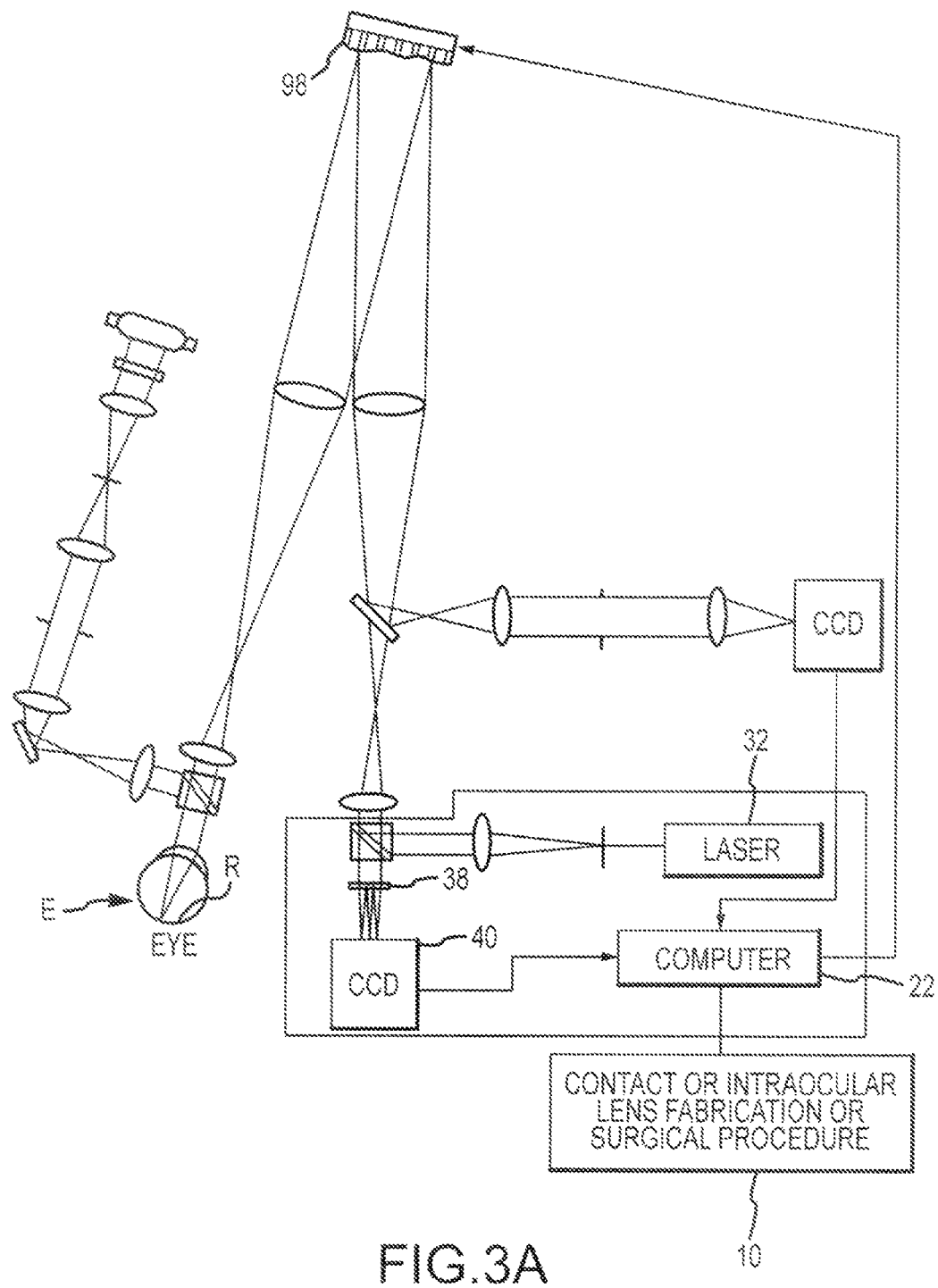
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations comprise elements of a VISX WaveScan®, available from VISX, INCORPORATED of Santa Clara, Calif. One embodiment includes a WaveScan® with a deformable mirror as described above. An alternate embodiment of a wavefront measuring system is described in U.S. Pat. No. 6,271,915, the full disclosure of which is incorporated herein by reference.

Figure 4:
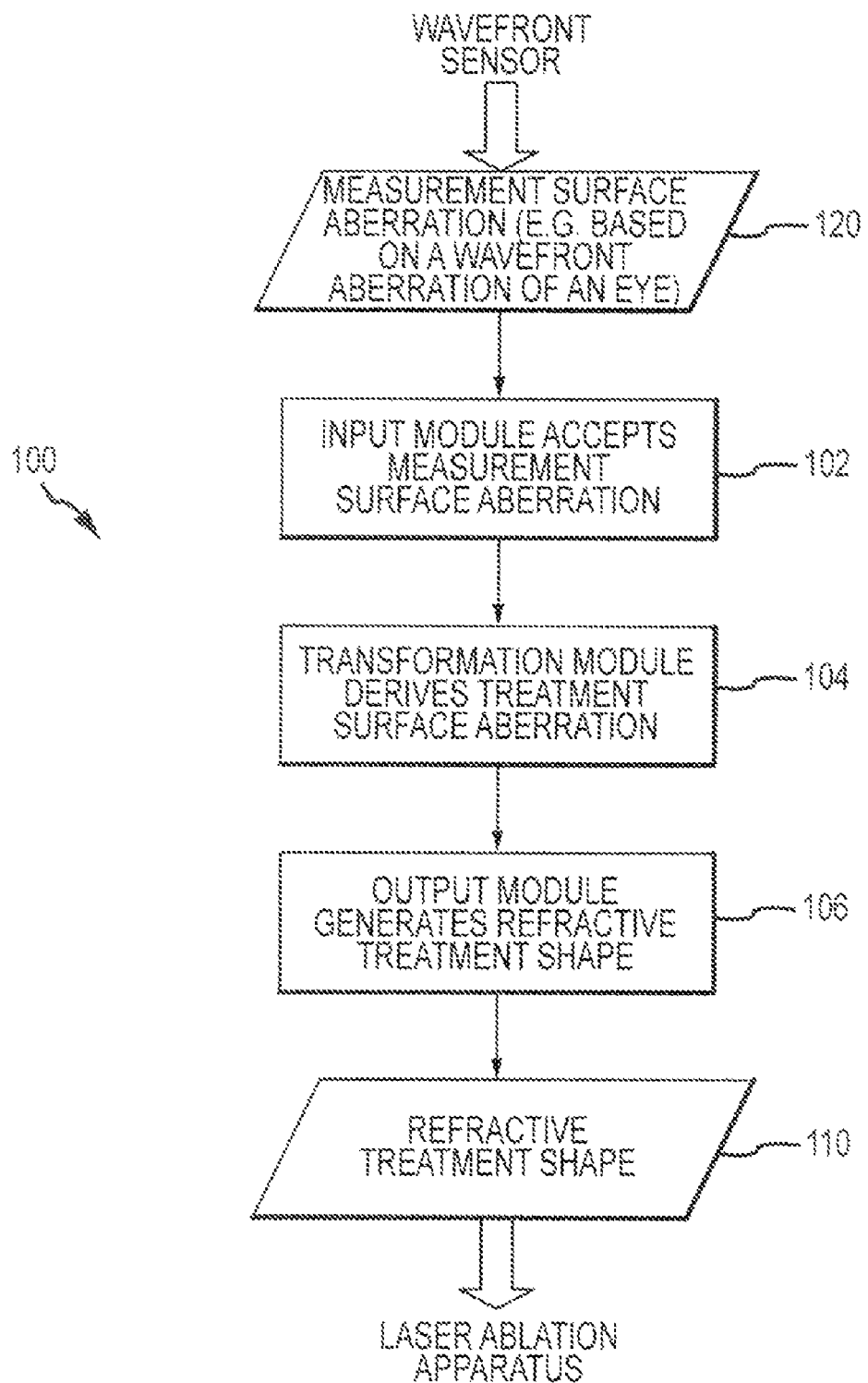
FIG. 4 schematically represents a simplified set of modules that carry out one method of the present invention.

FIG. 4 schematically illustrates a simplified set of modules, or a correction system 100, for carrying out a method according to one embodiment of the present invention. Correction system 100 can be integrated or interfaced with, for example, computer system 22, or otherwise used in conjunction with laser surgical system 10. The modules may be software modules on a computer readable medium that is processed by processor 52 (FIG. 2), hardware modules, or a combination thereof. Any of a variety of commonly used platforms, such as Windows, MacIntosh, and Unix, along with any of a variety of commonly used programming languages, may be used to implement the present invention.

Correction system 100 can be configured to generate a refractive treatment shape 110 for ameliorating a vision condition in a patient. An input module 102 typically receives a measurement surface aberration 120, such as wavefront aberration data from wavefront sensors, which characterize aberrations and other optical characteristics of the entire optical tissue system imaged. Often, the wavefront aberration corresponds to a measurement surface that is disposed at or near a pupil plane of the eye. The data from the wavefront sensors are typically generated by transmitting an image (such as a small spot or point of light) through the optical tissues, as described above. Measurement surface aberration 120 can include an array of optical gradients or a gradient map.

Correction system 100 can include a transformation module 104 that derives a treatment surface aberration. The treatment surface aberration can correspond to a treatment surface that is disposed at or near an anterior corneal surface of the eye, or a treatment surface that corresponds to a spectacle plane of the eye. Relatedly, the treatment surface may be disposed posterior to a pupil plane of the eye. Often, the treatment surface aberration is derived from measurement surface aberration 120 using a difference between the measurement surface and the treatment surface. For example, optical gradient data from input module 102 may be transmitted to transformation module 104, where a treatment surface aberration is mathematically reconstructed based on the optical gradient data.

Correction system 100 can include an output module 106, such that the treatment surface aberration generated by transformation module 104 can then be transmitted to output module 106 where a refractive treatment shape 110 can be generated based on the treatment surface aberration. Refractive treatment shape 110 may be transmitted to a laser treatment apparatus for generation of a laser ablation treatment for the patient. Similarly, refractive treatment shape 110 may form the basis for fabrication of contact lenses, spectacles, or intraocular lenses.

As can be appreciated, the present invention should not be limited to the order of steps, or the specific steps illustrated, and various modifications to the method, such as having more or less steps, may be made without departing from the scope of the present invention.

Figure 5:
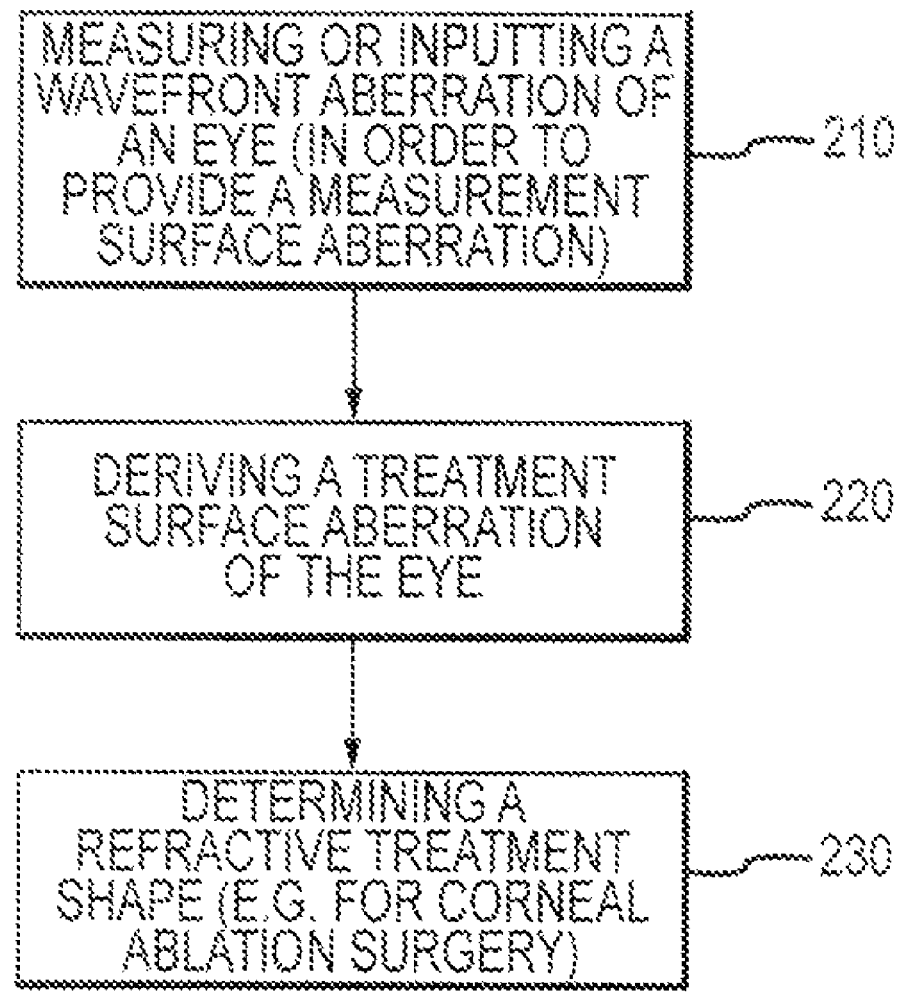
FIG. 5 is a flow chart that schematically illustrates a method of determining a refractive treatment shape according to one embodiment of the present invention.

In one embodiment, the present invention provides a method of determining a refractive treatment shape for ameliorating a vision condition in a patient. FIG. 5 depicts the steps of an exemplary method according to the present invention. The refractive treatment shape can be based on a treatment surface aberration that is derived from a measurement surface aberration.

Figure 5A:
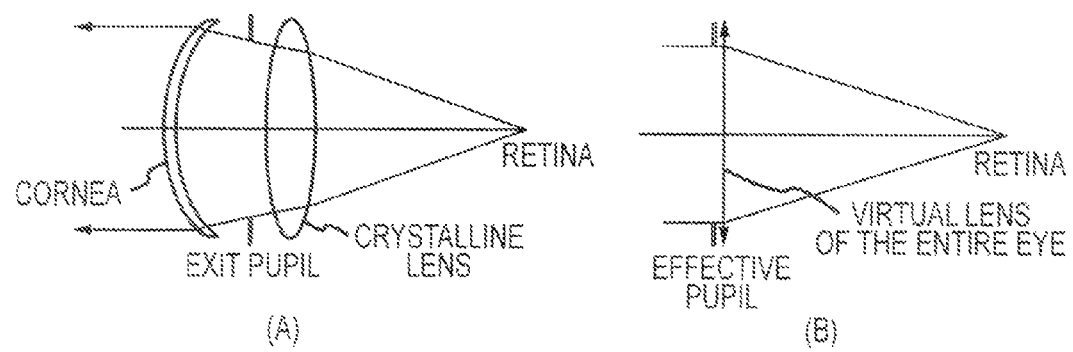
FIG. 5A depicts aspects of ocular wavefront sensing for Hartmann-Shack aberrometry according to embodiments of the present invention.

For ocular wavefront measurements, the Hartmann-Shack wavefront sensor (Liang, J. et al., *J. Opt. Soc. Am. A* 11:1949-1957 (1994)) can be used as an aberrometer. FIGS. 5A(a) and 5A(b) show aspects of the ocular wavefront sensing for the Hartmann-Shack aberrometry according to embodiments of the present invention. FIG. 5A(a) shows that a parallel wave can be formed when the rays of a beacon from the retina pass through an eye with no ocular aberrations. As shown in FIG. 5A(b), when the optics of the entire eye are simplified as a virtual lens, the effective pupil can be one that is magnified and anterior to the virtual lens. As shown in FIG. 5A(a), a thin beam of light can be projected onto the retina to form a beacon in such an outgoing wavefront sensing system. The rays of the pseudo point source pass through the optics of the eye to become a plane wave, if there are no ocular aberrations in the eye. However, if ocular aberrations exist, the rays would not form a plane wave and the deviations in the optical path difference can be measured as the ocular wavefront.

The ocular wavefront diameter can be determined by the pupil size. Because of the large dioptric power of the cornea, a significant magnification of the pupil size may occur. In the optics of a Hartmann-Shack wavefront sensor, the detected pupil size on a CCD camera is typically the magnified pupil size, not the physical pupil size. The representation of a wavefront may therefore use a magnified pupil size, as can be explained by FIG. 5A(b). In FIG. 5A(b), the entire optics of the eye are simplified as a thin lens, and the effective pupil is immediately anterior to the simplified lens. Because the parallel wave is formed after it leaves the entire optics of the eye, the effective pupil size is tied to the size when the wavefront becomes parallel. Therefore, the magnified pupil size can be taken as the wavefront diameter.

However, the ocular wavefront is often measured on the exit pupil plane. Even though the boundary of the wavefront is the magnified pupil size, it is different than when it propagates to the curved cornea surface or other planes, such as a spectacle plane. The problem for the power change for correcting astigmatic eyes at different spectacle planes was investigated extensively by Harris (Harris, W. F. $Optom. Vis. Sci.$ 73:606-612 (1996)). For ocular wavefronts that include high order aberrations, the problem for such propagations has not been considered. Although the light rays form a diverging wave before they leave the surface of the cornea, they become parallel wave when they pass the surface of the cornea. Embodiments of the present invention address free space wavefront propagation with the flat surface as a reference plane. Embodiments also encompass the propagation of the spherocylindrical ocular aberrations, as well as a more generic approach that includes the treatment of the wavefront propagation of both low order and high order aberrations.

I. Measurement Surface Aberration

In general terms, a measurement surface aberration can be determined from optical data corresponding to a measurement surface. For example, a measurement surface aberration can be determined by measuring a wavefront aberration of an eye of a patient. Measurement surface aberrations can be determined by aberrometers such as Hartmann-Shack aberrometers, ray tracing aberrometers, Tscherning aberrometers, Scheiner aberrometers, double-pass aberrometers, and the like, as well as topographical devices. In some embodiments, a wavefront measurement system that includes a wavefront sensor (such as a Hartmann-Shack sensor) may be used to obtain one or more measurement surface aberrations (e.g. wavefront maps) of the optical tissues of the eye. The wavefront map may be obtained by transmitting an image through the optical tissues of the eye and sensing the exiting wavefront surface. From the wavefront map, it is possible to calculate a surface gradient or gradient map across the optical tissues of the eye. A gradient map may comprise an array of the localized gradients as calculated from each location for each lenslet of the Hartmann-Shack sensor. Measurement surface aberrations can correspond to a first plane or surface, and can encompass a first measurement surface boundary and a first measurement surface set of coefficients. For example, a first wavefront measurement can include a first wavefront boundary and a first set of wavefront coefficients. In some embodiments, a system or method may involve a measurement surface aberration corresponding to a measurement surface of the eye. The measurement surface aberration may include a measurement surface boundary and a measurement surface magnitude.

A. Measurement Surface

There are a variety of devices and methods for measuring surface characteristics of optical systems. The category of aberroscopes or aberrometers includes classical phoropter and wavefront approaches. Classical phoropters can be used to record optical data corresponding to a measurement surface that is disposed anterior to the cornea of an eye. For example, phoropters can measure low order aberrations at a distance of about 12.5 mm anterior to the corneal surface. In many cases, this will correspond to a spectacle plane of the eye. Wavefront devices are often used to measure both low order and high order aberrations adjacent a pupil plane, which can be about 3.5 mm posterior to the corneal surface. Another category of measuring approaches includes topography based measuring devices and methods. Topography typically involves providing optical data corresponding to a measurement surface that is disposed at or near the corneal surface of the eye. In some embodiments, the terms "plane" and "surface" may be used interchangeably.

B. Aberration

As noted above, the measurement surface aberration can be based on a refractive measurement as determined by an optometer, or any of a wide variety of devices for obtaining irregular aberration data. Similarly, the measurement surface aberration can be a measurement surface wavefront map, as determined by a wavefront measurement device. What is more, the measurement surface aberration may reflect both low order and high order aberrations of the eye of a patient. In some cases, aberrations can be embodied as an elevation map, a surface map, or the like.

II. Treatment Surface Aberration

When a measurement surface aberration of an optical system has been determined, it is then possible to derive a treatment surface aberration of the optical system. In the case of refractive surgical methods, for example, a treatment surface aberration corresponding to a corneal plane can be derived from a measurement surface aberration as determined in a plane other than the corneal plane. Treatment surface aberrations can correspond to a second plane or surface, and can encompass a second surface boundary and a second surface set of coefficients. For example, a treatment surface aberration can include a first treatment boundary and a first set of treatment coefficients. In some embodiments, systems or methods can involve a propagation distance between a measurement surface of the eye and a treatment surface of the eye. Embodiments also encompass a treatment surface aberration based on the measurement surface aberration and the propagation distance. A treatment surface aberration can include a treatment surface boundary and a treatment surface magnitude.

A. Treatment Surface

The treatment surface aberration corresponds to a treatment surface, which is typically disposed at or near an anterior surface of a cornea of an eye. Often, the treatment surface will correspond to a corneal plane associated with the eye, as in the case of ablative laser eye surgery or contact lens treatments. At other times, the treatment surface may correspond to a spectacle plane associated with the eye, as in the case of spectacle treatments. Further, the treatment surface can be posterior to the pupil plane of the eye, as in the case of intraocular lens treatments. As noted above, in some embodiments, the terms "plane" and "surface" may be used interchangeably.

B. Derivation of Treatment Surface Aberration

The treatment surface aberration can be derived from the measurement surface aberration, based on a difference between the measurement surface and the treatment surface. The difference between the measurement surface and the treatment surface, for example, can include a distance measurement that represents a difference between the two surfaces. In some embodiments, the distance measurement is based on a vertex distance difference, the vertex distance difference reflecting a distance between a vertex of the measurement surface and a vertex of the treatment surface.

1. Classical Vertex Correction Formulas

Figure 6:
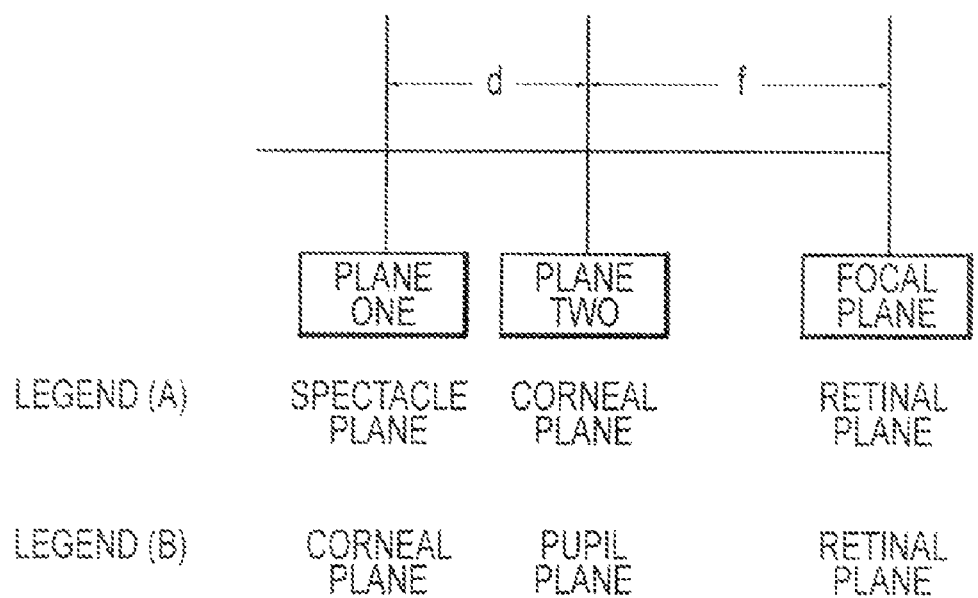
FIG. 6 illustrates a model optical system according to an embodiment of the present invention.

Traditionally, the power of a lens is measured in diopters, and can be defined as the reciprocal of the lens focal length in meters. FIG. 6 shows a schematic diagram of an optical system. The system includes a first plane disposed at a first distance from a focal plane, the first distance corresponding to a first focal length, and a second plane disposed at a second distance from the focal plane, the second distance corresponding to a second focal length. Although the first and second planes are illustrated as flat surfaces, these planes can also represent curved surfaces such as lenses, wavefronts, and other representations of optical surfaces or systems. In the exemplary optical system depicted by FIG. 6 legend (a), the focal plane may be associated with a retinal plane, the first plane may be associated with a spectacle plane, and the second plane may be associated with a corneal plane.

A treatment surface can correspond to, or be based upon, a spectacle surface, corneal surface, pupil surface, and the like. A spectacle surface is typically about 12.5 mm anterior to the cornea of the eye. A pupil surface or plane is typically about 3.5 mm posterior to the cornea of the eye. An intraocular lens surface is usually about 0.5 mm posterior to the pupil surface or plane of the eye. A contact lens surface is typically at or slightly anterior to the cornea of the eye. If the treatment surface and the measurement surface are substantially in the same plane, there may be no need for a vertex correction.

When prescribing spectacles, for example, an optometrist may first make or consider an aberration measurement such as a refractive measurement of the eye, where the aberration measurement corresponds to a measurement surface at or near a pupil plane or surface of the eye. Because the treatment surface may not be the same as the measurement surface, it is often desirable to make a power adjustment in order to determine the corrective surface shape or treatment surface aberration. In the case of spectacles, the treatment surface is disposed anterior to the corneal surface, usually by about 12.5 mm.

Likewise, when prescribing contact lenses, an optometrist can consider a refractive correction corresponding to the spectacle plane, and make a power adjustment to account for the difference between the spectacle plane and the corneal plane. In this case, the adjustment often depends on a vertex distance, corresponding to the distance between the posterior surface of the spectacle lens and the anterior surface of the cornea.

Thus, given a measurement surface aberration, it is possible to derive a treatment surface aberration based on a difference between the treatment surface and the measurement surface. Often, the difference will be a vertex distance between the treatment surface and the measurement surface. As further discussed below, the treatment surface aberration can then be used to determine a refractive treatment shape. In the case of corrective spectacles, the refractive treatment shape can be a basis for a prescription for the patient, where the treatment shape corresponds to the spectacle plane or surface.

Typically, the measurement surface aberration corresponds to a first power data, and the treatment surface aberration corresponds to a derived second power data. The second power data can be derived from the first power data and the distance between the measurement surface and the treatment. To achieve the effect of a power change, in terms of a vertex correction, a vertex distance measure can be based on a difference between the measurement surface and the treatment surface. The vertex correction represents a power change between the first power data and the second power data. In this sense, the derivation of the second power corresponds to a vertex correction of the first power. The vertex of a lens curve can be defined as the apex of the lens curve, or as the point on the lens curve in which the lens curve axis intersects it.

a. Traditional (Non Wavefront)

Traditional phoropters can be used to make traditional optical aberration measurements such as sphere and cylinder. Such aberration measurements are often expressed in terms of dioptric power. Referring again to FIG. 6 legend (a), assuming the power corresponding to the second plane, e.g. a corneal plane, is S, and the power corresponding the first plane, e.g. a spectacle plane, is S', it is possible to describe the relationship between the two powers with the following equations.

$$S = \frac{1}{f}, \quad (1)$$

$$S' = \frac{1}{f+d} = \frac{S}{1+dS} \quad (2)$$

Power can be expressed in units of diopters. f represents the distance between the focal plane and the second plane, although here this term is not a factor in the relationship between the two power measurements S and S'. d represents the vertex distance between the first and second planes. Where a first plane treatment surface is disposed anterior to a second plane measurement surface, d will typically have a positive value. For example, for spectacle treatments, d can be about 0.0125 m, and for refractive surgery treatments, d can be about 0.0035 m. Conversely, where the first plane treatment shape is disposed posterior to a second plane measurement surface, d will typically have a negative value. For example, for intraocular lens treatments, d can be about −0.0005 m.

Sphere is a low order aberration corresponding to defocus, and cylinder is a low order aberration corresponding to astigmatism. To consider a combination of sphere and cylinder powers, it is possible to replace S by (S+C) where C stands for cylinder power at the maximum meridian. Thus, cylinder at the spectacle plane can be represented by C', where $$C' = \frac{S+C}{1+d(S+C)} - S'. \quad (3)$$

These formulae can be used to calculate the power change associated with a vertex distance.

Figure 6A:
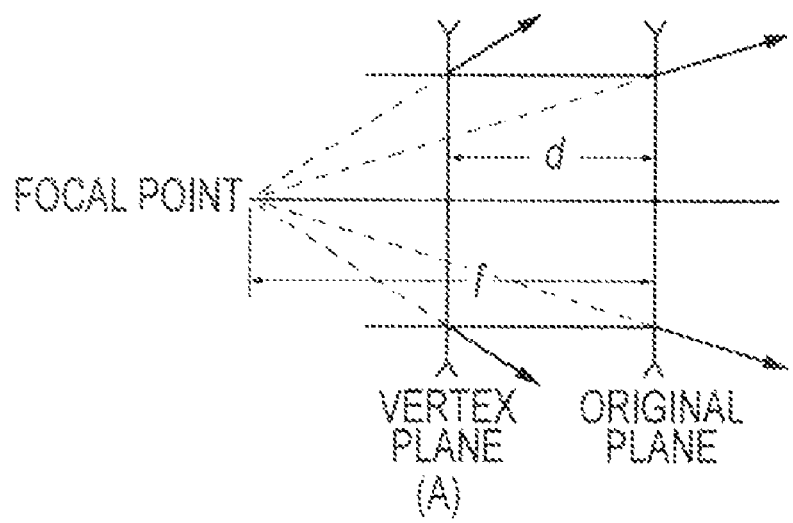
FIG. 6A shows geometry for a vertex correction for myopic and hyperopic cases according to embodiments of the present invention.
Figure 6A:
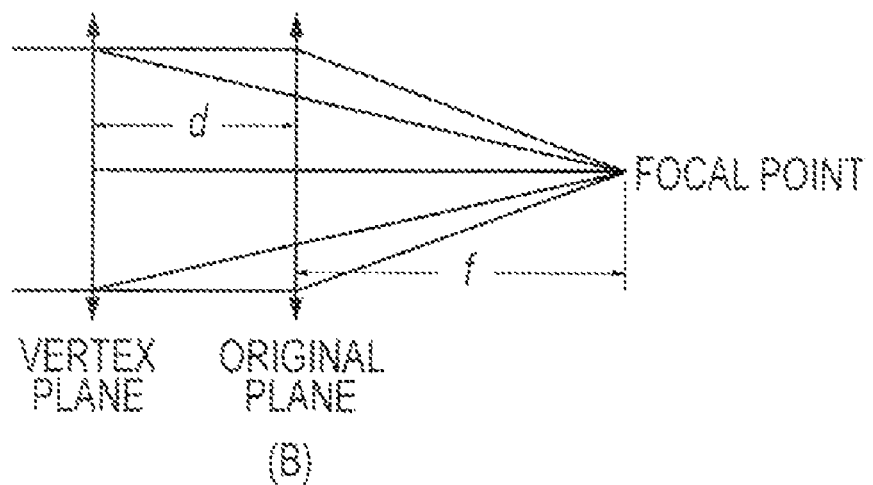

A related embodiment that encompasses a formulation of the classical vertex correction also addresses the situation where only low order aberrations, namely, the sphere and cylinder, exist. FIG. 6A shows geometries for the vertex correction for myopic and hyperopic cases according to embodiments of the present invention. FIG. 6A(a) shows a geometry for the vertex correction in a myopic case. FIG. 6A(b) shows a geometry for the vertex correction in a hyperopic case. In some embodiments, it is helpful to assume the original plane is less anterior than the new plane. In some cases, the focal length is f before the vertex correction and the vertex distance is d, both in meters. Suppose S stands for the sphere power and C stands for the cylinder power, both in diopters, before the vertex correction. After the vertex correction, the sphere and cylinder are denoted as S' and C'. Let's first consider the pure sphere case. From the geometrical optics, for the myopic case we have $$S = \frac{1}{f}, \quad (A1a)$$

$$S' = \frac{1}{f - d'}, \quad (A1b)$$

where f stands for the focal length and d for the vertex distance, both in meters. Solving for f from Eq. (A1a) and substituting it into Eq. (A1b), we obtain the vertex correction for myopia as $$S' = \frac{S}{1 - Sd}. \quad (A2)$$

Similarly, for the hyperopic case, we have $$S = \frac{1}{f}, \quad (A3a)$$

$$S' = \frac{1}{f + d'}, \quad (A3b)$$

and the vertex correction formula for hyperopic can be obtained as $$S' = \frac{S}{1 + Sd}. \quad (A4)$$

Noticing that for myopia, the convention is that the sphere power is negative so Eq. (A4) can be used for both cases of myopia and hyperopia. When the correction is in the reverse direction, i.e., changing the power from a more anterior plane to a less anterior plane, the vertex distance d should take a negative value.

For cylinder case, we only need to consider two meridians, the maximum power and the minimum power before and after the vertex correction. In plus cylinder notation, the maximum power is S+C and the minimum power is S. In minus cylinder notation, the maximum power is S and the minimum power is S+C. Therefore, only the two powers, S+C and S, need to be vertex corrected. With a similar approach, we can obtain the vertex correction formula for sphere and cylinder as $$S' = \frac{S}{1 + Sd}, \quad (A5a)$$

$$S' + C' = \frac{S + C}{1 + (S + C)d}. \quad (A5b)$$

Equation (A5) is the standard formula for vertex correction for low order spherocylindrical error. Again, when the correction is changed from a more anterior plane to a less anterior plane, the vertex distance d should take a negative value.

b. Wavefront

In addition to the traditional phoropter approaches discussed above, it is also possible to evaluate optical systems based on wavefront analysis. Wavefront analysis can be useful in evaluating low order and high order aberrations. Referring again to FIG. 6, it is possible to consider the first and second planes as associated with a general wavefront. The wavefront can begin at a virtual focal point corresponding to the focal plane, and propagate from plane two toward plane one. For each point along the wavefront surface, a local slope can be calculated. For example, the local slope can be the first derivative of the surface at a certain point. The local slope reflects a surface value at that point, as well as the surface values of the surrounding points. The local slope can be a direction-dependent vector. Because the wavefront local slopes are proportional to the local focal length, as the wavefront is propagated forward, the slope of the wavefront can be scaled by α factor of a such that:

$$\alpha = \frac{f}{f + d} \quad (4)$$

where f is the focal length of the wavefront and d is the vertex distance. Here, the vertex distance can represent a difference between the measurement surface, or plane two, and the treatment surface, or plane one. Thus, by making an initial measurement of the wavefront at plane two, it is possible to calculate a new wavefront surface at plane where individual points on the new surface have a local curvature that is derived by the scaling factor as discussed above. In the exemplary optical system depicted by FIG. 6 legend (b), the first plane can represent a corneal plane, the second plane can represent a pupil plane, and the focal plane can represent a retinal plane. If the treatment surface is anterior to the measurement surface, then the vertex distance is positive, and if the treatment surface is posterior to the measurement surface, then the vertex distance is negative. Similarly, for the myopia case, because the power is negative, the focal length could take a negative value. Generally α can have a positive value, as the absolute value of f is often much larger than d.

As discussed above, vertex correction can be used with traditional aberrometry approaches. It is also possible to use vertex correction with wavefront approaches. Here, W(x,y) represents the wavefront at the measurement plane and W'(x,y) represents the wavefront at the treatment plane with vertex distance of d. The local slope is assumed to be scaled, as discussed above. Thus, the following equations are partial derivatives of the corrected wavefront at the treatment plane.

$$\frac{\partial W'}{\partial x} = \frac{f}{f + d} \frac{\partial W}{\partial x} \quad (5)$$

$$\frac{\partial W'}{\partial y} = \frac{f}{f + d} \frac{\partial W}{\partial y}$$

It can be demonstrated that the classical formula for vertex correction holds with the assumption that the local slopes can be scaled according to a scaling factor of f/(f+d). The following examples illustrate this principle with respect to (i) sphere, or defocus, (ii) cylinder, or astigmatism, (iii) coma, and (iv) spherical aberration. Wavefronts can be expressed in terms of polynomial equations. This equation is useful for the derivations that follow.

$$\frac{\partial^2 W'}{\partial r^2} = \frac{x^2}{x^2+y^2}\frac{\partial^2 W'}{\partial x^2} + \frac{2xy}{x^2+y^2}\frac{\partial^2 W'}{\partial x \partial y} + \frac{y^2}{x^2+y^2}\frac{\partial^2 W'}{\partial y^2}. \quad (6)$$

(i) Sphere

In the following discussion, Zernike polynomials are used to represent the ocular aberrations. Starting with a sphere, where $W(r) = c_2^0 \sqrt{3}(2r^2-1)$, corresponding to the wavefront at the second plane, the curvature of the converted wavefront $W'(r)$ at the first plane can be expressed as $$\frac{\partial^2 W'}{\partial r^2} = \quad (7)$$
$$\frac{x^2}{x^2+y^2}\frac{\partial^2 W'}{\partial x^2} + \frac{2xy}{x^2+y^2}\frac{\partial^2 W'}{\partial x \partial y} + \frac{y^2}{x^2+y^2}\frac{\partial^2 W'}{\partial y^2} = 4\sqrt{3}\, c_2^0 \frac{f}{f+d},$$

or $$\frac{\partial^2 W'}{\partial r^2} = 4\sqrt{3}\, c_2^0 \frac{f}{f+d}, \quad (8)$$

where the curvature of the vertex corrected wavefront can be calculated using Equation (6). Here, r represents the normalized pupil radius with values from 0 to 1, x and y are the normalized values in x- and y-axis, f is the local focal length, or the reciprocal of local power, and $c_2^0$ is the Zernike coefficient of defocus term. From the definition of power, we have $$\frac{\partial^2 W}{\partial r^2} = 4\sqrt{3}\, c_2^0 \quad (9)$$
$$S = \frac{1}{R^2}\frac{\partial^2 W}{\partial r^2}$$
$$S' = \frac{1}{R^2}\frac{\partial^2 W'}{\partial r^2}.$$

From Equations (8) and (9), we obtain the following formula $$S' = \frac{f}{f+d}\, S = \frac{S}{1+Sd}. \quad (10)$$

Equation (10) is the classical formula for vertex correction of pure sphere power, thus demonstrating that vertex correction can be effectively used in wavefront analysis.

(ii) Cylinder

In another example for astigmatism, $W(r,\theta) = c_2^{-2}\sqrt{6}r^2 \sin 2\theta + c_2^2 \sqrt{6} r^2 \cos 2\theta$ corresponds to the wavefront at the second plane, a similar approach can be used to obtain the curvature of the corrected wavefront as $$\frac{\partial^2 W'}{\partial r^2} = (2\sqrt{6}\, c_2^{-2}\sin 2\theta + 2\sqrt{6}\, c_2^2 \cos 2\theta)\frac{f}{f+d} = \frac{\partial^2 W}{\partial r^2}\frac{f}{f+d}. \quad (11)$$

Denoting P' and P as the curvatures of W' (converted wavefront) and W (measured wavefront) respectively, $$P' = P\frac{f}{f+d} = \frac{P}{1+Pd}. \quad (12)$$

By replacing P with S+C, it is possible to obtain the classical vertex correction for cylinder $$C' = \frac{S+C}{1+d(S+C)} - S'. \quad (13)$$

(iii) Coma

In addition to the low order wavefront vertex corrections discussed above, it is also possible to use vertex correction with wavefront measurements that include high order aberrations. For example, horizontal coma can be expressed as $W(r,\theta) = \sqrt{8}\, c_3^1 (3r^3 - 2r)\cos\theta$, again corresponding to the wavefront at the second plane. With an approach similar to that described above, it is possible to calculate the derivatives to x and to y and then calculate the curvature to r as $$\frac{\partial^2 W'}{\partial r^2} = \frac{f}{f+d} 18\sqrt{8}\, c_3^1 x = \frac{\partial^2 W}{\partial r^2}\frac{f}{f+d}. \quad (14)$$

Denoting P' and P as the curvatures of W' (converted wavefront) and W (measured wavefront) respectively, $$P' = P\frac{f}{f+d} = \frac{P}{1+Pd}. \quad (15)$$

(iv) Spherical Aberrations

In another example, a spherical aberration can be expressed as $W(r) = \sqrt{5}\, c_4^0 (6r^4 - 6r^2 + 1)$. Again, with an approach similar to that described above, it is possible to calculate the derivatives to x and to y and then calculate the curvature to r to determine the curvature of the corrected wavefront as $$\frac{\partial^2 W'}{\partial r^2} = \frac{f}{f+d}(72r^2 - 12)\sqrt{5}\, c_4^0 = \frac{\partial^2 W}{\partial r^2}\frac{f}{f+d}. \quad (16)$$

Denoting P' and P as the curvatures of W' (converted wavefront) and W (measured wavefront) respectively, $$P' = P\frac{f}{f+d} = \frac{P}{1+Pd}. \quad (17)$$

Therefore, for low order aberrations as well as for high order aberrations, it can be shown that by means of a slope scaling as applied in wavefront, it is possible to achieve the effect of power change as defined in a classical sense. Such approaches can be useful in determining treatment surface aberrations based on measurement surface aberrations.

2. New Algorithm for Vertex Correction

Treatment surface aberrations can also be determined based on various algorithmic approaches. In some embodiments, the treatment surface aberration is a treatment surface wavefront map. The treatment surface wavefront map can be derived at least in part by local slope scaling of a measurement surface wavefront map. For example, a treatment surface wavefront map can be derived at least in part by applying a scaling factor of $1/(1+Pd)$ to a slope of a measurement surface wavefront map, where P represents a local curvature of the measurement surface wavefront map and d represents a difference between a measurement surface and a treatment surface. For example, P can be based on a second derivative of the measurement surface wavefront map. P can also be based on a pupil radius of the eye. The following examples illustrate algorithmic approaches that incorporate such principles.

a. Constant HOA

This algorithm assumes that the average curvature for low order aberrations (LOA), as manifested by sphere and cylinder power terms, is affected by vertex distance change. High order aberrations (HOA) are considered as local irregularity add-ons to the mean curvature, and are not affected by vertex distance change. Thus, a total wavefront map can be separated into low order and high order portions as shown by the following formula $$W(x,y) = W_L(x,y) + W_H(x,y). \quad (18)$$

For the low order portion, it is possible to obtain the sphere and cylinder power terms by means of a Zernike decomposition method $$[S,C] = ZD[W_L(x,y)], \quad (19)$$

where S and C represent the sphere and cylinder power terms, respectively, and ZD represents a Zernike decomposition operator. The vertex corrected sphere S' and cylinder C' power terms can be obtained from the following formulae $$S' = \frac{S}{1+dS}, \quad (20)$$

$$C' = \frac{S+C}{1+d(S+C)} - S'. \quad (21)$$

The vertex corrected wavefront can then be obtained by adding the uncorrected high order portion of the original wavefront with the Zernike expansion operator applied to the corrected sphere S' and cylinder C' as $$W'(x,y) = ZE(S',C') + W_H(x,y), \quad (22)$$

where ZE stands for a Zernike expansion operator.

b. Varying HOA

This algorithm segments the wavefront measurement into multiple portions, and is designed to have each portion of the corrected wavefront focused on or toward the focal point of the optical system, regardless of the wavefront shape. Thus, the local slope of each portion of the wavefront measurement can be scaled by a factor of $f/(f+d)$ where f represents the local focal length and d represents the vertex distance. By applying the following algorithms, it is possible to obtain the vertex corrected wavefront:

1. Calculate x- and y-gradient by the following algorithm:
   Along the x axis:
   a. $\partial W/\partial x = [W(i,j+1) - W(i,j)]/dx$ if $[i,j]$ lands on left edge
   b. $\partial W/\partial x = [W(i,j) - W(i,j-1)]/dx$ if $[i,j]$ lands on right edge
   c. $\partial W/\partial x = [W(i,j+1) - W(i,j-1)]/2dx$ otherwise within pupil
   Along the y axis:
   d. $\partial W/\partial y = [W(i,j) - W(i+1,j)]/dy$ if $[i,j]$ lands on upper edge
   e. $\partial W/\partial y = [W(i-1,j) - W(i,j)]/dy$ if $[i,j]$ lands on lower edge
   f. $\partial W/\partial y = [W(i-1,j) - W(i+1,j)]/2dy$ otherwise within pupil
   If $[i,j]$ is outside the pupil, the data is not considered.

2. Calculate local curvature P using this algorithm:

a. Calculate $\partial^2 W/\partial x^2$, $\partial^2 W/\partial y^2$ and $\partial^2 W/\partial x \partial y$ from $\partial W/\partial x$ and $\partial W/\partial y$ using algorithm 1.

b. $\dfrac{\partial^2 W}{\partial r^2} = \dfrac{x^2}{x^2+y^2} \dfrac{\partial^2 W}{\partial x^2} + \dfrac{2xy}{x^2+y^2} \dfrac{\partial^2 W}{\partial x \partial y} + \dfrac{y^2}{x^2+y^2} \dfrac{\partial^2 W}{\partial y^2}$ c. Calculate local curvature $P = \dfrac{1}{R^2} \dfrac{\partial^2 W}{\partial r^2}$ (R being pupil radius)

3. Scale the wavefront local curvature with this algorithm:

$$\frac{\partial W'}{\partial x} = \frac{1}{1+Pd} \frac{\partial W}{\partial x}$$
   $$\frac{\partial W'}{\partial y} = \frac{1}{1+Pd} \frac{\partial W}{\partial y}$$

4. Reconstruct the corrected wavefront W'(x,y) with this algorithm:
   a. Calculate Fourier transform of $\partial W'/\partial x$ and $\partial W'/\partial y$ to get $c_u$ and $c_v$, respectively.
   b. Multiply u with $c_u$ and v with $c_v$ and divide by $u^2 + v^2$.
   c. Inverse Fourier transform to get W'(x,y).
   d. Calculate $\partial W'/\partial x$ and $\partial W'/\partial y$ using algorithm 1, adjusted with the edge being the entire frame as oppose to pupil edge.
   e. Replace $\partial W'/\partial x$ and $\partial W'/\partial y$ with values from step 3 within the pupil, leave values outside pupil untouched.
   f. Determine if a predefined criteria is met, or if a predetermined number of iterations have been completed. If not, go to step (a) and repeat through step (f).
   g. Provide an estimate of W'(x,y).

A predefined criteria of step (f) could be, for example, the RMS error of the reconstructed wavefront based on a comparison between $W'_i$ and $W'_{i-1}$, in the ith and (i-1)th iterations, respectively. Alternatively, other optical quality gauges may be used. In one embodiment, the predetermined number of iterations in step (f) is 10. As illustrated in the above algorithm, it is possible to derive a treatment surface wavefront map based on an iterative Fourier reconstruction algorithm. Thus the entire algorithm, steps 1 to 4, uses both Fourier reconstruction (step 4) and local slope scaling (step 3).

The theory behind Fourier reconstruction can be described as follows. Suppose wavefront W(x,y) is expanded into Fourier series as $$W(x,y) = \iint c(u,v) \exp[i2\pi(ux+vy)] du dv, \quad (23)$$

where c(u,v) is the expansion coefficient. Taking partial derivative to x and y, respectively in the above equation, provides $$\begin{cases} \dfrac{\partial W(x,y)}{\partial x} = i2\pi \iint uc(u,v) \exp[i2\pi(ux+vy)] du dv \\ \dfrac{\partial W(x,y)}{\partial y} = i2\pi \iint vc(u,v) \exp[i2\pi(ux+vy)] du dv \end{cases} \quad (24)$$

Denoting $c_u$ to be the Fourier transform of x-derivative of W(x,y) and $c_v$ to be the Fourier transform of y-derivative of W(x,y), provides $$\begin{cases} \dfrac{\partial W(x,y)}{\partial x} = \iint c_u(u,v) \exp[i2\pi(ux+vy)] du dv \\ \dfrac{\partial W(x,y)}{\partial y} = \iint c_v(u,v) \exp[i2\pi(ux+vy)] du dv \end{cases} \quad (25)$$

Comparing these two sets of equations, provides $$\begin{cases} c_u(u,v) = i2\pi u c(u,v) \\ c_v(u,v) = i2\pi v c(u,v) \end{cases} \quad (26)$$

Combining these two equations with u multiplied in both sides of the first equation and v multiplied in both sides of the second equation, provides $$uc_u(u,v) + vc_v(u,v) = i2\pi(u^2+v^2)c(u,v). \quad (27)$$

Therefore, the Fourier transform of wavefront can be obtained as $$c(u,v) = -\frac{i[uc_u(u,v) + vc_v(u,v)]}{2\pi(u^2+v^2)} = \\ -\frac{i}{2\pi(u^2+v^2)}\left[ u \iint \frac{\partial W(x,y)}{\partial x} \exp[-i2\pi(ux+vy)] + \\ v \iint \frac{\partial W(x,y)}{\partial y} \exp[-i2\pi(ux+vy)] \right] \quad (28)$$

Hence, taking an inverse Fourier transform, it is possible to obtain the wavefront as $$W(x,y) = \iint c(u,v) \exp[i2\pi(ux+vy)] du dv. \quad (29)$$

III. Refractive Treatment Shape

Once a treatment surface aberration has been derived by a method as described above, it is possible to determine a prescription or a refractive treatment shape based on the treatment surface aberration. For example, a prescription can be derived for ameliorating a vision condition in an eye of a patient. A refractive treatment shape can be determined based on the treatment surface aberration of the eye, and a refractive treatment shape can be embodied in any of a variety of corrective optical devices or procedures, including refractive laser surgery, spectacles, contact lenses, intraocular lenses, and the like.

IV. Example

Evaluating Classical Formulas and New Algorithms

Figure 7A:
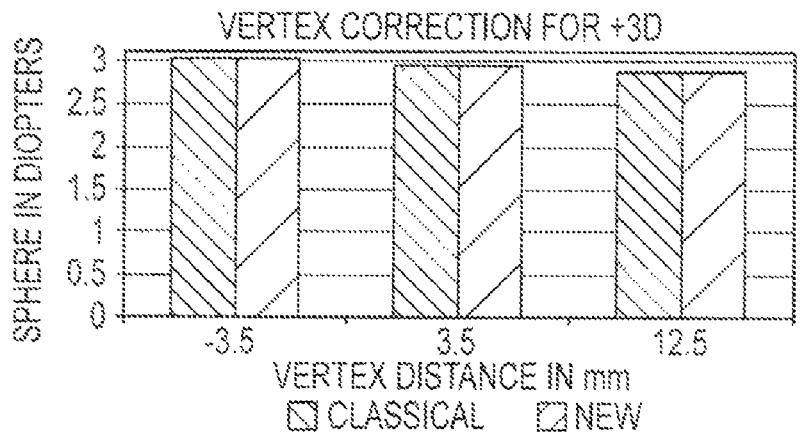
FIGS. 7A, 7B and 7C illustrate a comparison between vertex corrected power calculations based on algorithms provided by the present invention with calculations based on a classical formula according to an embodiment of the present invention.
Figure 7B:
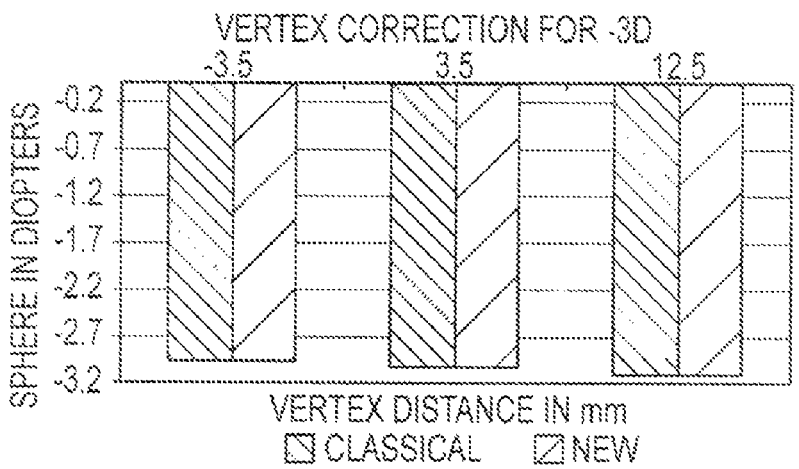
Figure 7C:
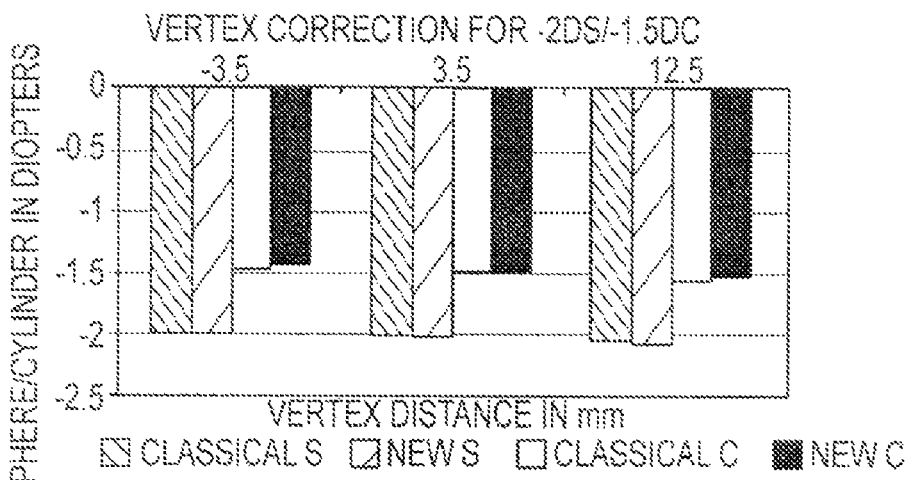

In some embodiments, it is useful to evaluate the convergence of Fourier reconstruction used in the vertex correction algorithms discussed above. Such approaches are discussed in commonly owned patent application Ser. No. 10/601,048 filed Jun. 20, 2003, the entirety of which is hereby incorporated by reference. It is also useful to evaluate the accuracy of the varying high order aberration algorithm as compared to the classical formulas discussed above (i.e. sphere, sphere and cylinder). For example, one test is to show the comparison between the algorithmic approaches and the traditional approaches for myopic, hyperopic, and astigmatism cases. FIG. 7 shows the comparison of vertex corrected sphere and cylinder using the varying high order aberration algorithm described above as compared to classical formulas (i.e. sphere, sphere and cylinder) for (a) hyperopia +3D; (b) myopia −3D; (c) astigmatism −2DS/−1.5DC. It is quite clear that the results are very good. Good results can be shown by a small error. For example, if the difference is less than 0.05D, or smaller than 2.5%, it can generally be considered good. For pure sphere cases (e.g. myopia and hyperopia), the error can be larger, due to coarse sampling of wavefront data in the calculation.

Figure 8:
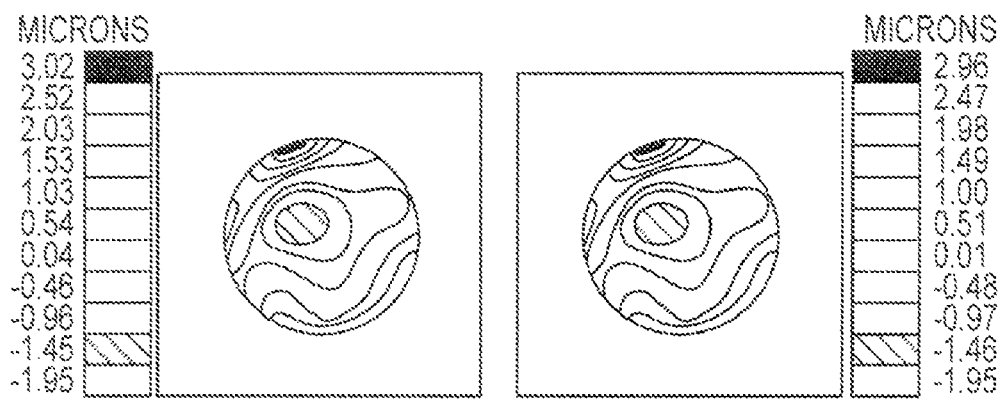
FIG. 8 illustrates a wavefront before and after a vertex correction according to an embodiment of the present invention.

For high order aberrations, it has been shown with two examples (i.e. coma, spherical aberrations) in theory that the vertex corrected wavefront follows the power relationship given by the classical formula of vertex correction. FIG. 8 shows wavefront surface plots of a pre-vertex correction (left panel) and post-vertex correction (right panel) corresponding to a 12.5 mm vertex correction as accomplished by a varying high order aberration algorithm.

In terms of the efficiency of a varying high order aberration algorithm, the following table shows the running time taken for such a vertex correction algorithm with respect to the number of iterations taken in the Fourier reconstruction, corresponding to step 4 of the algorithm, in a 1.13 GHz laptop computer. With 10 iterations, the algorithm can take more than 2 seconds in real time, as shown in Table 1. Fortunately, this vertex correction may only be needed when a treatment table is generated, which in itself may take minutes. Treatment tables are files that can store commands for a laser to deliver individual laser pulses, in the context of a laser ablation treatment. For example, the commands can be for laser pulse duration and size.

TABLE 1

| | Iterations | | | | | | |
|---|---|---|---|---|---|---|---|
| | 1 | 2 | 5 | 10 | 20 | 50 | 200 |
| Time (s) | 0.340 | 0.521 | 1.231 | 2.303 | 4.256 | 10.40 | 41.34 |

Thus in one embodiment, as part of the algorithm, Fourier reconstruction can require about 10 iterations to achieve planned results given by 100-micron sampling rate.

V. Wavefront Propagation from One Plane to Another

In some embodiments, the present invention provides treatment techniques for addressing high order aberrations, including algorithms that can be used to create treatment tables for custom ablation profiles. These techniques can involve the determination of the expected target ablation profile on the curved corneal surface, when the wavefront map is known on the exit pupil plane, which is typically about 3.5 mm below the vertex of the corneal surface. In some cases, embodiments consider the wavefront to propagate as a whole, and do not involve addressing pieces of the wavefront separately. Algorithm embodiments can be validated with a classical vertex correction formula and a wavefront measuring experiment. These high order aberration treatment techniques can be useful in refining or determining shapes such as those used in ophthalmic laser surgery. These techniques can be based on an optical system, a human eye, with total ocular aberrations represented by a wavefront on an exit pupil plane. In ray tracing terminology, this can involve a converging beam with potential aberration deviating from a perfect eye. These deviations can be modeled as wavefront aberrations and be treated using the geometrical theory of aberrations.

A. Formulation of the Wavefront Propagation

Figure 8A:
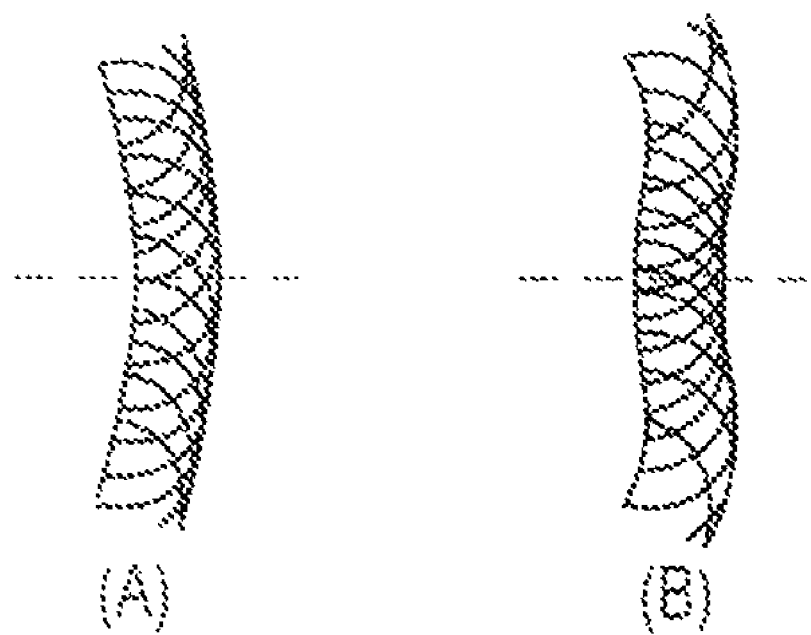
FIG. 8A shows examples of a diverging wavefront and a wavefront with a spherical aberration before and after propagation according to embodiments of the present invention.

As a wavefront propagates, it can be considered as many rays propagating at different directions as determined by the norm of the local wavefront surface. According to the Huygens principle, the new wavefront is the envelope of the spherical wavelets emanating from each point of the original wavefront. FIG. 8A shows examples of a diverging wavefront and a wavefront that includes a spherical aberration before and after propagation according to embodiments of the present invention. Note that the wavefront boundary after propagation has been conformed to a slightly smaller area at the edge as the diffraction effect at the edge is not a concern. In this section, a mathematical formulation is given for such a treatment. Examples of wavefront propagation according to the Huygens principle for FIG. 8A(a) a diverging defocus, and FIG. 8A(b) a spherical aberration are described.

1. Calculation of the Direction Factor

Figure 8B:
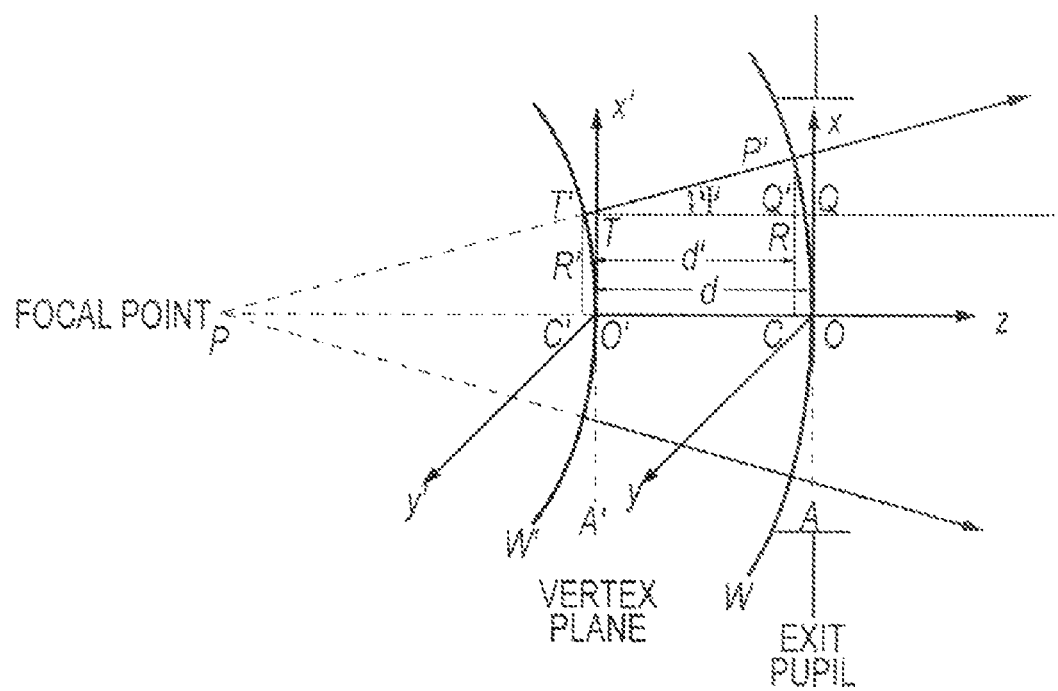
FIG. 8B shows a geometry of a myopic correction as an original wavefront and a propagated wavefront according to embodiments of the present invention.

FIG. 8B shows the geometry of a myopic correction as the original wavefront $W(r, \theta)$ with a radius R propagates a distance d from right to left to become the new wavefront $W'(r', \theta')$ with a new radius $R'$. Thus, a geometry for a myopic wavefront with a radius R propagated a distance d from a less anterior plane towards a more anterior plane to a new wavefront with a radius $R'$ is provided. The reference plane for the original wavefront is S and that for the new wavefront is $S'$. The direction at point T is determined by the angle between the norm of the wavefront at point T and the norm of the reference plane S, or the angle $\psi$. This angle can be calculated from the radial slope of the wavefront as $$\cos\psi = \frac{1}{\sqrt{1 + \left[\frac{\partial W(x, y)}{\partial x}\right]^2 + \left[\frac{\partial W(x, y)}{\partial y}\right]^2}}. \tag{A6}$$

For most applications, the wavefront slope is much smaller than 1. For example, even for a −10 D eye with a 6 mm pupil size, the maximum slope is only 0.03, and its square is 0.0009. Hence, Eq. (A6) can be approximated with a binomial expansion as $$\cos\psi = 1 - \frac{1}{2}\left[\frac{\partial W(x, y)}{\partial x}\right]^2 - \frac{1}{2}\left[\frac{\partial W(x, y)}{\partial y}\right]^2. \tag{A7}$$

Because Zernike polynomials use variables within a unit circle, the new variables $(\rho, \theta)$ in polar coordinates and $(u, v)$ in Cartesian coordinates can be introduced in such a way that $\rho=r/R$ and $u=x/R$, $v=y/R$ so that Eq. (A7) can be written as $$\cos\psi = 1 - \frac{1}{2R^2}a(u, v), \tag{A8}$$

where the direction factor $a(u, v)$ can be written as $$a(u, v) = \left[\frac{\partial W(u, v)}{\partial u}\right]^2 + \left[\frac{\partial W(u, v)}{\partial v}\right]^2. \tag{A9}$$

From FIG. 8B, we have W=Q'Q and W'=T'T. In addition, d=TQ=T'P'. Let d'=T'Q', we obtain $$d'=d\cos\psi. \tag{A10}$$

In addition, we have T'Q=T'T+TQ=W'+d=T'Q'+Q'Q=d'+W. Therefore, $$W' - W = d' - d = d(\cos\psi - 1) = -\frac{d}{2R^2}a(u, v). \tag{A11}$$

Figure 8C:
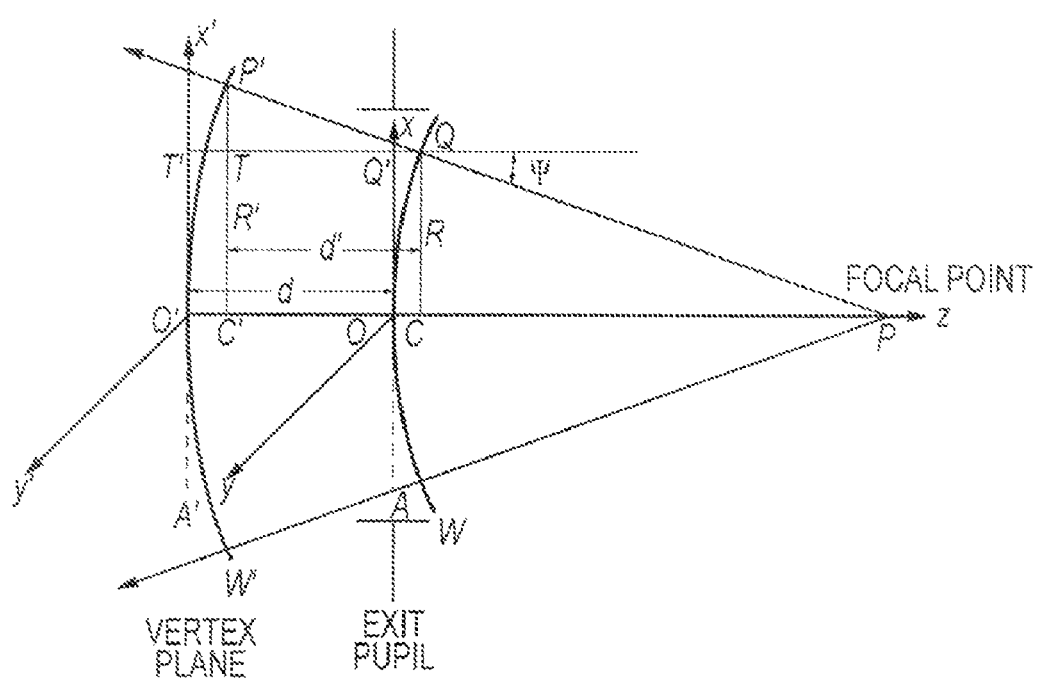
FIG. 8C shows a geometry of a hyperopic wavefront and a corresponding propagated wavefront according to embodiments of the present invention.

The magnitude of the difference in wavefronts can be represented as W'−W. The propagation distance can be represented as d. The direction factor can be represented as a(u,v). R can represent the radius of the original wavefront. Thus, the magnitude of the difference in wavefronts can be proportional to the propagation distance. The magnitude of the difference in wavefronts can also be proportional to the direction factor. Similarly, the magnitude of the difference in wavefronts can be inversely proportional to the square of the wavefront radius or some other boundary dimension (for example the semi-major or semi-minor axis of an ellipse). FIG. 8C shows a geometry for a hyperopic wavefront with a radius R propagated a distance d from a less anterior plane towards a more anterior plane to a new wavefront with a radius $R'$. Because W'>0, W>0 and W'<W for the myopic case, Eq. (A11) is appropriate for representing the propagation of a myopic wavefront. Similarly, for the hyperopic case, as shown in FIG. 8C, we have W=Q'Q and W'=T'T; d=T'Q'=P'Q; and d'=TQ. Therefore, we get T'Q=T'T+TQ=W'+d'=T'Q'+Q'Q=d+W. However, since W'<0, W<0 and |W'|>|W| for a hyperopic case, a negative sign needs to be used for W' and W, or W'+d'=d−W. This gives us $$W' - W = d' - d = d(\cos\psi - 1) = -\frac{d}{2R^2}a(u, v). \tag{A12}$$

which is identical to Eq. (A11). Therefore, Eq. (A11) can be used to represent the propagation of any wavefront. Note that although the magnitude of the propagated wavefront is given by Eq. (A11), it is expressed in the new coordinates $(\rho', \theta')$, not the original coordinates $(\rho, \theta)$, as discussed elsewhere herein. Again, following the previous convention, d is negative when a wavefront is propagated from a more anterior plane to a less anterior plane.

2. Calculation of the Propagated Zernike Coefficients and Wavefront Boundary

As further discussed elsewhere herein, in addition to calculation of the direction factor, the formulation of the wavefront propagation can include calculation of the propagated Zernike coefficients and wavefront boundary. Calculation of the propagated Zernike coefficients can involve the use of Taylor monomials. Calculation of the propagated wavefront boundary can involve a boundary factor.

3. Wavefront Propagation of a Converging Beam

Figure 9:
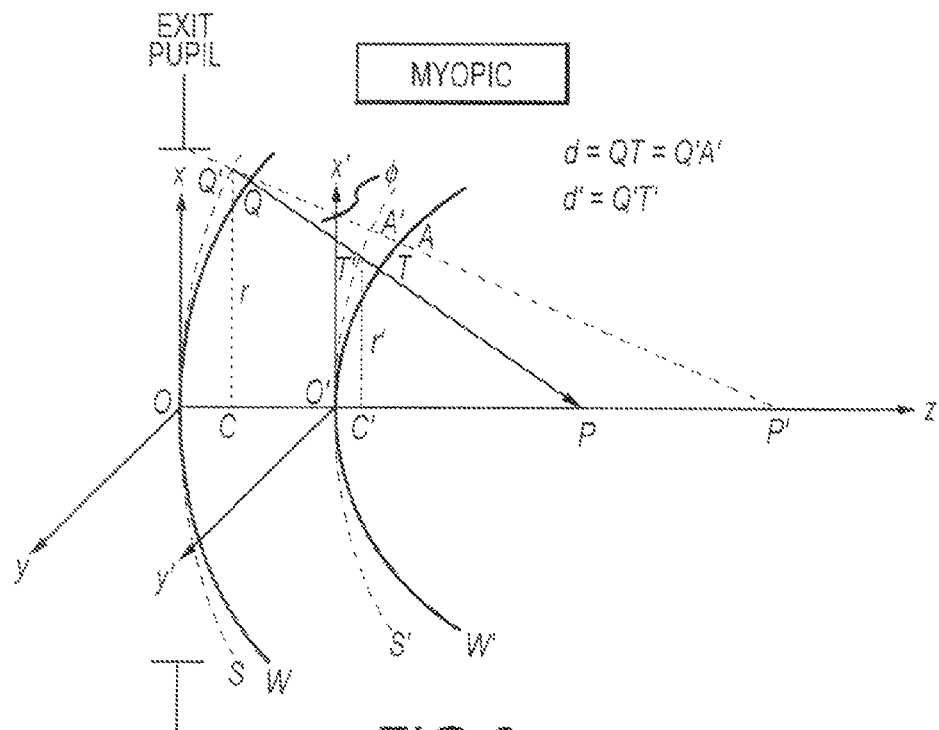
FIG. 9 shows a wavefront coordinate system according to an embodiment of the present invention.

In some embodiments, it can be helpful to consider a known wavefront on the exit pupil plane for a myopic eye, represented by $W(r,\theta)$ in polar coordinates where the optical path length with respect to the reference sphere S is given by Q'Q, as shown in FIG. 9. The propagation of the ray through point Q is normal to the wavefront surface W at point Q. When this ray travels a distance of d, the wavefront becomes $W'(r',\theta')$, because both the magnitude and coordinate system change. The ray may not necessarily travel on the xz plane, although it is shown in FIG. 9 as such. No matter which direction it goes, the ray can still be normal to the new wavefront W' and the new optical path length can be represented by T'T, with respect to the new reference sphere S'. If the angle between the normal of the wavefront W at Q and the normal of the reference sphere S at Q' is $\phi$, we have $$d' = d \cos \phi. \tag{30}$$

FIG. 9 depicts a coordinate system for one point in the original wavefront $W(r,\theta)$ with respect to the reference sphere S propagating to another point in the new wavefront $W'(r',\theta')$ with respect to the new reference sphere S' for a myopic eye, according to some embodiments. From FIG. 9, we obtain $$Q'T = W' + d' = W + d, \tag{31}$$

where d' is the distance of Q'T' and d is the distance of QT and of Q'A'. From Eqs. (30) and (31), we obtain $$W' = W - d(\cos^{-1}\phi - 1). \tag{32}$$

Because the slope of the wavefront can be related to the angle $\phi$ by $$\cos\phi = \frac{1}{\sqrt{1 + \left(\frac{\partial W(r,\theta)}{\partial r}\right)^2}} \approx \frac{1}{1 + \frac{1}{2}\left(\frac{\partial W(r,\theta)}{\partial r}\right)^2}, \tag{33}$$

and the wavefront slope can be much smaller than 1 in some applications, from Eqs. (32) and (33) we obtain $$W'(r',\theta') = W(r,\theta) - \frac{d}{2}\left(\frac{\partial W(r,\theta)}{\partial r}\right)^2 \tag{34}$$

Equation (34) indicates that the propagated wavefront can become smaller for a myopic eye.

Figure 10:
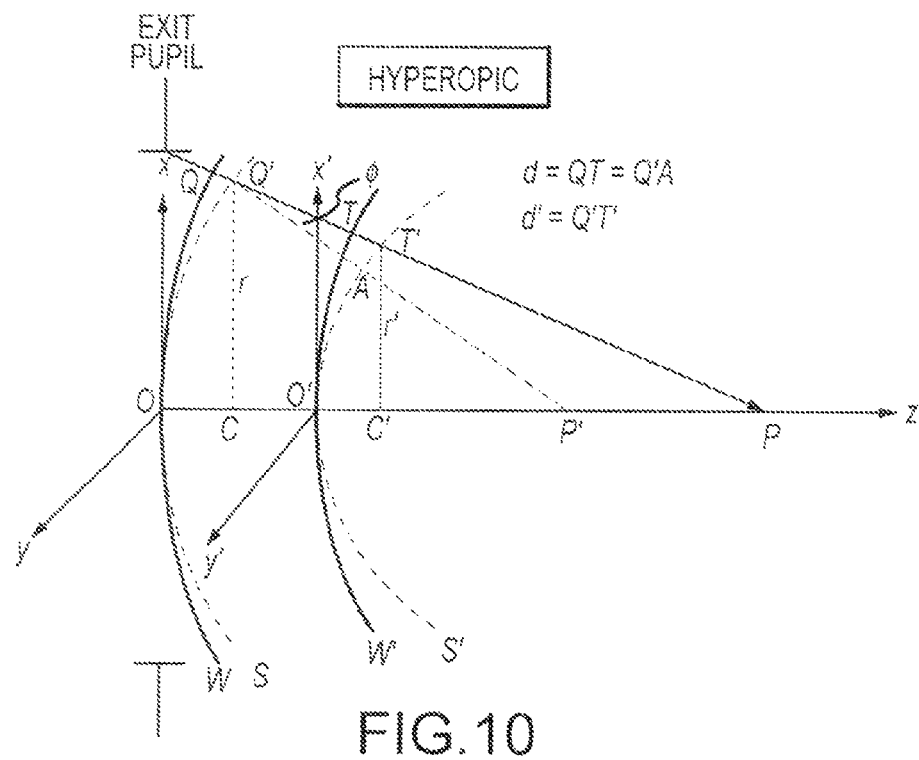
FIG. 10 shows a wavefront coordinate system according to an embodiment of the present invention.

FIG. 10 shows a coordinate system for one point in the original wavefront $W(r,\theta)$ with respect to the reference sphere S propagating to another point in the new wavefront $W'(r',\theta')$ with respect to the new reference sphere S' for a hyperopic eye, according to some embodiments. For a hyperopic eye, as shown in FIG. 10, the following relation can be obtained $$QT' = W' + d = W + d', \tag{35}$$

where d' is the same as in Eq. (30). With similar processing as previously described, we obtain $$W'(r',\theta') = W(r,\theta) + \frac{d}{2}\left(\frac{\partial W(r,\theta)}{\partial r}\right)^2. \tag{36}$$

Equation (36) indicates that for a hyperopic eye, the propagated wavefront can become larger. To simplify the calculation, Eq. (34) can be used for both myopic and hyperopic cases, where −d is used instead of d for hyperopic case. Similarly, for myopic case, if the propagated plane is before the exit pupil plane, such as at spectacle plane, then −d can be used instead of d. For hyperopic eyes where the propagated plane is before the exit pupil plane, d can be used instead of −d. Note Eqs. (34) and (36) can be independent of the focal length of the original converging beam. In human eye case, that means they can be independent of the power of the eye.

The approximation in Eq. (33) can be very small. Assuming a standard eye with total power of 60 D, a 6 mm pupil, the wavefront slope for different amounts of refractive power and the error in Eq. (33) are provided in Table 2.

TABLE 2

| Refractive power (D) | Wavefront slope | Error |
|---|---|---|
| 1 | 0.002988 | 9.96403E−12 |
| 2 | 0.005976 | 1.59468E−10 |
| 3 | 0.008965 | 8.07560E−10 |
| 4 | 0.011955 | 2.55313E−09 |
| 5 | 0.014945 | 6.23540E−09 |
| 6 | 0.017936 | 1.29345E−08 |
| 7 | 0.020928 | 2.39719E−08 |
| 8 | 0.023920 | 4.09115E−08 |
| 9 | 0.026914 | 6.55600E−08 |
| 10 | 0.029908 | 9.99676E−08 |

B. Wavefront Propagation of a Parallel Beam

Figure 11:
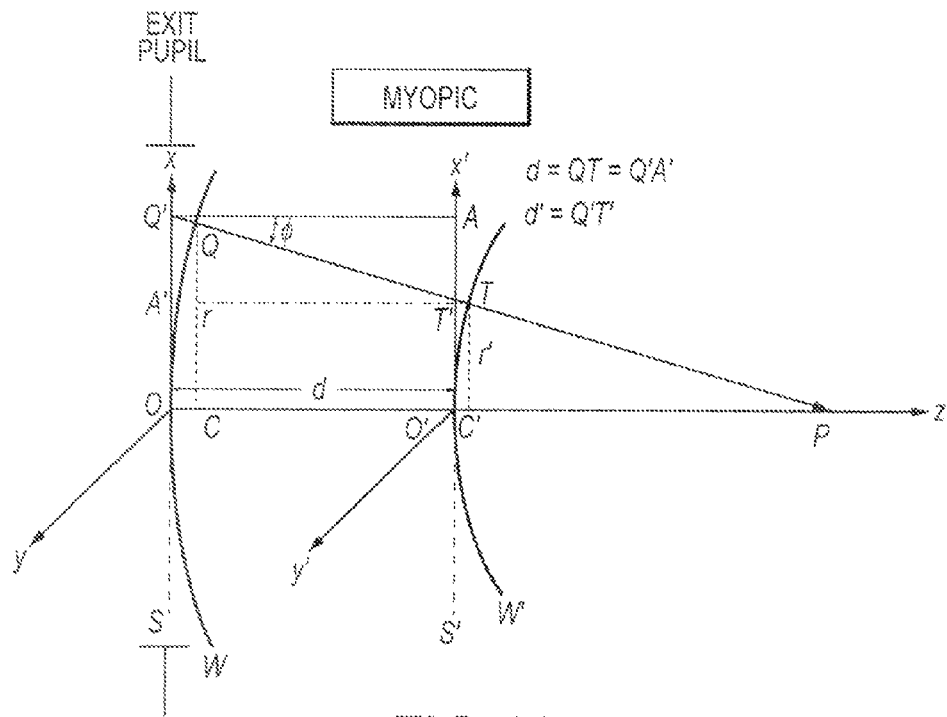
FIG. 11 depicts a wavefront coordinate system according to an embodiment of the present invention.

In some embodiments, it is possible to consider a parallel beam instead of a converging beam, as shown in FIG. 11, which provides a coordinate system for one point in the original wavefront $W(r,\theta)$ with respect to the reference plane S propagating to another point in the new wavefront $W'(r',\theta')$ with respect to the new reference plane S' for a myopic eye. Using a similar approach, we have $$QT' = d - W' = d' - W, \tag{37}$$

which results in the following formula $$W'(r',\theta') = W(r,\theta) - \frac{d}{2}\left(\frac{\partial W(r,\theta)}{\partial r}\right)^2. \tag{38}$$

Figure 12:
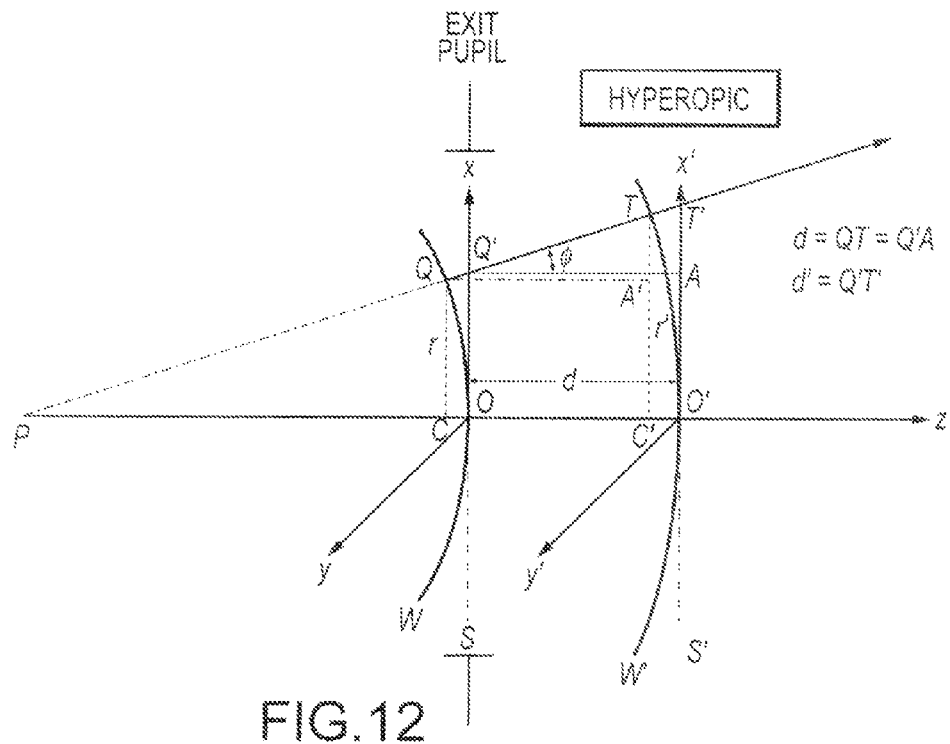
FIG. 12 depicts a wavefront coordinate system according to an embodiment of the present invention.

FIG. 12 provides a coordinate system for one point in the original wavefront $W(r,\theta)$ with respect to the reference plane S propagating to another point in the new wavefront $W'(r',\theta')$ with respect to the new reference plane S' for a hyperopic eye, according to some embodiments. Similarly, for hyperopic eye, as shown in FIG. 12, we can obtain $$W'(r',\theta') = W(r,\theta) + \frac{d}{2}\left(\frac{\partial W(r,\theta)}{\partial r}\right)^2. \tag{39}$$

According to some embodiments of the present invention, the formulae for parallel beams can be the same as those for converging beams. As discussed elsewhere herein, in some cases use of a parallel beam can simplify the treatment of wavefront propagation.

Even though the cornea has a strong curvature, when using a wavefront device it is possible to assume parallel propagation of a wavefront. This may be true even where a patient has myopia or hyperopia, for example.

C. Wavefront Boundary or Size

Figure 12A:
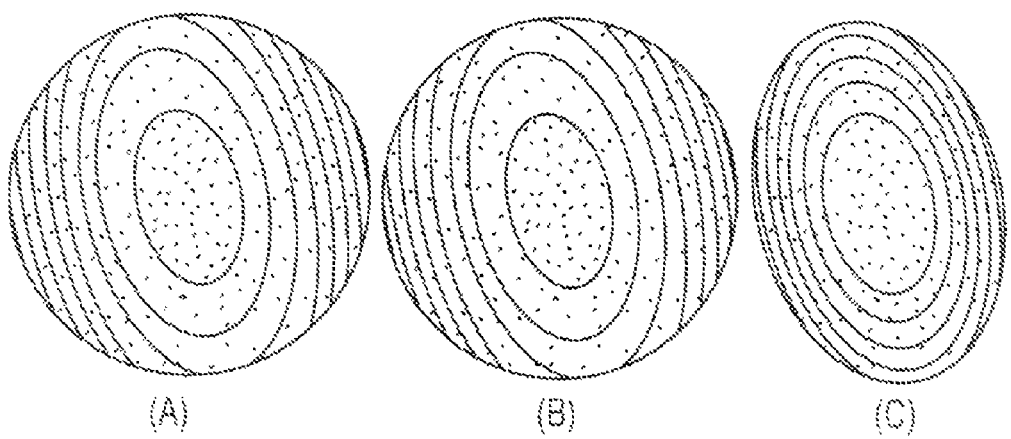
FIG. 12A shows how a wavefront boundary can change when the wavefront propagates, according to embodiments of the present invention.

As noted previously, the wave-front boundary can change when the wavefront propagates. For example, for low order spherocylindrical error, a circular wavefront becomes an elliptical wavefront when it propagates, as shown in FIG. 12A. A low order wavefront ($c_2^{-2}=1$ µm, $c_2^0=3$ µm, $c_2^2=2$ µm, and R=3 mm) propagated to become an elliptical wavefront, is shown in FIG. 12A, where FIG. 12A(a) represents d=35 mm, FIG. 12A(b) represents d=125 mm, and FIG. 12A(c) represents d=120 mm. The aspect ratios of the ellipses are 0.9914, 0.9691, and 0.6638, respectively. In Atchison, D. A. et al., *J. Opt. Soc. Am. A* 20, 965-973 (2003), a subject was investigated that deals with the boundary change from a circular pupil to an elliptical pupil when it is off-axis. Similarly, for a coma wavefront, it also becomes elliptical. For a secondary astigmatism, it becomes bi-elliptical, or a fourfold symmetry. The instant discussion describes an exemplary approach for calculating the propagated wavefront boundary.

From FIG. 8B, the relationship between the original wavefront radius R and the propagated wavefront radius R' can be determined from the simple geometry as $$R' - R = -d\tan\psi = -d\frac{b}{R'}, \tag{A17}$$

where the boundary factor b can be written as $$b = \left[\left(\frac{\partial W(u,v)}{\partial u}\right)^2 + \left(\frac{\partial W(u,v)}{\partial v}\right)^2\right]^{\frac{1}{2}}\bigg|_{\rho=1} = \sqrt{a(u,v)}\bigg|_{\rho=1}. \tag{A18}$$

Therefore, the boundary factor b is the square root of the direction factor at the boundary of the original wavefront (i.e., $\rho=\sqrt{u^2+v^2}=1$). Similarly, from FIG. 8C, we find a similar relationship as $$R' - R = d\tan\psi = -d\frac{b}{R}. \tag{A19}$$

For a converging wavefront, the wavefront radius becomes larger when it propagates backwards, but the defocus coefficient is negative. For a diverging wavefront, the wavefront radius becomes smaller, but the defocus coefficient is positive. Therefore, Eq. (A17) can be used for cases when the signs of Zernike coefficients are correctly applied.

In vision applications, the low order spherocylindrical error is typically much larger than the high order ocular aberrations. Therefore, the influence of the wavefront propagation on the new wavefront boundary for the low order aberrations may be much more significant than that for the high order aberrations.

Dai, G.-m. *J. Opt. Soc. Am. A* 23:1657-1666 (2006) provides a method to define the Zernike polynomials as $$Z_i(\rho,\theta) = \mathfrak{R}_n^{|m|}(\rho)\Phi^m(\theta), \tag{A20}$$

where n and m denote the radial degree and the azimuthal frequency, respectively, the radial polynomials are defined as $$\mathfrak{R}_n^{|m|}(\rho) = \sum_{s=0}^{(n-|m|)/2} \frac{(-1)^s \sqrt{n+1}(n-s)!\rho^{n-2s}}{s![(n+m)/2-s]![(n-m)/2-s]!}, \tag{A21}$$

and the triangular functions as $$\Theta^m(\theta) = \begin{cases} \sqrt{2}\cos|m|\theta & (m>0) \\ 1 & (m=0) \\ \sqrt{2}\sin|m|\theta & (m<0) \end{cases}. \tag{A22}$$

If we represent the direction factor a(u, v) with Zernike polynomials, we may write $$a(u,v) = a(\rho,\theta) = \sum_{i=1}^{J} g_i Z_i(\rho,\theta). \tag{A23}$$

We can separate the radially symmetric terms and the radially asymmetric pairs of terms as $$a(\rho,\theta) = \sum_{n,m} \mathfrak{R}_n^{|m|}(\rho)\sqrt{2}\,(g_n^{-|m|}\sin|m|\theta + g_n^{|m|}\cos|m|\theta) + \tag{A24}$$
$$\sum_n g_n^0 R_n^0(\rho)$$
$$= \sum_{\substack{n,m\\m\neq 0}} \mathfrak{R}_n^{|m|}(\rho)\sqrt{2}\sqrt{(g_n^{-|m|})^2+(g_n^{|m|})^2}\cos|m|\theta - \phi) +$$
$$\sum_n g_n^0 R_n^0(\rho),$$

where the angle of |m|-symmetry $\phi$ can be expressed as $$\phi = \frac{1}{|m|}\tan^{-1}\left(\frac{c_n^{-|m|}}{c_n^{|m|}}\right). \tag{A25}$$

It can be shown (Born, M. et al., Principles of Optics, 7th ed. (Cambridge University Press, 1999)) that $$\mathfrak{R}_n^m(1) = \sqrt{n+1}. \tag{A26}$$

Note that as described herein, in one embodiment an exemplary definition of Zernike radial polynomials can differ from the definition in Born et al. by a factor of $\sqrt{n+1}$.

With the use of Eq. (A24), the boundary factor b can be written as $$b^2 = \tag{A27}$$
$$\sum_n \sqrt{n+1}\,g_n^0 + \sum_{\substack{n,m\\m\neq 0}} \sqrt{2(n+1)}\sqrt{(g_n^{-|m|})^2+(g_n^{|m|})^2}\cos|m|(\theta-\phi).$$

The average of the triangular function of Eq. (A27) is zero. Therefore, as first order approximation, Eq. (A27) can be written as $$b^2 = \sum_n \sqrt{n+1}\, g_n^0. \tag{A28}$$

Hence, the final propagated wavefront has a radius R' as $$R' = R\left(1 - d\frac{b}{R^2}\right). \tag{A29}$$

As described previously, it is possible to use the reference spheres or planes S and S' to determine the optical path length and to assume the wavefront comes from either a converging beam or a parallel beam. In some cases where the wavefront comes from a converging beam, the net effect of the beam size due to the aberrations can be complicated. If the wavefront comes from a parallel beam, however, the net effect of the beam size can be simpler because the beam is parallel and so does not change the beam size. The effective beam size can thus solely be determined by the aberration. In some embodiments, with spectacle correction, a myope may see things smaller and a hyperope may see things larger after the correction. This can be described as minification and magnification effects. From FIG. 11, the right triangle QA'T indicates $$r - r' = d\sin\phi \approx d\tan\phi = d\frac{\partial W(r, \theta)}{\partial r}. \tag{40}$$

Note the approximation in Eq. (40) is good, as the error (tan $\phi$ −sin $\phi$) is small, as can be seen from Table 3.

TABLE 3

| Refractive power (D) | Wavefront slope | Error |
|---|---|---|
| 1 | 0.002988 | 1.33386E−08 |
| 2 | 0.005976 | 1.06706E−07 |
| 3 | 0.008965 | 3.60242E−07 |
| 4 | 0.011955 | 8.54225E−07 |
| 5 | 0.014945 | 1.66873E−06 |
| 6 | 0.017936 | 2.88431E−06 |
| 7 | 0.020928 | 4.58153E−06 |
| 8 | 0.023920 | 6.84017E−06 |
| 9 | 0.026914 | 9.74247E−06 |
| 10 | 0.029908 | 1.33672E−05 |

Equation (40) indicates that for a myopic eye, the wavefront size can become smaller in the propagation direction and the change of the size can be proportional to the propagation distance and the wavefront slope. Similarly, for a hyperopic eye, we have $$r' - r = d\sin\phi \approx d\tan\phi = d\frac{\partial W(r, \theta)}{\partial r}. \tag{41}$$

Now, consider a balanced defocus term, represented with Zernike polynomials as $$W(r, \theta) = c_2^0 Z_2^0(r, \theta) = \sqrt{3}\, c_2^0 \left[2\left(\frac{r}{R}\right)^2 - 1\right], \tag{42}$$

where R is the radius of the aperture on the exit pupil. From Eq. (42) we get $$\frac{\partial W(r, \theta)}{\partial r} = 4\sqrt{3}\, c_2^0 \frac{r}{R^2}, \tag{43}$$

so at the periphery of the wavefront, i.e., r=R, we have $$\left.\frac{\partial W(r, \theta)}{\partial r}\right|_{r=R} = 4\sqrt{3}\, c_2^0 \frac{1}{R}. \tag{44}$$

Substituting Eq. (44) into (40) for the periphery of the wavefront, we have $$R' = R - d\frac{\partial W(r, \theta)}{\partial r} = R\left(1 - d\frac{4\sqrt{3}\, c_2^0}{R^2}\right). \tag{45}$$

Similarly, for a hyperopic eye, we have $$R' = R + d\frac{\partial W(r, \theta)}{\partial r} = R\left(1 + d\frac{4\sqrt{3}\, c_2^0}{R^2}\right). \tag{46}$$

Again, we can just use Eq. (45) for both cases where for a hyperopic eye, −d is used instead of d.

D. Sphere

It is possible to show that the combination of Eqs. (38) and (41) for a pure defocus can give the same formula as the classical vertex correction formula $$S' = \frac{S}{1 + Sd}, \tag{47}$$

where S' and S are in diopters and d in meters. Substituting Eq. (42) into (38), we have $$W'(r', \theta') = c_2^0 \left[1 - d\frac{4\sqrt{3}\, c_2^0}{R^2}\right]\sqrt{3}\left[2\left(\frac{r}{R}\right)^2 - 1\right]. \tag{48}$$

From Eqs. (37), (39), and (41), we know $$\frac{r'}{R'} = \frac{r}{R}. \tag{49}$$

Substituting Eq. (49) into (48), we obtain $$W'(r', \theta') = c_2^0 \left[1 - d\frac{4\sqrt{3}\, c_2^0}{R^2}\right]\sqrt{3}\left[2\left(\frac{r'}{R'}\right)^2 - 1\right] - \frac{12d(c_2^0)^2}{R^2}. \tag{50}$$

If we use the normalized radial variable $$\rho = \frac{r}{R},$$
$$\rho' = \frac{r'}{R'}. \tag{51}$$

we can rewrite Eqs. (38) and (50) as $$W(\rho, \theta) = c_2^0 Z_2^0(\rho, \theta) = \sqrt{3}\, c_2^0 (2\rho^2 - 1), \tag{52}$$

$$W'(\rho', \theta') = \sqrt{3}\, b_2^0 (2\rho'^2 - 1) + b_0^0, \tag{53}$$

where $$b_2^0 = c_2^0 \left[1 - d\frac{4\sqrt{3}\, c_2^0}{R^2}\right], \tag{54}$$

$$b_0^0 = -\frac{12 d (c_2^0)^2}{R^2}. \tag{55}$$

In some cases, the induced piston term does not have any significance on image quality and can be ignored. In addition, it may be very small. From the definition of wavefront refractions $$S = -\frac{4\sqrt{3}\, c_2^0}{R^2}, \tag{56}$$

$$S' = -\frac{4\sqrt{3}\, b_2^0}{R'^2}. \tag{57}$$

Substituting Eq. (55) into Eq. (56) and performing certain arithmetic operations, we get $$S' = \frac{S}{1 + Sd}. \tag{58}$$

E. Sphere and Cylinder

It is possible to show that the combination of Eqs. (34) and (41) for a pure defocus can give the same formula as the classical vertex correction formula Eq. (58) and $$S' + C' = \frac{S + C}{1 + d(S + C)}, \tag{59}$$

where S', C', S, and S' are in diopters and d in meters. Now the wavefront containing the sphere and cylinder can be represented by Zernike polynomials $Z_3$, $Z_4$, and $Z_5$ as $$W(r, \theta) = c_2^{-2} \sqrt{6} \left(\frac{r}{R}\right)^2 \sin 2\theta + c_2^0 \sqrt{3} \left[2\left(\frac{r}{R}\right)^2 - 1\right] + c_2^2 \sqrt{6} \left(\frac{r}{R}\right)^2 \cos 2\theta. \tag{60}$$

Taking a derivative of $W(r, \theta)$ with respect to x and to y, we obtain $$\frac{\partial W(r, \theta)}{\partial x} = \tag{61}$$
$$2\sqrt{6}\, c_2^{-2} \frac{1}{R}\left(\frac{r}{R}\right)\sin\theta + 4\sqrt{3}\, c_2^0 \frac{1}{R}\left(\frac{r}{R}\right)\cos\theta + 2\sqrt{6}\, c_2^2 \frac{1}{R}\left(\frac{r}{R}\right)\cos\theta,$$

$$\frac{\partial W(r, \theta)}{\partial y} = \tag{62}$$
$$2\sqrt{6}\, c_2^{-2} \frac{1}{R}\left(\frac{r}{R}\right)\cos\theta + 4\sqrt{3}\, c_2^0 \frac{1}{R}\left(\frac{r}{R}\right)\sin\theta - 2\sqrt{6}\, c_2^2 \frac{1}{R}\left(\frac{r}{R}\right)\sin\theta.$$

Therefore, we get Eq. (63), as follows.

$$\left(\frac{\partial W(r,\theta)}{\partial r}\right)^2 = \left(\frac{\partial W(r,\theta)}{\partial x}\right)^2 + \left(\frac{\partial W(r,\theta)}{\partial y}\right)^2 \tag{63}$$

$$= \frac{16\sqrt{3}}{R^2} c_2^{-2} c_2^0 \sqrt{6} \left(\frac{r}{R}\right)^2 \sin 2\theta +$$

$$\frac{4\sqrt{3}}{R^2}\left[(c_2^{-2})^2 + 2(c_2^0)^2 + (c_2^2)^2\right]\sqrt{3}\left[2\left(\frac{r}{R}\right)^2 - 1\right] +$$

$$\frac{16\sqrt{3}}{R^2} c_2^2 c_2^0 \sqrt{6} \left(\frac{r}{R}\right)^2 \cos 2\theta +$$

$$\frac{12}{R^2}\left[(c_2^{-2})^2 + 2(c_2^0)^2 + (c_2^2)^2\right].$$

$$= \frac{4\sqrt{3}}{R^2}\left[(c_2^{-2})^2 + 2(c_2^0)^2 + (c_2^2)^2\right]\sqrt{3}\left[2\left(\frac{r}{R}\right)^2 - 1\right] +$$

$$\frac{12}{R^2}\left[(c_2^{-2})^2 + 2(c_2^0)^2 + (c_2^2)^2\right] +$$

$$\frac{16\sqrt{3}}{R^2}\sqrt{(c_2^{-2})^2 + (c_2^2)^2}\, c_2^0 \sqrt{6}\left(\frac{r}{R}\right)^2 \cos 2(\theta - \phi).$$

From Eq. (63), it may be shown that due to the propagation of asymmetric wavefront, the wavefront boundary can become elliptical, for the wavefront slopes at different meridian can be different. The maximum and minimum wavefront slopes can be obtained by setting cos $2(\theta-\phi)$ to 1 and −1 and r=R, or $$\left.\frac{\partial W(r,\theta)}{\partial r}\right|_{r=R} = \frac{1}{R}\left[4\sqrt{3}\, c_2^0 \pm 2\sqrt{6}\sqrt{(c_2^{-2})^2 + (c_2^2)^2}\right]. \tag{64}$$

So the maximum and minimum wavefront radius can be calculated from Eq. (45) as $$R' = R\left[1 - \frac{d}{R}\left(4\sqrt{3}\, c_2^0 \mp 2\sqrt{6}\sqrt{(c_2^{-2})^2 + (c_2^2)^2}\right)\right]. \tag{65}$$

From Eqs. (37), (39), and (41), we know $$\frac{r'}{R'} = \frac{r}{R}. \tag{66}$$

With no rotation, we have $$\theta' = \theta. \tag{67}$$

Substituting Eqs. (63)-(67) and (60) into (38), we have $$W'(r', \theta') = b_2^{-2} \sqrt{6}\left(\frac{r'}{R'}\right)^2 \sin 2\theta' + \tag{68}$$
$$b_2^0 \sqrt{3}\left[2\left(\frac{r}{R}\right)^2 - 1\right] + b_2^2 \sqrt{6}\left(\frac{r'}{R'}\right)^2 \cos 2\theta' + b_0^0,$$

where $$b_2^{-2} = c_2^{-2}\left[1 - d\frac{8\sqrt{3}\, c_2^0}{R^2}\right], \tag{69}$$

$$b_2^0 = c_2^0\left[1 - d\frac{2\sqrt{3}\left\{(c_2^{-2})^2 + 2(c_2^0)^2 + (c_2^2)^2\right\}}{c_2^0 R^2}\right], \tag{70}$$

-continued $$b_2^2 = c_2^2 \left[1 - d\frac{8\sqrt{3} c_2^0}{R^2}\right], \quad (71)$$

$$b_0^0 = \frac{12}{R^2}\left[(c_2^{-2})^2 + 2(c_2^0)^2 + (c_2^2)^2\right]. \quad (72)$$

When using Eq. (49) for the wavefront as represented in Eq. (60), it can be found that the new pupil radius may no longer be circular, because of the astigmatism term. For wavefront representation within a circular area, the defocus term can be used, which results in the same formula as Eq. (49) for the new pupil radius. In addition, the piston induced due to the wavefront propagation may not have any imaging consequence. Using a plus cylinder notation, we can rewrite Eqs. (60) and (68) as $$W(r, \theta) = c_2^0 \sqrt{3}\left[2\left(\frac{r}{R}\right)^2 - 1\right] + \sqrt{(c_2^{-2})^2 + (c_2^2)^2}\ \sqrt{6}\left(\frac{r}{R}\right)^2 \cos 2(\theta - \phi), \quad (73)$$

$$W(r', \theta') = \quad (74)$$
$$b_2^0 \sqrt{3}\left[2\left(\frac{r'}{R'}\right)^2 - 1\right] + \sqrt{(b_2^{-2})^2 + (b_2^2)^2}\ \sqrt{6}\left(\frac{r'}{R'}\right)^2 \cos 2(\theta' - \phi'),$$

where $\phi$ and $\phi'$ are the cylinder axis for W and W', respectively, and are given by $$\phi = \frac{1}{2}\tan^{-1}\left(\frac{c_2^{-2}}{c_2^2}\right), \quad (75)$$

$$\phi' = \frac{1}{2}\tan^{-1}\left(\frac{b_2^{-2}}{b_2^2}\right) = \frac{1}{2}\tan^{-1}\left(\frac{c_2^{-2}}{c_2^2}\right) = \phi. \quad (76)$$

Because the refraction is related to the wavefront curvature, the power can be written as $$P(r, \theta) = -\frac{4\sqrt{3} c_2^0}{R^2} - \frac{2\sqrt{6}\sqrt{(c_2^{-2})^2 + (c_2^2)^2}}{R^2} + \quad (77)$$
$$\frac{2\sqrt{6}\sqrt{(c_2^{-2})^2 + (c_2^2)^2}}{R^2}[1 - \cos 2(\theta - \phi)],$$

$$P(r', \theta') = -\frac{4\sqrt{3} b_2^0}{R'^2} - \frac{2\sqrt{6}\sqrt{(b_2^{-2})^2 + (b_2^2)^2}}{R'^2} + \quad (78)$$
$$\frac{2\sqrt{6}\sqrt{(b_2^{-2})^2 + (b_2^2)^2}}{R'^2}[1 - \cos 2(\theta' - \phi')].$$

Hence, the sphere and cylinder are $$C = \frac{4\sqrt{6}\sqrt{(c_2^{-2})^2 + (c_2^2)^2}}{R^2}, \quad (79)$$

$$S = -\frac{4\sqrt{3} c_2^0}{R^2} - \frac{2\sqrt{6}\sqrt{(c_2^{-2})^2 + (c_2^2)^2}}{R^2}, \quad (80)$$

$$C' = \frac{4\sqrt{6}\sqrt{(b_2^{-2})^2 + (b_2^2)^2}}{R'^2}, \quad (81)$$

$$S' = -\frac{4\sqrt{3} b_2^0}{R'^2} - \frac{2\sqrt{6}\sqrt{(b_2^{-2})^2 + (b_2^2)^2}}{R'^2}. \quad (82)$$

When we consider the minimum power (or sphere only), the new wavefront radius from Eq. (65) can be written as $$R' = R\left[1 - \frac{d}{R^2}\left(4\sqrt{3} c_2^0 + 2\sqrt{6}\sqrt{(c_2^{-2})^2 + (c_2^2)^2}\right)\right] = R(1 + dS). \quad (83)$$

Expanding Eq. (82) with some algebra, we get $$S' = -\frac{1}{R'^2}\left[4\sqrt{3} b_2^0 + 2\sqrt{6}\sqrt{(c_2^{-2})^2 + (c_2^2)^2}\right] \quad (84)$$
$$= -\frac{1}{R'^2}\left[\begin{array}{l}4\sqrt{3} c_2^0 + 2\sqrt{6}\sqrt{(c_2^{-2})^2 + (c_2^2)^2} - \\ \frac{d}{R^2}\left(4\sqrt{3} c_2^0 + 2\sqrt{6}\sqrt{(c_2^{-2})^2 + (c_2^2)^2}\right)^2\end{array}\right]$$
$$= -\frac{1}{R^2(1 + dS)^2}[-R^2 S(1 + dS)]$$
$$= \frac{S}{1 + dS}.$$

Similarly, if we consider the maximum power (or sphere plus cylinder), we have the new wavefront radius from Eq. (65) as $$R' = R\left[1 - \frac{d}{R^2}\left(4\sqrt{3} c_2^0 + 2\sqrt{6}\sqrt{(c_2^{-2})^2 + (c_2^2)^2}\right)\right] = R[1 + d(S + C)]. \quad (85)$$

Expanding the sum of Eqs. (81) and (82), we obtain $$S' + C' = -\frac{1}{R'^2}\left[4\sqrt{3} b_2^0 - 2\sqrt{6}\sqrt{(c_2^{-2})^2 + (c_2^2)^2}\right] \quad (86)$$
$$= -\frac{1}{R'^2}\left[\begin{array}{l}4\sqrt{3} c_2^0 - 2\sqrt{6}\sqrt{(c_2^{-2})^2 + (c_2^2)^2} - \\ \frac{d}{R^2}\left(4\sqrt{3} c_2^0 - 2\sqrt{6}\sqrt{(c_2^{-2})^2 + (c_2^2)^2}\right)^2\end{array}\right]$$
$$= -\frac{1}{R^2[1 + d(S + C)]^2}\{-R^2(S + C)[1 + d(S + C)]\}$$
$$= \frac{S + C}{1 + d(S + C)}.$$

Hence Eqs. (58) and (59) can be proven.

F. General Analytical Representation

According to some implementation embodiments of the present invention, it may be helpful to consider the new wavefront radius that is half of the maximum and minimum. In this case, we consider the spherical equivalent as the power, or the new defocus term, so the new wavefront radius can be expressed as $$R' = R\left[1 - d\frac{4\sqrt{3} c_2^0}{R^2}\right]. \quad (87)$$

For ocular aberrations, the defocus term is often the dominant term. Table 4 lists the error in percentage when Eq. (87) is used instead of a standard formula (Plus cylinder notation is used).

TABLE 4

| S (D) | C (D) | d (mm) | Percent Error |
|---|---|---|---|
| −8 | +6 | 3.5 | ±1.07% |
| 0 | +6 | 3.5 | ±1.04% |
| +2 | +4 | 3.5 | ±0.69% |
| −8 | +6 | 16 | ±5.22% |
| +2 | +4 | 16 | ±3.01% |

For a propagation distance of 3.5 mm, that is the distance from the exit pupil plane to the cornea plane, the error in terms of the pupil radius at extreme cylinder case is barely one percent. To the spectacle plane, it becomes somewhat significant, which stands at 5% maximum. Therefore, for the purpose of wavefront propagation from exit pupil plane to the corneal plane, Eq. (87) can be used as an approximation. For ocular aberrations, modal representation with the use of Zernike polynomials is often used as $$W(r,\theta) = \sum_{i=1}^{J} a_i Z_i(r,\theta) = \sum_{n=1}^{N} \sum_{m=-n}^{n} a_n^m R_n^m(r)\Theta^m(\theta), \quad (88)$$

where $a_i$ is the coefficient of the ith polynomials, and the radial polynomials $$R_n^m(r) = \sum_{s=0}^{(n-m)/2} \frac{(-1)^s \sqrt{n+1}\,(n-s)!}{s![(n+m)/2-s]![(n-m)/2-s]!}\left(\frac{r}{R}\right)^{n-2s} \quad (89)$$

and the triangle functions $$\Theta^m(\theta) = \begin{cases} \sqrt{2}\sin m\theta & (m<0) \\ 1 & (m=0) \\ \sqrt{2}\cos m\theta & (m>0) \end{cases} \quad (90)$$

In some cases, the complex representation of wavefront with Zernike polynomials can make it difficult, if not impossible, to calculate the squares of the wavefront slopes. On the other hand, the simple form of Taylor monomials can make it easy to calculate the squares of the wavefront slopes for the calculation of the direction angle $\phi$ as $$\cos^{-1}\phi = 1 + \frac{1}{2R^2}\left(\frac{\partial W(x,y)}{\partial x}\right)^2 + \frac{1}{2R^2}\left(\frac{\partial W(x,y)}{\partial y}\right)^2. \quad (91)$$

If the wavefront is expanded into Taylor monomials, we have $$W(r,\theta) = \sum_{i=1}^{J} \alpha_i T_i(r,\theta) = \sum_{p,q} \frac{\alpha_p^q}{R^p} T_p^q(x,y), \quad (92)$$

where Taylor monomials are defined as $$T_p^q(\rho,\theta) = \rho^p \cos^q\theta \sin^{p-q}\theta = T_p^q(x,y) = x^q y^{p-q}. \quad (93)$$

This simple form makes Eq. (91) representable by a linear combination of Taylor monomials as Eq. (94) as follows.

$$\cos^{-1}\phi = 1 + \frac{1}{2R^2}\sum_{p,q}\sum_{p',q'} \alpha_p^q \alpha_{p'}^{q'} qq' T_{p+p'-2}^{q+q'-2}(x,y) +$$

$$\frac{1}{2R^2}\sum_{p,q}\sum_{p',q'} \alpha_p^q \alpha_{p'}^{q'}(p-q)(p'-q') T_{p+p'-2}^{q+q'}(x,y)$$

$$= 1 + \frac{1}{2R^2}\sum_{i=1}^{J'} \beta_i T_i(x,y).$$

Embodiments of the present invention encompass various techniques that involve the calculation of propagated Zernike coefficients. For example, it is possible to obtain an analytical expression of the direction factor in terms of Zernike polynomials. It may be helpful to use Taylor monomials because a(u, v) can be obtained for a wavefront with Taylor monomials (Dai, G.-m. *J. Opt. Soc. Am. A* 23:2970-2971 (2006)) as $$\left[\frac{\partial W(u,v)}{\partial u}\right]^2 \sum_{p,q}\sum_{p',q'} \alpha_p^q \alpha_{p'}^{q'} qq' T_{p+p'-2}^{q+q'-2}(u,v), \quad (A13a)$$

$$\left[\frac{\partial W(u,v)}{\partial v}\right]^2 \sum_{p,q}\sum_{p',q'} \alpha_p^q \alpha_{p'}^{q'}(p-q)(p'-q') T_{p+p'-2}^{q+q'}(u,v), \quad (13b)$$

where $\alpha_p^q$ is the Taylor coefficient when the wavefront is expanded into Talor monomials as $$W(\rho,\theta) = \sum_{i=1}^{J} \alpha_i T_i(\rho,\theta) \quad (A14)$$

$$= \sum_{p,q} \alpha_p^q \rho^p \cos^q\theta \sin^{p-q}\theta$$

$$= \sum_{p,q} \alpha_p^q u^q v^{p-q},$$

where J is the total number of Taylor monomials in the wavefront expansion. In Eq. (A14), we have used both the single index i and the double index (p, q) for Taylor monomials. Similarly to the indices of Zernike polynomials, p is referred to as the radial order and q the azimuthal frequency (Dai, G.-m. *J. Opt. Soc. Am. A* 23:1657-1666 (2006). From Eqs. (A8), (A13) and (A14), we obtain $$a(u,v) = \sum_{p,q}\sum_{p',q'} \alpha_p^q \alpha_{p'}^{q'} qq' T_{p+p'-2}^{q+q'-2}(u,v) + \quad (A15)$$

$$\sum_{p,q}\sum_{p',q'} \alpha_p^q \alpha_{p'}^{q'}(p-q)(p'-q') T_{p+p'-2}^{q+q'-2}(u,v)$$

$$= \sum_{i=1}^{J'} \beta_i T_i(u,v),$$

where J' is the new number of monomials to be affected by the wavefront propagation and $\beta_i$ is the coefficient of the ith monomial after the propagation. Table 5 shows the conversion table for $\alpha_i$ to $\beta_i$ for J=27 (6th order). It can be shown that the new radial degree n'=2n−2, where n is the original radial degree. For example, if J=27 (6th order), then J'=65 (10th order). Therefore, the new wavefront can be expressed as $$W'(u', v') = W(u, v) - \frac{d}{2R^2} a(u, v) \quad (A16)$$

$$= \sum_{i=1}^{J} \alpha_i T_i(u, v) - \frac{d}{2R^2} \sum_{i=1}^{J'} \beta_i T_i(u, v)$$

$$= \sum_{i=1}^{J'} \left( \alpha_i - \frac{d}{2R^2} \beta_i \right) T_i(u, v),$$

where $\alpha_i=0$ for i>J. With Eq. (A16), the original wavefront can be converted from Zernike polynomials to Taylor monomials (Dai, G.-m. *J. Opt. Soc. Am. A* 23:1657-1666 (2006)), and the wavefront is propagated using Eq. (A16), then it can be converted back to Zernike polynomials. Table 6 shows the direction factor in terms of Zernike coefficients $b_i$ after propagation as a function of the coefficients $c_i$ before propagation. The new wavefront W'(u', v') can be expressed within the new wavefront boundary. For low order aberrations, since the new boundary becomes elliptical, the new elliptical wavefront can be converted to a circular wavefront using the classical vertex correction formula to a given new wavefront radius. For high order aberrations, the wavefront map can be rescaled (Dai, G.-m. *J. Opt. Soc. Am. A* 23:539-543 (2006)) to account for the change of the wavefront radius.

Table 5 relates $\beta$ and $\alpha$. Their relation appears to be non-linear. In some embodiments, Taylor coefficients $\beta_i$ of the direction factor expressed as Taylor coefficients of the original wavefront $\alpha_i$, up to the 10th order.

TABLE 5

| Symbol | Expression |
|---|---|
| $\beta_1$ | $4\alpha_1\alpha_3 + 2\alpha_2\alpha_4$ |
| $\beta_2$ | $2\alpha_1\alpha_4 + 4\alpha_2\alpha_5$ |
| $\beta_3$ | $6\alpha_1\alpha_6 + 2\alpha_2\alpha_7 + 4\alpha_3^2 + \alpha_4^2$ |
| $\beta_4$ | $4\alpha_1\alpha_7 + 4\alpha_2\alpha_8 + 4\alpha_3\alpha_4 + 4\alpha_4\alpha_5$ |
| $\beta_5$ | $2\alpha_1\alpha_8 + 6\alpha_2\alpha_9 + \alpha_4^2 + 4\alpha_5^2$ |
| $\beta_6$ | $8\alpha_1\alpha_{10} + 2\alpha_2\alpha_{11} + 12\alpha_3\alpha_6 + 2\alpha_4\alpha_7$ |
| $\beta_7$ | $6\alpha_1\alpha_{11} + 4\alpha_2\alpha_{12} + 8\alpha_3\alpha_7 + 6\alpha_4\alpha_6 + 4\alpha_4\alpha_8 + 4\alpha_5\alpha_7$ |
| $\beta_8$ | $4\alpha_1\alpha_{12} + 6\alpha_2\alpha_{13} + 4\alpha_3\alpha_8 + 4\alpha_4\alpha_7 + 6\alpha_4\alpha_9 + 8\alpha_5\alpha_8$ |
| $\beta_9$ | $2\alpha_1\alpha_{13} + 8\alpha_2\alpha_{14} + 2\alpha_4\alpha_8 + 12\alpha_5\alpha_9$ |
| $\beta_{10}$ | $10\alpha_1\alpha_{15} + 2\alpha_2\alpha_{16} + 16\alpha_3\alpha_{10} + 2\alpha_4\alpha_{11} + 9\alpha_6^2 + \alpha_7^2$ |
| $\beta_{11}$ | $8\alpha_1\alpha_{16} + 4\alpha_2\alpha_{17} + 12\alpha_3\alpha_{11} + 8\alpha_4\alpha_{10} + 4\alpha_4\alpha_{12} + 4\alpha_5\alpha_{11} + 12\alpha_6\alpha_7 + 4\alpha_7\alpha_8$ |
| $\beta_{12}$ | $6\alpha_1\alpha_{17} + 6\alpha_2\alpha_{18} + 8\alpha_3\alpha_{12} + 6\alpha_4\alpha_{11} + 6\alpha_4\alpha_{13} + 8\alpha_5\alpha_{12} + 6\alpha_6\alpha_8 + 4\alpha_7^2 + 6\alpha_7\alpha_9 + 4\alpha_8^2$ |
| $\beta_{13}$ | $4\alpha_1\alpha_{18} + 8\alpha_2\alpha_{19} + 4\alpha_3\alpha_{13} + 4\alpha_4\alpha_{12} + 8\alpha_4\alpha_{14} + 12\alpha_5\alpha_{13} + 4\alpha_7\alpha_8 + 12\alpha_8\alpha_9$ |
| $\beta_{14}$ | $2\alpha_1\alpha_{19} + 10\alpha_2\alpha_{20} + 2\alpha_4\alpha_{13} + 16\alpha_5\alpha_{14} + \alpha_8^2 + 9\alpha_9^2$ |
| $\beta_{15}$ | $12\alpha_1\alpha_{21} + 2\alpha_2\alpha_{22} + 20\alpha_3\alpha_{15} + 2\alpha_4\alpha_{16} + 24\alpha_6\alpha_{10} + 2\alpha_7\alpha_{11}$ |
| $\beta_{16}$ | $10\alpha_1\alpha_{22} + 4\alpha_2\alpha_{23} + 16\alpha_3\alpha_{16} + 10\alpha_4\alpha_{15} + 4\alpha_4\alpha_{17} + 4\alpha_5\alpha_{16} + 18\alpha_6\alpha_{11} + 16\alpha_7\alpha_{10} + 4\alpha_7\alpha_{12} + 4\alpha_8\alpha_{11}$ |
| $\beta_{17}$ | $8\alpha_1\alpha_{23} + 6\alpha_2\alpha_{24} + 12\alpha_3\alpha_{17} + 8\alpha_4\alpha_{16} + 6\alpha_4\alpha_{18} + 8\alpha_5\alpha_{17} + 12\alpha_6\alpha_{12} + 12\alpha_7\alpha_{11} + 6\alpha_7\alpha_{13} + 8\alpha_8\alpha_{10} + 8\alpha_8\alpha_{12} + 6\alpha_9\alpha_{11}$ |
| $\beta_{18}$ | $6\alpha_1\alpha_{24} + 8\alpha_2\alpha_{25} + 8\alpha_3\alpha_{18} + 6\alpha_4\alpha_{17} + 8\alpha_4\alpha_{19} + 12\alpha_5\alpha_{18} + 6\alpha_6\alpha_{13} + 8\alpha_7\alpha_{12} + 8\alpha_7\alpha_{14} + 6\alpha_8\alpha_{11} + 12\alpha_8\alpha_{13} + 6\alpha_9\alpha_{12}$ |
| $\beta_{19}$ | $4\alpha_1\alpha_{25} + 10\alpha_2\alpha_{26} + 4\alpha_3\alpha_{19} + 4\alpha_4\alpha_{18} + 10\alpha_4\alpha_{20} + 16\alpha_5\alpha_{19} + 4\alpha_7\alpha_{13} + 4\alpha_8\alpha_{12} + 16\alpha_8\alpha_{14} + 18\alpha_9\alpha_{13}$ |
| $\beta_{20}$ | $2\alpha_1\alpha_{26} + 12\alpha_2\alpha_{27} + 2\alpha_4\alpha_{19} + 20\alpha_5\alpha_{20} + 2\alpha_8\alpha_{13} + 24\alpha_9\alpha_{14}$ |
| $\beta_{21}$ | $14\alpha_1\alpha_{28} + 24\alpha_3\alpha_{21} + 2\alpha_4\alpha_{22} + 30\alpha_6\alpha_{15} + 2\alpha_7\alpha_{16} + 16\alpha_{10}^2 + \alpha_{11}^2$ |
| $\beta_{22}$ | $20\alpha_1\alpha_{22} + 12\alpha_4\alpha_{21} + 4\alpha_4\alpha_{23} + 4\alpha_5\alpha_{22} + 24\alpha_6\alpha_{16} + 20\alpha_7\alpha_{15} + 4\alpha_7\alpha_{17} + 4\alpha_8\alpha_{16} + 24\alpha_{10}\alpha_{11} + 4\alpha_{11}\alpha_{12}$ |
| $\beta_{23}$ | $16\alpha_3\alpha_{23} + 10\alpha_4\alpha_{22} + 6\alpha_4\alpha_{24} + 8\alpha_5\alpha_{23} + 18\alpha_6\alpha_{17} + 16\alpha_7\alpha_{16} + 6\alpha_7\alpha_{18} + 10\alpha_8\alpha_{15} + 8\alpha_8\alpha_{17} + 6\alpha_9\alpha_{16} + 16\alpha_{10}\alpha_{12} + 9\alpha_{11}^2 + 6\alpha_{11}\alpha_{13} + 4\alpha_{12}^2$ |
| $\beta_{24}$ | $12\alpha_3\alpha_{24} + 8\alpha_4\alpha_{23} + 8\alpha_4\alpha_{25} + 12\alpha_5\alpha_{24} + 12\alpha_6\alpha_{18} + 12\alpha_7\alpha_{17} + 8\alpha_7\alpha_{19} + 8\alpha_8\alpha_{16} + 12\alpha_8\alpha_{18} + 12\alpha_9\alpha_{17} + 8\alpha_{10}\alpha_{13} + 12\alpha_{11}\alpha_{12} + 8\alpha_{11}\alpha_{14} + 12\alpha_{12}\alpha_{13}$ |
| $\beta_{25}$ | $8\alpha_3\alpha_{25} + 6\alpha_4\alpha_{24} + 10\alpha_4\alpha_{26} + 16\alpha_5\alpha_{25} + 6\alpha_6\alpha_{19} + 8\alpha_7\alpha_{18} + 10\alpha_7\alpha_{20} + 6\alpha_8\alpha_{17} + 16\alpha_8\alpha_{19} + 18\alpha_9\alpha_{18} + 6\alpha_{11}\alpha_{13} + 4\alpha_{12}^2 + 16\alpha_{12}\alpha_{14} + 9\alpha_{13}^2$ |
| $\beta_{26}$ | $4\alpha_3\alpha_{26} + 4\alpha_4\alpha_{25} + 12\alpha_4\alpha_{27} + 20\alpha_5\alpha_{26} + 4\alpha_7\alpha_{19} + 4\alpha_8\alpha_{18} + 20\alpha_8\alpha_{20} + 24\alpha_9\alpha_{19} + 4\alpha_{12}\alpha_{13} + 24\alpha_{13}\alpha_{14}$ |
| $\beta_{27}$ | $2\alpha_4\alpha_{26} + 24\alpha_5\alpha_{27} + 2\alpha_8\alpha_{19} + 30\alpha_9\alpha_{20} + \alpha_{13}^2 + 16\alpha_{14}^2$ |
| $\beta_{28}$ | $28\alpha_3\alpha_{28} + 36\alpha_6\alpha_{21} + 2\alpha_7\alpha_{22} + 40\alpha_{10}\alpha_{15} + 2\alpha_{11}\alpha_{16}$ |
| $\beta_{29}$ | $14\alpha_4\alpha_{28} + 30\alpha_6\alpha_{22} + 24\alpha_7\alpha_{21} + 4\alpha_7\alpha_{23} + 4\alpha_8\alpha_{22} + 32\alpha_{10}\alpha_{16} + 30\alpha_{11}\alpha_{15} + 4\alpha_{11}\alpha_{17} + 4\alpha_{12}\alpha_{16}$ |
| $\beta_{30}$ | $24\alpha_6\alpha_{23} + 20\alpha_7\alpha_{22} + 6\alpha_7\alpha_{24} + 12\alpha_8\alpha_{21} + 8\alpha_8\alpha_{23} + 6\alpha_9\alpha_{22} + 24\alpha_{10}\alpha_{17} + 24\alpha_{11}\alpha_{16} + 6\alpha_{11}\alpha_{18} + 20\alpha_{12}\alpha_{15} + 8\alpha_{12}\alpha_{17} + 6\alpha_{13}\alpha_{16}$ |
| $\beta_{31}$ | $18\alpha_6\alpha_{24} + 16\alpha_7\alpha_{23} + 8\alpha_7\alpha_{25} + 10\alpha_8\alpha_{22} + 12\alpha_8\alpha_{24} + 12\alpha_9\alpha_{23} + 16\alpha_{10}\alpha_{18} + 18\alpha_{11}\alpha_{17} + 8\alpha_{11}\alpha_{19} + 16\alpha_{12}\alpha_{16} + 12\alpha_{12}\alpha_{18} + 10\alpha_{13}\alpha_{15} + 12\alpha_{13}\alpha_{17} + 8\alpha_{14}\alpha_{16}$ |
| $\beta_{32}$ | $12\alpha_6\alpha_{25} + 12\alpha_7\alpha_{24} + 10\alpha_7\alpha_{26} + 8\alpha_8\alpha_{23} + 16\alpha_8\alpha_{25} + 18\alpha_9\alpha_{24} + 8\alpha_{10}\alpha_{19} + 12\alpha_{11}\alpha_{18} + 10\alpha_{11}\alpha_{20} + 12\alpha_{12}\alpha_{17} + 16\alpha_{12}\alpha_{19} + 8\alpha_{13}\alpha_{16} + 18\alpha_{13}\alpha_{18} + 16\alpha_{14}\alpha_{17}$ |
| $\beta_{33}$ | $6\alpha_6\alpha_{26} + 8\alpha_7\alpha_{25} + 12\alpha_7\alpha_{27} + 6\alpha_8\alpha_{24} + 20\alpha_8\alpha_{26} + 24\alpha_9\alpha_{25} + 6\alpha_{11}\alpha_{19} + 8\alpha_{12}\alpha_{18} + 20\alpha_{12}\alpha_{20} + 6\alpha_{13}\alpha_{17} + 24\alpha_{13}\alpha_{19} + 24\alpha_{14}\alpha_{18}$ |
| $\beta_{34}$ | $4\alpha_7\alpha_{26} + 4\alpha_8\alpha_{25} + 24\alpha_8\alpha_{27} + 30\alpha_9\alpha_{26} + 4\alpha_{12}\alpha_{19} + 4\alpha_{13}\alpha_{18} + 30\alpha_{13}\alpha_{20} + 32\alpha_{14}\alpha_{19}$ |
| $\beta_{35}$ | $2\alpha_8\alpha_{26} + 36\alpha_9\alpha_{27} + 2\alpha_{13}\alpha_{19} + 40\alpha_{14}\alpha_{20}$ |
| $\beta_{36}$ | $42\alpha_6\alpha_{28} + 48\alpha_{10}\alpha_{21} + 2\alpha_{11}\alpha_{22} + 25\alpha_{15}^2 + \alpha_{16}^2$ |
| $\beta_{37}$ | $28\alpha_7\alpha_{28} + 40\alpha_{10}\alpha_{22} + 36\alpha_{11}\alpha_{21} + 4\alpha_{11}\alpha_{23} + 4\alpha_{12}\alpha_{22} + 40\alpha_{15}\alpha_{16} + 4\alpha_{16}\alpha_{17}$ |
| $\beta_{38}$ | $14\alpha_8\alpha_{28} + 32\alpha_{10}\alpha_{23} + 30\alpha_{11}\alpha_{22} + 6\alpha_{11}\alpha_{24} + 24\alpha_{12}\alpha_{21} + 8\alpha_{12}\alpha_{23} + 6\alpha_{13}\alpha_{22} + 30\alpha_{15}\alpha_{17} + 16\alpha_{16}^2 + 6\alpha_{16}\alpha_{18} + 4\alpha_{17}^2$ |
| $\beta_{39}$ | $24\alpha_{10}\alpha_{24} + 24\alpha_{11}\alpha_{23} + 8\alpha_{11}\alpha_{25} + 20\alpha_{12}\alpha_{22} + 12\alpha_{12}\alpha_{24} + 12\alpha_{13}\alpha_{21} + 12\alpha_{13}\alpha_{23} + 8\alpha_{14}\alpha_{22} + 20\alpha_{15}\alpha_{18} + 24\alpha_{16}\alpha_{17} + 8\alpha_{16}\alpha_{19} + 12\alpha_{17}\alpha_{18}$ |
| $\beta_{40}$ | $16\alpha_{10}\alpha_{25} + 18\alpha_{11}\alpha_{24} + 10\alpha_{11}\alpha_{26} + 16\alpha_{12}\alpha_{23} + 16\alpha_{12}\alpha_{25} + 10\alpha_{13}\alpha_{22} + 18\alpha_{13}\alpha_{24} + 16\alpha_{14}\alpha_{23} + 10\alpha_{15}\alpha_{19} + 16\alpha_{16}\alpha_{18} + 10\alpha_{16}\alpha_{20} + 9\alpha_{17}^2 + 16\alpha_{17}\alpha_{19} + 9\alpha_{18}^2$ |
| $\beta_{41}$ | $8\alpha_{10}\alpha_{26} + 12\alpha_{11}\alpha_{25} + 12\alpha_{11}\alpha_{27} + 12\alpha_{12}\alpha_{24} + 20\alpha_{12}\alpha_{26} + 8\alpha_{13}\alpha_{23} + 24\alpha_{13}\alpha_{25} + 24\alpha_{14}\alpha_{24} + 8\alpha_{16}\alpha_{19} + 12\alpha_{17}\alpha_{18} + 20\alpha_{17}\alpha_{20} + 24\alpha_{18}\alpha_{19}$ |
| $\beta_{42}$ | $6\alpha_{11}\alpha_{26} + 8\alpha_{12}\alpha_{25} + 24\alpha_{12}\alpha_{27} + 6\alpha_{13}\alpha_{24} + 30\alpha_{13}\alpha_{26} + 32\alpha_{14}\alpha_{25} + 6\alpha_{17}\alpha_{19} + 4\alpha_{18}^2 + 30\alpha_{18}\alpha_{20} + 16\alpha_{19}^2$ |

TABLE 5-continued

| Symbol | Expression |
|---|---|
| $\beta_{43}$ | $4\alpha_{12}\alpha_{26} + 4\alpha_{13}\alpha_{25} + 36\alpha_{13}\alpha_{27} + 40\alpha_{14}\alpha_{26} + 4\alpha_{18}\alpha_{19} + 40\alpha_{19}\alpha_{20}$ |
| $\beta_{44}$ | $2\alpha_{13}\alpha_{26} + 48\alpha_{14}\alpha_{27} + \alpha_{19}^2 + 25\alpha_{20}^2$ |
| $\beta_{45}$ | $56\alpha_{10}\alpha_{28} + 60\alpha_{15}\alpha_{21} + 2\alpha_{16}\alpha_{22}$ |
| $\beta_{46}$ | $42\alpha_{11}\alpha_{28} + 50\alpha_{15}\alpha_{22} + 48\alpha_{16}\alpha_{21} + 4\alpha_{16}\alpha_{23} + 4\alpha_{17}\alpha_{22}$ |
| $\beta_{47}$ | $28\alpha_{12}\alpha_{28} + 40\alpha_{15}\alpha_{23} + 40\alpha_{16}\alpha_{22} + 6\alpha_{16}\alpha_{24} + 36\alpha_{17}\alpha_{21} + 8\alpha_{17}\alpha_{23} + 6\alpha_{18}\alpha_{22}$ |
| $\beta_{48}$ | $14\alpha_{13}\alpha_{28} + 30\alpha_{15}\alpha_{24} + 32\alpha_{16}\alpha_{23} + 8\alpha_{16}\alpha_{25} + 30\alpha_{17}\alpha_{22} + 12\alpha_{17}\alpha_{24} + 24\alpha_{18}\alpha_{21} + 12\alpha_{18}\alpha_{23} + 8\alpha_{19}\alpha_{22}$ |
| $\beta_{49}$ | $20\alpha_{15}\alpha_{25} + 24\alpha_{16}\alpha_{24} + 10\alpha_{16}\alpha_{26} + 24\alpha_{17}\alpha_{23} + 16\alpha_{17}\alpha_{25} + 20\alpha_{18}\alpha_{22} + 18\alpha_{18}\alpha_{24} + 12\alpha_{19}\alpha_{21} + 16\alpha_{19}\alpha_{23} + 10\alpha_{20}\alpha_{22}$ |
| $\beta_{50}$ | $10\alpha_{15}\alpha_{26} + 16\alpha_{16}\alpha_{25} + 12\alpha_{16}\alpha_{27} + 18\alpha_{17}\alpha_{24} + 20\alpha_{17}\alpha_{26} + 16\alpha_{18}\alpha_{23} + 24\alpha_{18}\alpha_{25} + 10\alpha_{19}\alpha_{22} + 24\alpha_{19}\alpha_{24} + 20\alpha_{20}\alpha_{23}$ |
| $\beta_{51}$ | $8\alpha_{16}\alpha_{26} + 12\alpha_{17}\alpha_{25} + 24\alpha_{17}\alpha_{27} + 12\alpha_{18}\alpha_{24} + 30\alpha_{18}\alpha_{26} + 8\alpha_{19}\alpha_{23} + 32\alpha_{19}\alpha_{25} + 30\alpha_{20}\alpha_{24}$ |
| $\beta_{52}$ | $6\alpha_{17}\alpha_{26} + 8\alpha_{18}\alpha_{25} + 36\alpha_{18}\alpha_{27} + 6\alpha_{19}\alpha_{24} + 40\alpha_{19}\alpha_{26} + 40\alpha_{20}\alpha_{25}$ |
| $\beta_{53}$ | $4\alpha_{18}\alpha_{26} + 4\alpha_{19}\alpha_{25} + 48\alpha_{19}\alpha_{27} + 50\alpha_{20}\alpha_{26}$ |
| $\beta_{54}$ | $2\alpha_{19}\alpha_{26} + 60\alpha_{20}\alpha_{27}$ |
| $\beta_{55}$ | $70\alpha_{15}\alpha_{28} + 36\alpha_{21}^2 + \alpha_{22}^2$ |
| $\beta_{56}$ | $56\alpha_{16}\alpha_{28} + 60\alpha_{21}\alpha_{22} + 4\alpha_{22}\alpha_{23}$ |
| $\beta_{57}$ | $42\alpha_{17}\alpha_{28} + 48\alpha_{21}\alpha_{23} + 25\alpha_{22}^2 + 6\alpha_{22}\alpha_{24} + 4\alpha_{23}^2$ |
| $\beta_{58}$ | $28\alpha_{18}\alpha_{28} + 36\alpha_{21}\alpha_{24} + 40\alpha_{22}\alpha_{23} + 8\alpha_{22}\alpha_{25} + 12\alpha_{23}\alpha_{24}$ |
| $\beta_{59}$ | $14\alpha_{19}\alpha_{28} + 24\alpha_{21}\alpha_{25} + 30\alpha_{22}\alpha_{24} + 10\alpha_{22}\alpha_{26} + 16\alpha_{23}^2 + 16\alpha_{23}\alpha_{25} + 9\alpha_{24}^2$ |
| $\beta_{60}$ | $12\alpha_{21}\alpha_{26} + 20\alpha_{22}\alpha_{25} + 12\alpha_{22}\alpha_{27} + 24\alpha_{23}\alpha_{24} + 20\alpha_{23}\alpha_{26} + 24\alpha_{24}\alpha_{25}$ |
| $\beta_{61}$ | $10\alpha_{22}\alpha_{26} + 16\alpha_{23}\alpha_{25} + 24\alpha_{23}\alpha_{27} + 9\alpha_{24}^2 + 30\alpha_{24}\alpha_{26} + 16\alpha_{25}^2$ |
| $\beta_{62}$ | $8\alpha_{23}\alpha_{26} + 12\alpha_{24}\alpha_{25} + 36\alpha_{24}\alpha_{27} + 40\alpha_{25}\alpha_{26}$ |
| $\beta_{63}$ | $6\alpha_{24}\alpha_{26} + 4\alpha_{25}^2 + 48\alpha_{25}\alpha_{27} + 25\alpha_{26}^2$ |
| $\beta_{64}$ | $4\alpha_{25}\alpha_{26} + 60\alpha_{26}\alpha_{27}$ |
| $\beta_{65}$ | $\alpha_{26}^2 + 36\alpha_{27}^2$ |

Note, the relationship of J' and J is as such: in terms of degree p for J, the new degree is p'=2p−2 for J'. For example, if J=27 ($6^{th}$ order), then J'=65 ($10^{th}$ order). Therefore, the new wavefront can be expressed as $$W'(x', y') = W(x, y) - \frac{d}{2R^2}\left[\left(\frac{\partial W(x,y)}{\partial x}\right)^2 + \left(\frac{\partial W(x,y)}{\partial y}\right)^2\right] \quad (95)$$

$$= \sum_{i=1}^{J} \alpha_i T_i(x, y) - \frac{d}{2R^2}\sum_{i=1}^{J'} \beta_i T_i(x, y)$$

$$= \sum_{i=1}^{J'} \left(\alpha_i - \frac{d}{2R^2}\beta_i\right)T_i(x, y)$$

$$= \sum_{i=1}^{J'} t_i T_i(x, y),$$

where the new coefficients $t_i$ is related to the original coefficients $\alpha_i$ and the derived coefficients $\beta_i$ as $$t_i = \alpha_i - \frac{d}{2R^2}\beta_i. \quad (96)$$

Once the derived coefficients $\beta_i$ are calculated, the new coefficients $t_i$ are known. Because Taylor coefficients can be converted to Zernike coefficients as $$c_i = \sum_{j=1}^{J'} C_{ij}^{t2z} t_j \quad (97)$$

the wavefront can be represented as Zernike polynomials as $$W'(\rho', \theta') = \sum_{i=1}^{J'} c_i Z_i(\rho, \theta). \quad (98)$$

Comparison of Eqs. (88) and (92), we can relate the coefficients of $\alpha_i$ and $a_i$ as $$\alpha_i = \sum_{j=1}^{J} C_{ij}^{z2t} a_j \quad (99)$$

Because $c_i$ is a function of $t_i$, $t_i$ is a function of $\alpha_i$ and $\beta_i$, and $\beta_i$ is a function of $\alpha_i$, we reason that $c_i$ can be calculated from $a_i$.

As shown here, Table 6 provides Zernike coefficients $b_i$ of the direction factor expressed as those in the original wavefront $c_i$, up to the 6th order.

TABLE 6

| Symbol | Expression |
|---|---|
| $b_1$ | $4(\sqrt{6}c_2c_3 + c_1(2\sqrt{5}c_{12} - \sqrt{10}c_{13} + 2\sqrt{3}c_4 - \sqrt{6}c_5) + 6\sqrt{5}c_{13}c_6 - 6\sqrt{5}c_{14}c_6 + 4\sqrt{3}c_5c_6 + 14\sqrt{10}c_{12}c_7 - 14\sqrt{5}c_{13}c_7 + 8\sqrt{6}c_4c_7 - 4\sqrt{3}c_5c_7 + 4\sqrt{3}c_3c_8 + \sqrt{5}c_{11}(\sqrt{2}c_2 + 14c_8 - 6c_9) + 6\sqrt{5}c_{10}c_9 - 4\sqrt{3}c_3c_9)$ |
| $b_2$ | $4(\sqrt{10}c_{13}c_2 + c_1(\sqrt{10}c_{11} + \sqrt{6}c_3) + 2\sqrt{3}c_2c_4 + \sqrt{6}c_2c_5 + 6\sqrt{5}c_{10}c_6 + 6\sqrt{5}c_{11}c_6 + 4\sqrt{3}c_3c_6 + 14\sqrt{5}c_{11}c_7 + 4\sqrt{3}c_3c_7 + 14\sqrt{5}c_{13}c_8 + 8\sqrt{6}c_4c_8 + 4\sqrt{3}c_5c_8 + 2\sqrt{5}c_{12}(c_2 + 7\sqrt{2}c_8) + 6\sqrt{5}c_{13}c_9 + 6\sqrt{5}c_{14}c_9 + 4\sqrt{3}c_5c_9)$ |

TABLE 6-continued

| Symbol | Expression |
|---|---|
| $b_3$ | $4(9\sqrt{6}c_{10}c_{13} + 6\sqrt{5}c_{12}c_3 - 3\sqrt{10}c_{14}c_3 + 4\sqrt{3}c_3c_4 + 3c_{11}(14\sqrt{3}c_{12} - 3\sqrt{6}c_{14} + 4\sqrt{5}c_4) + 3\sqrt{10}c_{10}c_5 + 2\sqrt{3}c_2c_6 + 2\sqrt{3}c_2c_7 + 2\sqrt{3}c_1c_8 + 5\sqrt{6}c_6c_8 + 10\sqrt{6}c_7c_8 - 2\sqrt{3}c_1c_9 - 5\sqrt{6}c_7c_9)$ |
| $b_4$ | $4(6\sqrt{3}c_{10}^2 + 15\sqrt{3}c_{11}^2 + 18\sqrt{3}c_{12}^2 + 15\sqrt{3}c_{13}^2 + 6\sqrt{3}c_{14}^2 + 6\sqrt{5}c_{11}c_3 + \sqrt{3}c_3^2 + 12\sqrt{5}c_{12}c_4 + 2\sqrt{3}c_4^2 + 6\sqrt{5}c_{13}c_5 + \sqrt{3}c_5^2 + 3\sqrt{3}c_6^2 + 2\sqrt{6}c_1c_7 + 7\sqrt{3}c_7^2 + 2\sqrt{6}c_2c_8 + 7\sqrt{3}c_8^2 + 3\sqrt{3}c_9^2)$ |
| $b_5$ | $4(9\sqrt{6}c_{10}c_{11} + 42\sqrt{3}c_{12}c_{13} + 9\sqrt{6}c_{13}c_{14} + 3\sqrt{10}c_{10}c_3 + 12\sqrt{5}c_{13}c_4 + 6\sqrt{5}c_{12}c_5 + 3\sqrt{10}c_{14}c_5 + 4\sqrt{3}c_4c_5 + 2\sqrt{3}c_1c_6 - 2\sqrt{3}c_1c_7 + 5\sqrt{6}c_6c_7 - 5\sqrt{6}c_7^2 + 2\sqrt{3}c_2c_8 + 5\sqrt{6}c_8^2 + 2\sqrt{3}c_2c_9 + 5\sqrt{6}c_8c_9)$ |
| $b_6$ | $8\sqrt{5}c_1(c_{13} - c_{14}) + 4(10\sqrt{5}c_{11}c_2 + 54\sqrt{5}c_{12}c_6 + 30\sqrt{3}c_4c_6 + 55\sqrt{10}c_{13}c_7 - 28\sqrt{10}c_{14}c_7 + 15\sqrt{6}c_5c_7 + 55\sqrt{10}c_{11}c_8 + 15\sqrt{6}c_3c_8 + 2\sqrt{5}c_{10}(5c_2 + 14\sqrt{2}c_8))/5$ |
| $b_7$ | $4(10\sqrt{5}c_1(\sqrt{2}c_{12} - c_{13}) + 21\sqrt{10}c_{13}c_6 - 12\sqrt{10}c_{14}c_6 + 5\sqrt{6}c_5c_6 + 86\sqrt{5}c_{12}c_7 - 34\sqrt{10}c_{13}c_7 + 30\sqrt{3}c_4c_7 - 10\sqrt{6}c_5c_7 + 10\sqrt{6}c_3c_8 + \sqrt{5}c_{11}(10c_2 + \sqrt{2}(34c_8 - 21c_9)) + 12\sqrt{10}c_{10}c_9 - 5\sqrt{6}c_3c_9)/5$ |
| $b_8$ | $4(10\sqrt{5}c_1c_{11} + 10\sqrt{5}c_{13}c_2 + 12\sqrt{10}c_{10}c_6 + 21\sqrt{10}c_{11}c_6 + 5\sqrt{6}c_3c_6 + 34\sqrt{10}c_{11}c_7 + 10\sqrt{6}c_3c_7 + 34\sqrt{10}c_{13}c_8 + 30\sqrt{3}c_4c_8 + 10\sqrt{6}c_5c_8 + 2\sqrt{5}c_{12}(5\sqrt{2}c_2 + 43c_8) + 21\sqrt{10}c_{13}c_9 + 12\sqrt{10}c_{14}c_9 + 5\sqrt{6}c_5c_9)/5$ |
| $b_9$ | $8\sqrt{5}c_1(c_{10} - c_{11}) + 4(10\sqrt{5}c_{14}c_2 + 28\sqrt{10}c_{10}c_7 - 55\sqrt{10}c_{11}c_7 - 15\sqrt{6}c_3c_7 + 28\sqrt{10}c_{14}c_8 + 15\sqrt{6}c_5c_8 + 5\sqrt{5}c_{13}(2c_2 + 11\sqrt{2}c_8) + 54\sqrt{5}c_{12}c_9 + 30\sqrt{3}c_4c_9)/5$ |
| $b_{10}$ | $8(10\sqrt{6}_{13}c_3 + 20c_{10}(2\sqrt{5}c_{12} + \sqrt{3}c_4) + 10c_{11}(4\sqrt{10}c_{13} + \sqrt{6}c_5) + 9\sqrt{10}c_6c_8 + 9\sqrt{10}c_7c_9)/5$ |
| $b_{11}$ | $4(30\sqrt{3}c_{12}c_3 - 5\sqrt{6}c_{14}c_3 + 5c_{11}(22\sqrt{5}c_{12} - 5\sqrt{10}c_{14} + 8\sqrt{3}c_4) + 5c_{10}(5\sqrt{10}c_{13} + \sqrt{6}c_5) + 9\sqrt{10}c_6c_8 + 18\sqrt{10}c_7c_8 - 9\sqrt{10}c_7c_9)/5$ |
| $b_{12}$ | $8\sqrt{5}c_{10}^2 + 32\sqrt{5}c_{11}^2 + 48\sqrt{5}c_{12}^2 + 32\sqrt{5}c_{13}^2 + 8\sqrt{5}c_{14}^2 + 16\sqrt{3}c_{11}c_3 + 32\sqrt{3}c_{12}c_4 + 16\sqrt{3}c_{13}c_5 + (12c_6^2)/\sqrt{5} + 12\sqrt{5}c_7^2 + 12\sqrt{5}c_8^2 + (12c_9^2)/\sqrt{5}$ |
| $b_{13}$ | $4(110\sqrt{5}c_{12}c_{13} + 25\sqrt{10}c_{13}c_{14} + 5c_{10}(5\sqrt{10}c_{11} + \sqrt{6}c_3) + 40\sqrt{3}c_{13}c_4 + 30\sqrt{3}_{12}c_5 + 5\sqrt{6}c_{14}c_5 + 9\sqrt{10}c_6c_7 - 9\sqrt{10}c_7^2 + 9\sqrt{10}c_8^2 + 9\sqrt{10}c_8c_9)/5$ |
| $b_{14}$ | $-32\sqrt{10}c_{11}^2 + 32\sqrt{10}c_{13}^2 + 64\sqrt{5}c_{12}c_{14} - 16\sqrt{6}c_{11}c_3 + 32\sqrt{3}c_{14}c_4 + 16\sqrt{6}c_{13}c_5 - 72\sqrt{2/5}c_6c_7 + 72\sqrt{2/5}c_8c_9$ |
| $b_{15}$ | $16\sqrt{15}(c_{13}c_6 + c_{14}c_7 + c_{10}c_8 + c_{11}c_9)$ |
| $b_{16}$ | $16\sqrt{3/5}(3\sqrt{2}c_{12}c_6 + 5c_{13}c_7 - 2c_{14}c_7 + 2c_{10}c_8 + 5c_{11}c_8)$ |
| $b_{17}$ | $8\sqrt{3/5}(3c_{13}c_6 - c_{14}c_6 + 9\sqrt{2}c_{12}c_7 - 7c_{13}c_7 + 7c_{11}c_8 + c_{10}c_9 - 3c_{11}c_9)$ |
| $b_{18}$ | $8\sqrt{3/5}(c_{10}c_6 + 3c_{11}c_6 + 7c_{11}c_7 + 9\sqrt{2}c_{12}c_8 + 7c_{13}c_8 + 3c_{13}c_9 + c_{14}c_9)$ |
| $b_{19}$ | $16\sqrt{3/5}(2c_{10}c_7 - 5c_{11}c_7 + 5c_{13}c_8 + 2c_{14}c_8 + 3\sqrt{2}c_{12}c_9)$ |
| $b_{20}$ | $-16\sqrt{15}(c_{11}c_6 + c_{10}c_7 - c_{14}c_8 - c_{13}c_9)$ |
| $b_{21}$ | $160\sqrt{2/7}(c_{10}c_{13} + \sqrt{2}c_{11}c_{14})$ |
| $b_{22}$ | $160(c_{10}c_{12} + \sqrt{2}c_{11}c_{13})/\sqrt{7}$ |
| $b_{23}$ | $32(8c_{11}c_{12} + \sqrt{2}c_{10}c_{13} - \sqrt{2}c_{11}c_{14})/\sqrt{7}$ |
| $b_{24}$ | $8(c_{10}^2 + 10c_{11}^2 + 18c_{12}^2 + 10c_{13}^2 + c_{14}^2)/\sqrt{7}$ |
| $b_{25}$ | $32(\sqrt{2}c_{10}c_{11} + 8c_{12}c_{13} + \sqrt{2}c_{13}c_{14})/\sqrt{7}$ |
| $b_{26}$ | $-80(\sqrt{2}c_{11}^2 - \sqrt{2}c_{13}^2 - 2c_{12}c_{14})/\sqrt{7}$ |
| $b_{27}$ | $-160\sqrt{2/7}(c_{10}c_{11} - c_{13}c_{14})$ |

Table 7 provides a comparison of Zernike Coefficients, in μm, after a low order wavefront propagated by 3.5 mm or 12.5 mm using the vertex correction method and Zemax®. Both the original and propagated wavefronts are represented over a 6 mm pupil.

TABLE 7

| Cost | Term | Input | Output (d = 3.5 mm) | | | Out (d = 12.5 mm) | | |
|------|------|-------|--------|---------|---------|--------|---------|---------|
|      |      |       | Vertex | Zemax ® | Diff (%) | Vertex | Zemax ® | Diff (%) |
| One | $c_2^{-2}$ | 0.3140 | 0.3086 | 0.3085 | 0.03% | 0.2953 | 0.2944 | 0.30% |
|     | $c_2^{0}$ | -3.2480 | -3.2187 | -3.2181 | 0.02% | -3.1459 | -3.1420 | 0.12% |
|     | $c_2^{2}$ | -0.8630 | -0.8481 | -0.8503 | 0.26% | -0.8115 | -0.8089 | 0.32% |
| Two | $c_2^{-2}$ | -2.2910 | -2.2951 | -2.2950 | 0.00% | -2.3060 | -2.3053 | 0.03% |
|     | $c_2^{0}$ | 0.3250 | 0.3324 | 0.3323 | 0.03% | 0.3516 | 0.3514 | 0.06% |
|     | $c_2^{2}$ | 0.1600 | 0.1603 | 0.1602 | 0.05% | 0.1610 | 0.1610 | 0.00% |

Table 8 provides a comparison of Zernike coefficients, in μm, after a single term wavefront propagated by 12.5 mm using the analytical method and Zemax®. Both the original and propagated wavefronts are represented over a 6 mm pupil.

TABLE 8

| Term | Analytical | Zemax ® |
|------|------------|---------|
| $c_4^0 = 0.5$ μm | | |
| $c_2^0$ | -0.217 | -0.217 |
| $c_4^0$ | 0.4814 | 0.4813 |
| $c_2^0$ | -0.0094 | -0.0096 |
| $c_3^1 = 0.5$ μm | | |
| $c_2^0$ | -0.0084 | -0.0180 |
| $c_2^2$ | -0.0085 | -0.0153 |
| $c_3^1$ | 0.5000 | 0.5000 |
| $c_4^0$ | -0.0047 | -0.0047 |
| $c_4^2$ | -0.0040 | -0.0040 |
| $c_3^3 = 0.5$ μm | | |
| $c_2^0$ | -0.0036 | -0.0036 |
| $c_3^3$ | 0.5000 | 0.5000 |
| $c_4^0$ | -0.0009 | -0.0009 |

Table 9 provides a comparison of Zernike coefficients, in μm, after a random wavefront propagated by 12.5 mm using the analytical method and Zemax®. Both the original and propagated wavefronts are represented over a 6 mm pupil.

TABLE 9

| Term | Input | Output | | |
|------|-------|--------|---|---|
|      |       | Analytical | Zemax ® | Diff |
| $c_2^{-2}$ | -0.0646 | -0.0757 | -0.0795 | -0.0038 |
| $c_2^{0}$ | 3.3435 | 3.4567 | 3.4588 | 0.0021 |
| $c_2^{2}$ | -0.0217 | -0.0230 | -0.0240 | -0.0010 |
| $c_3^{-3}$ | -0.2103 | -0.2222 | -0.2215 | 0.0007 |
| $c_3^{-1}$ | 0.0810 | 0.0855 | 0.0786 | -0.0069 |
| $c_3^{1}$ | 0.0590 | 0.0659 | 0.0763 | 0.0104 |
| $c_3^{3}$ | 0.0047 | 0.0018 | -0.0018 | -0.0036 |
| $c_4^{-4}$ | 0.0451 | 0.0583 | 0.0541 | -0.0042 |
| $c_4^{-2}$ | -0.0538 | -0.0565 | -0.0569 | -0.0042 |
| $c_4^{0}$ | 0.0705 | 0.0732 | 0.0918 | 0.0186 |
| $c_4^{2}$ | 0.1110 | 0.1102 | 0.1236 | 0.0134 |
| $c_4^{4}$ | -0.0477 | -0.0535 | -0.0631 | -0.0096 |
| $c_5^{-5}$ | 0.0169 | 0.0211 | 0.0206 | -0.0005 |
| $c_5^{-3}$ | 0.0276 | 0.0263 | 0.0315 | 0.0052 |
| $c_5^{-1}$ | -0.0296 | -0.0292 | -0.0344 | -0.0052 |
| $c_5^{1}$ | 0.0294 | 0.0315 | 0.0358 | 0.0043 |
| $c_5^{3}$ | -0.0217 | -0.0231 | -0.0257 | -0.0026 |

TABLE 9-continued

| Term | Input | Output | | |
|------|-------|--------|---|---|
|      |       | Analytical | Zemax ® | Diff |
| $c_5^{5}$ | -0.0079 | -0.0067 | -0.0102 | -0.0035 |
| $c_6^{-6}$ | 0.0575 | 0.0601 | 0.0706 | 0.0105 |
| $c_6^{-4}$ | 0.0080 | 0.0111 | 0.0102 | -0.0009 |
| $c_6^{-2}$ | 0.0122 | 0.0123 | 0.0141 | 0.0018 |
| $c_6^{0}$ | 0.0280 | 0.0286 | 0.0340 | 0.0054 |
| $c_6^{2}$ | -0.0093 | -0.0109 | -0.0101 | 0.0008 |
| $c_6^{4}$ | -0.0179 | -0.0190 | -0.0233 | -0.0043 |
| $c_6^{6}$ | -0.0332 | -0.0360 | -0.0405 | -0.0045 |
| r.m.s | 11.2716 | 12.0531 | 12.0785 | 0.0331 |
| ho rms | -0.0879 | 0.0980 | 0.1083 | 0.0320 |

Figure 13:
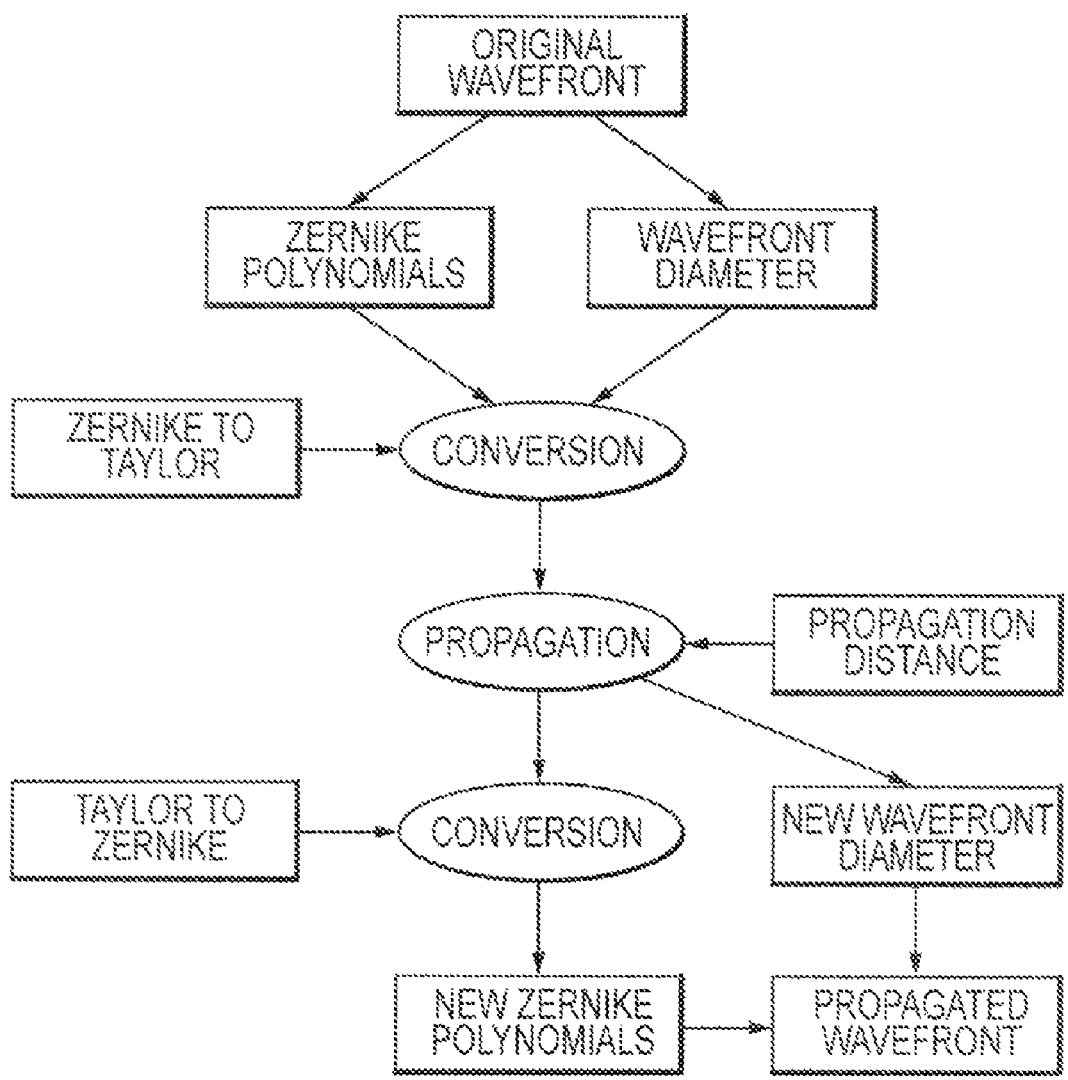
FIG. 13 illustrates a procedural flow chart for analyzing wavefront propagation according to an embodiment of the present invention.

FIG. 13 shows a flow chart for the process for an original wavefront propagated to a certain distance to become a propagated new wavefront, using an analytical approach. The original wavefront is expanded into Zernike polynomials using Eq. (88). The first conversion into Taylor monomials uses Eq. (92), with the conversion matrix given by Eq. (A).

$$C_{z2t} = \frac{(-1)^{(n-q)/2}\sqrt{n+1}\,[(n+p)/2]!\,[m]!}{[(p+|m|)/2]!\,[(n-p)/2]!} \times \sum_{t=0}^{t_0} \sum_{t'=0}^{(p-|m|)/2} \frac{(-1)^t \sqrt{2-\delta_{m0}}\,f(m,t)}{(t')!\,[(p-|m|)/2-t']!}, \quad (A)$$

The propagation is performed with Eq. (96) using the propagation distance d, and the new wavefront diameter is obtained with Eq. (87). The second conversion, which converts Taylor coefficients to Zernike coefficients, is done with Eq. (97) using the conversion matrix from given by Eq. (B). Finally, the new Zernike coefficients and new wavefront diameter are obtained, and the combination gives the new propagated wavefront.

$$C_{t2z} = \frac{1}{\pi} \int_0^1 \int_0^{2\pi} T_p^q(\rho,\theta) Z_n^m(\rho,\theta) d\rho \quad (B)$$

$$= \frac{(p-q)!\,q!}{2^p} \sum_{t=0}^{q} \frac{1}{t!(q-t)!} \sum_{t'=0}^{p-q} \frac{g(p,q,m,t,t')}{(t')!(p-q-t')!} \times$$

$$\sum_{s=0}^{(n-|m|)/2} \frac{(-1)^s \sqrt{n+1} \, (n-s)!}{s![(n+m)/2-s]![(n-m)/2-s]!} \times$$

$$\frac{1}{n+p-2s+2},$$

G. General Numerical Representation

For a pure numerical approach, the original wavefront may be in an analytical form, such as represented as Zernike polynomials or other basis functions. It can be sampled in discrete form, i.e., to obtain values in a 2-D space over the wavefront diameter. If the original wavefront is already discrete, such as from a Fourier reconstruction, we can keep the same discrete data form or we can do a resampling. Calculation of the x and y derivatives can be done by calculating the difference of two neighboring points in either x or y direction, divided by the sampling rate, or the distance between the two neighboring points. To obtain the derivative to r, the following simple formula can be used:

$$\frac{\partial W(r,\theta)}{\partial r} = \sqrt{\left[\frac{\partial W(r,\theta)}{\partial x}\right]^2 + \left[\frac{\partial W(r,\theta)}{\partial y}\right]^2} \quad (100)$$

Figure 14:
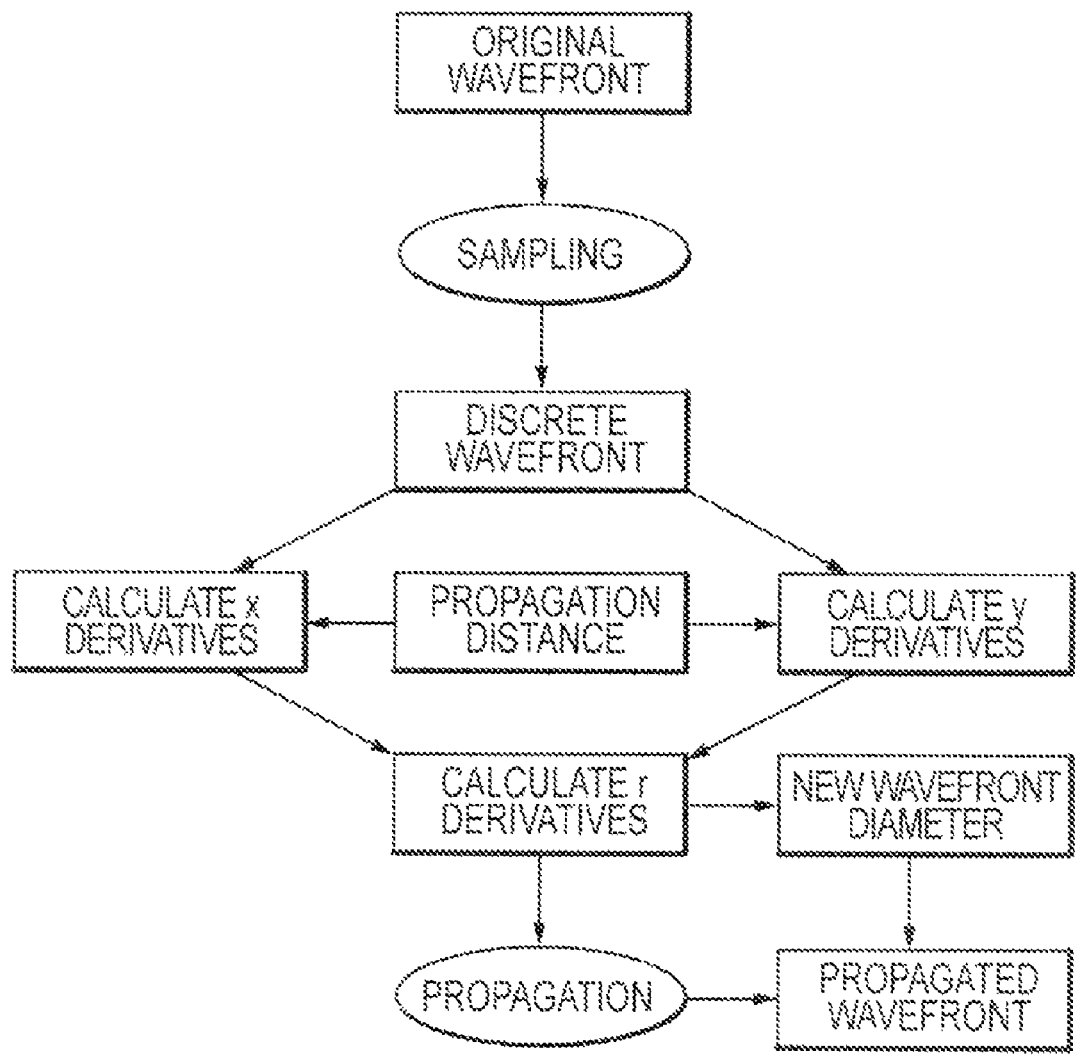
FIG. 14 illustrates a procedural flow chart for analyzing wavefront propagation according to an embodiment of the present invention.

Once the derivative to r is calculated, the new wavefront diameter can be obtained using Eq. (87). The new discrete wavefront can then be obtained with Eq. (38). FIG. 14 illustrates a flow chart for the process of wavefront propagation using numerical approach.

VI. Verification

For low order aberrations, it may be helpful to consider FIG. 5. The simple geometry shows $$\frac{R}{R'} = \frac{f}{f+d} \quad (A30)$$

or $$R' = \left(1 + \frac{d}{f}\right)R. \quad (A31)$$

Using a plus cylinder notation, we first consider the meridian of the minimum power S. Because the focal length is related to the refractive power by f=1/S, we obtain the semiminor axis of the propagated wavefront as $$R_{min} = (1+dS)R \quad (A32)$$

$$= R\left\{1 - \frac{d}{R^2}\left[4\sqrt{3}\,c_2^0 + 2\sqrt{6}\,\sqrt{(c_2^{-2})^2 + (c_2^2)^2}\right]\right\},$$

as the sphere power S is given by Eq. (A56a). Similarly, for the meridian of the maximum power S+C, we have f=1/(S+C). Therefore the semimajor axis of the propagated wavefront is $$R_{max} = [1+d(S+C)]R \quad (A33)$$

$$= R\left\{1 - \frac{d}{R^2}\left[4\sqrt{3}\,c_2^0 - 2\sqrt{6}\,\sqrt{(c_2^{-2})^2 + (c_2^2)^2}\right]\right\},$$

as the refractive power S and C are given by Eq. (A56). Equations (A32) and (A33) are equivalent to Eqs. (A64) and (A67), respectively. Therefore, the boundary change of the low order wavefront propagation is verified. As for the magnitude of the propagated wavefront, a detailed proof is given in Section VIII below.

For the verification of the high order aberrations, it is possible to use Zemax® software (Zemax Development Corporation, Bellevue, Wash.) as a ray tracing tool for the comparison purpose. It is possible to use the free space propagation of a wavefront represented with Zernike polynomials. A Hartmann-Shack wavefront sensor was attached in the Zemax® model, but the calculation of the propagation of the wavefront was not affected by the sensor. For Zernike representation of the wavefronts from the Zemax® model, it is possible to use a 512×512 wavefront sampling to reduce the fitting error. A proper Zernike coefficient conversion can be performed as Zemax® uses the Nolls's notation (Noll, R. J. *J. Opt. Soc. Am.* 66:203-211 (1976)) and the ANSI notation (American National Standard Institute, *Methods for reporting optical aberrations of eyes*, ANSI Z80.28-2004 (Optical Laboratories Association, 2004), Annex B, pp. 1928) was used in embodiments encompassed herein. In some cases, there is a slight difference for the propagation of low order aberrations between the classical vertex correction formula and Zemax®, as can be seen from Table 7.

For high order aberrations, it is possible to use a few single Zernike mode aberrations as shown in Table 8. This shows these examples of aberrations as measured on the exit pupil plane and as represented on a propagated vertex plane. A wavefront diameter of 6 mm is assumed before and after the propagation. Although the wavefront boundary changes after the propagation, the Zernike coefficients are properly scaled (Dai, G.-m. *J. Opt. Soc. Am.* A 23:539-543 (2006)) to the original wavefront radius. The results are compared to those obtained with the analytical expressions developed in the previous section. For each of the single Zernike mode aberrations, both approaches give nearly exact results, except for low orders for the propagation of coma ($Z_3^1$). This discrepancy may be attributed to the approximation of the elliptical pupil to a circular one.

As a further verification, it is possible to use an ocular wavefront from a real eye that consists of all the first 27 Zernike coefficients, as shown in Table 9. The results obtained with the analytical approach and those obtained with Zemax® are again comparable. The differences between the results using the analytical approach and Zemax® are also shown. Also shown are the root mean square (RMS) and high order RMS values. Similar to the previous examples, the wavefront radius before and after propagation is 6 mm. Both approaches give similar results. The reason that the two sets of results are not identical can be attributed to approximations during the theoretical development in the previous section as well as the numerical fitting error in Zemax® software. In particular, for the propagation of coma, the approximation of an elliptical pupil to a circular pupil affects the values of the induced defocus and astigmatism. Without these approximations and numerical error, the results can be expected to be very close, if not identical.

Embodiments encompass verification approaches that involve geometric optics. It can be helpful to verify the wavefront-approach using a ray-tracing (geometric optics) software, such as Zemax®. Before implementing the software, it can be helpful to validate the Zemax® software using the sphere only and sphere and cylinder propagation.

Figure 15:
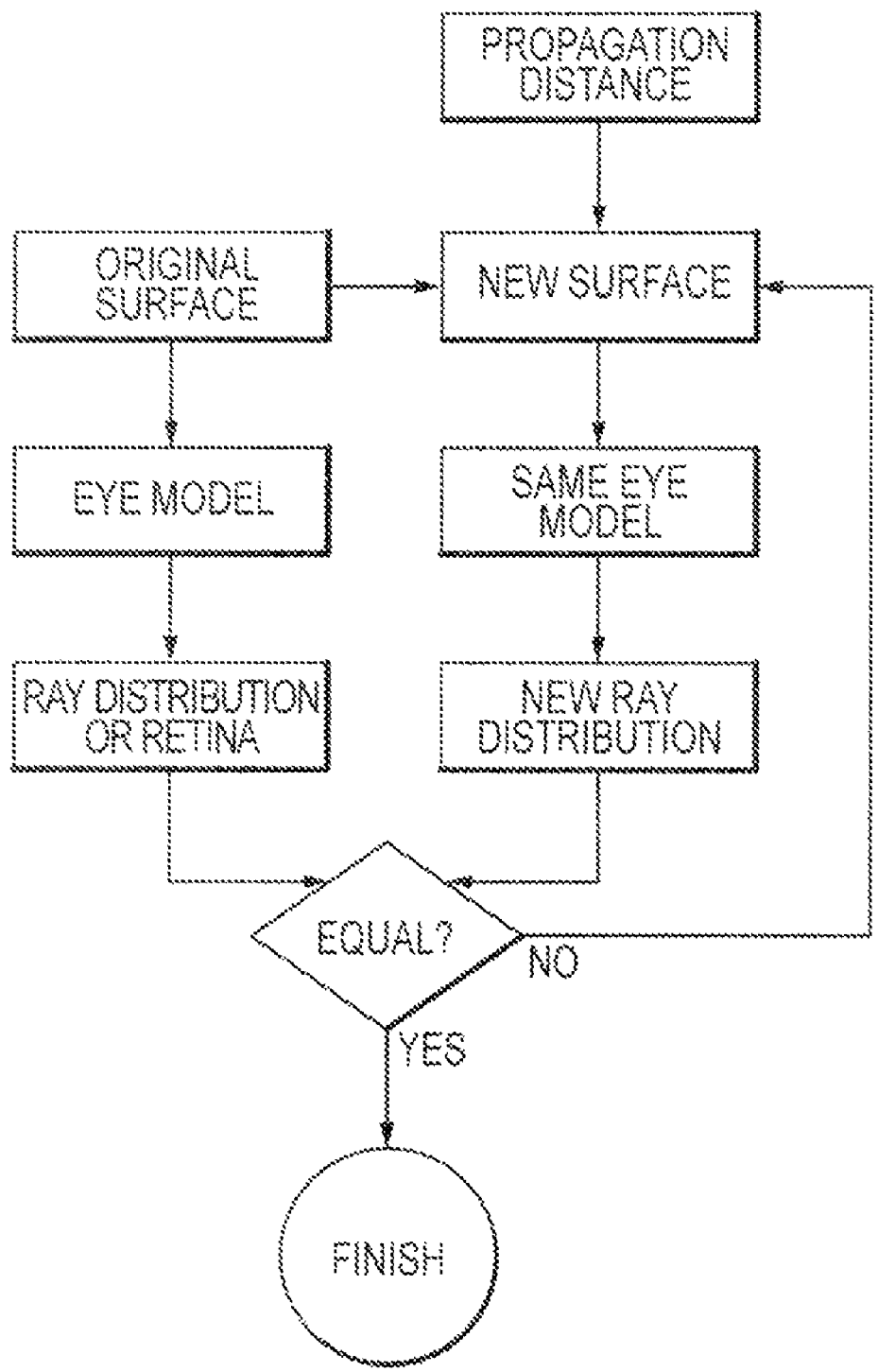
FIG. 15 shows a procedural flow chart for analyzing wavefront propagation according to an embodiment of the present invention.

Some validation embodiments of the present invention involving Zemax® include using a general eye model and creating a surface using Zernike polynomials to include sphere or sphere and cylinder, i.e., Z3, Z4, and Z5. The model can be validated by adjusting a few propagation distances to see if the ray distribution on the imaging plane is the same if the propagated surface, in terms or Zernike polynomials, is optimized. FIG. 15 shows a flow chart of a wavefront propagation using Zemax® modeling for such a process. The result is to compare to that predicted by the classical formula, Eqs. (58) and (59).

Once the first step is validated, the Zemax® model can then be used to validate the techniques described earlier. A random wavefront consisting all of the 27 terms in Zernike polynomials can be used and the result can be compared to those in the analytical subsection.

VII. Discussion

In some embodiments, when a wavefront propagates, it propagates as a whole and cannot be linearly combined, because the direction factor is not a linear function, but a quadratic function, of Zernike polynomials or Taylor monomials. Even so, it is useful to discuss some important aberrations on how they propagate individually.

A. Low Order Aberrations

For a wavefront that consists of low order aberrations only, expressed with Zernike polynomials, the direction factor can be written as $$a = 16\sqrt{3}\, c_2^{-2} c_2^0 Z_2^{-2} + 4\sqrt{3}\, [(c_2^{-2})^2 + 2(c_2^0)^2 + (c_2^2)^2] Z_2^0 + \quad (A34)$$
$$16\sqrt{3}\, c_2^0 c_2^2 Z_2^2 + 12[(c_2^{-2})^2 + 2(c_2^0)^2 + (c_2^2)^2] Z_0^0.$$

After propagation, it does not induce any high order aberrations. The boundary factor can be written as $$b^2 = 24[(c_2^{-2})^2 + 2(c_2^0)^2 + (c_2^2)^2] + 48\sqrt{2}\, c_2^0) \quad (A35)$$
$$\sqrt{(c_2^{-2})^2 + (c_2^2)^2}\, \cos 2(\theta - \phi),$$

where $$\phi = \frac{1}{2}\tan^{-1}\left(\frac{c_2^{-2}}{c_2^2}\right). \quad (A36)$$

Therefore, after propagation, the circular wavefront becomes elliptical, as shown in FIG. 12A.

B. Coma Aberration

For coma aberration, including $Z_3^{-1}$ and $Z_3^1$ Zernike terms, the direction factor after propagation is $$a = 56[(c_3^{-1})^2 + (c_3^1)^2] Z_0^0 + \quad (A37)$$
$$40\sqrt{6}\, c_3^{-1} c_3^1 Z_2^{-2} + 28\sqrt{3}\, [(c_3^{-1})^2 + (c_3^1)^2] Z_2^0 +$$
$$20\sqrt{6}\, [(c_3^1)^2 - (c_3^{-1})^2] Z_2^2 + 72\sqrt{\frac{2}{5}}\, c_3^{-1} c_3^1 Z_4^{-2} +$$

-continued
$$12\sqrt{5}\, (c_3^{-1})^2 + (c_3^1)^2 Z_4^0 + 36\sqrt{\frac{2}{5}}\, [(c_3^1)^2 - (c_3^{-1})^2] Z_4^2).$$

After propagation, coma aberration induces defocus, astigmatism, spherical aberration and secondary astigmatism. The boundary factor can be written as $$b^2 = 200[(c_3^{-1})^2] + (c_3^1)^2 + 192[(c_3^{-1})^2 + (c_3^1)^2]\cos 2(\theta - \phi), \quad (A38)$$

where $$\phi = \frac{1}{2}\tan^{-1}\left[\frac{2c_3^{-1} c_3^1}{(c_3^1)^2 - (c_3^{-1})^2}\right]. \quad (A39)$$

Therefore, propagation of a coma aberration becomes elliptical.

C. Trefoil Aberration

For trefoil aberration, including $Z_3^{-3}$ and $Z_3^3$ Zernike terms, the direction factor after propagation becomes $$a = 24[(c_3^{-3})^2 + (c_3^3)^2] Z_0^0 + \quad (A40)$$
$$12\sqrt{3}\, [(c_3^{-3})^2 + (c_3^3)^2] Z_2^0 + \frac{12}{\sqrt{5}}[(c_3^{-3})^2 + (c_3^3)^2] Z_4^0.$$

Therefore, propagation of trefoil only induces defocus and spherical aberration. The boundary factor b is $$b^2 = 72\, [(c_3^{-3})^2 + (c_3^3)^2]. \quad (A41)$$

So after propagation, the boundary of an original trefoil still is circular.

D. Primary Spherical Aberration

For the primary spherical aberration, $Z_4^0$, the direction factor is $$a = 120(c_4^0)^2 Z_0^0 + 72\sqrt{3}\, (c_4^0)^2 Z_2^0 + 48\sqrt{5}\, (c_4^0)^2 Z_4^0 + \frac{144}{\sqrt{7}}(c_4^0)^2 Z_6^0. \quad (A42)$$

Propagation of primary spherical aberration induces defocus, spherical aberration and secondary spherical aberration. The boundary factor is $$b^2 = 720(c_4^0)^2. \quad A(43)$$

Hence, propagation of spherical aberration still is circular.

E. Secondary Spherical Aberration

For the secondary spherical aberration, $Z_6^0$, the direction factor is $$a = 336(c_6^0)^2 Z_0^0 + 240\sqrt{3}\, (c_6^0)^2 Z_2^0 + 192\sqrt{5}\, (c_6^0)^2 Z_4^0 + \quad (A44)$$
$$128\sqrt{7}\, (c_6^0)^2 Z_6^0)^2 + 240(c_6^0)^2 Z_8^0 + \frac{400}{\sqrt{11}}(c_6^0)^2 Z_{10}^0.$$

Propagation of a secondary spherical aberration induces defocus, spherical aberration, secondary, tertiary, and quaternary spherical aberration. The boundary factor b is $$b^2 = 4032(c_6^0)^2. \quad (A45)$$

So propagation of secondary spherical aberration still is circular.

F. Secondary Astigmatism Aberration

For the secondary astigmatism, $Z_4^{-2}$ and $Z_4^2$, the direction factor is $$a = 100[(c_4^{-2})^2 + (c_4^2)^2 Z_0^0] + 60\sqrt{3}\,[(c_4^{-2})^2 + (c_4^2)^2]Z_2^0 + \quad\quad (A46)$$
$$64\sqrt{10}\,c_4^{-2}c_4^2 Z_4^{-4} + 32\sqrt{5}\,[(c_4^{-2})^2 + (c_4^2)^2]Z_4^0 +$$
$$32\sqrt{10}\,[(c_4^2)^2 - (c_4^{-2})^2]Z_4^4 + 160\sqrt{\frac{2}{7}}\,c_4^{-2}c_4^2 Z_6^{-4} +$$
$$\frac{80}{\sqrt{7}}[(c_4^{-2})^2 + (c_4^2)^2]Z_6^0 + 80\sqrt{\frac{2}{7}}\,[(c_4^2)^2 - (c_4^{-2})^2]Z_6^4).$$

Therefore, the propagation of a secondary astigmatism induces defocus, primary and secondary spherical aberration, quadrafoil and secondary quadrafoil. The boundary factor b is $$b^2 = 520[(c_4^{-2})^2 + (c_4^2)^2] + 480[(c_4^2)^2 + (c_4^2)^2]\cos 4(\theta - \phi), \quad (A47)$$

where $$\phi = \frac{1}{4}\tan^{-1}\left[\frac{2c_4^{-2}c_4^2}{(c_4^2)^2 - (c_4^{-2})^2}\right]. \quad (A48)$$

Therefore, propagation of secondary astigmatism becomes a fourfold symmetry of shape.

G. Secondary Coma Aberration

For a secondary coma, $Z_5^{-1}$ and $Z_5^1$, the direction factor after propagation is $$a = 204[(c_5^{-1})^2 + (c_5^1)^2]Z_0^0 + \quad\quad (A49)$$
$$168\sqrt{6}\,c_5^{-1}c_5^1 Z_2^{-2} + 136\sqrt{3}\,[(c_5^{-1})^2 + (c_5^1)^2]Z_2^0 +$$
$$84\sqrt{6}\,[(c_5^1)^2 - (c_5^{-1})^2]Z_2^2 + \frac{3576}{7}\sqrt{\frac{2}{5}}\,c_5^{-1}c_5^1 Z_4^{-2} +$$
$$\frac{696}{7}\sqrt{5}\,[(c_5^{-1})^2 + (c_5^1)^2]Z_4^0 + \frac{1788}{7}\sqrt{\frac{2}{5}}\,[(c_5^1)^2 - (c_5^{-1})^2]Z_4^2 +$$
$$456\sqrt{\frac{2}{7}}\,c_5^{-1}c_5^1 Z_6^{-2} + \frac{408}{\sqrt{7}}[(c_5^{-1})^2 + (c_5^1)^2]Z_6^0 +$$
$$228\sqrt{\frac{2}{7}}\,[(c_5^1)^2 - (c_5^{-1})^2]Z_6^2 + \frac{600}{7}\sqrt{2}\,c_5^{-1}c_5^1 Z_8^{-2} +$$
$$\frac{520}{7}[(c_5^{-1})^2 + (c_5^1)^2]Z_8^0 + \frac{300}{7}\sqrt{2}\,[(c_5^1)^2 - (c_5^{-1})^2]Z_8^2.$$

Propagation of secondary coma induces defocus, primary, secondary, and tertiary spherical aberrations, primary, secondary, tertiary, and quaternary astigmatism. The boundary factor b is $$b^2 = 1740(c_5^{-1})^2 + (c_5^1)^2 + 1728(c_5^{-1})^2 + (c_5^1)^2 \cos 2(\theta - \phi), \quad (A50)$$

where $$\phi = \frac{1}{4}\tan^{-1}\left[\frac{2c_5^{-1}c_5^1}{(c_5^1)^2 - (c_5^{-1})^2}\right]. \quad (A51)$$

Therefore, propagation of secondary coma becomes elliptical.

H. Quadrafoil Aberration

Finally, for a quadrafoil, $Z_4^{-4}$ and $Z_4^4$, the direction factor is $$a = 40[(c_4^{-4})^2 + (c_4^4)^2]Z_0^0 + 24\sqrt{3}\,[(c_4^{-4})^2 + (c_4^4)^2]Z_2^0 + \quad (A52)$$
$$8\sqrt{5}\,[(c_4^{-4})^2 + (c_4^4)^2]Z_4^0 + \frac{8}{\sqrt{7}}[(c_4^{-4})^2 + (c_4^4)^2]Z_6^0.$$

So the propagation of quadrafoil induces defocus, primary and secondary spherical aberration. The boundary factor b is $$b^2 = 160[(c_4^{-4})^2 + (c_4^4)^2]. \quad (A53)$$

Therefore, propagation of quadrafoil is still circular.

Systems and methods for calculating both the boundary and magnitude of a wavefront after it propagates from one plane to another are provided herein. Taylor monomials can be effectively used to achieve the analytical formulation of the wavefront propagation. Zernike coefficients can be converted to and from Taylor coefficients for wavefront representation before and after the propagation.

Because of the linear nature of the wavefront as expanded into a set of basis functions in some embodiments, the propagation of a wavefront can be treated using the direction factor and the boundary factor, both of which are not linearly proportional to the wavefront. Therefore, in some embodiments the propagated wavefront is not treated as a linear combination of the propagation of individual Zernike polynomials. The propagation of the low order aberrations can be verified by the classical vertex correction formula and the propagation of the high order aberrations can be verified by Zemax® ray tracing software.

The systems and methods disclosed herein are well suited for vision correction as the ocular wavefront is measured on one plane and the correction is performed on another plane. In some embodiments, the analytical nature of the results increases the likelihood of a high precision and in most cases a faster execution.

VIII. Proof of Eq. (A5b) for a Propagated Low Order Wavefront

The low order sphere and cylinder can be expressed in terms of Zernike polynomials as $$W(R\rho, \theta) = \sqrt{6}\,c_2^{-2}\rho^2 \sin 2\theta + \sqrt{3}\,c_2^0(2\rho^2 - 1) + \quad (A54)$$
$$\sqrt{6}\,c_2^2\rho^2\cos 2\theta$$
$$= \sqrt{3}\,c_2^0(2\rho^2 - 1) +$$
$$\sqrt{6}\,\sqrt{(c_2^{-2})^2 + (c_2^2)^2}\,\rho^2\cos 2(\theta - \phi),$$

where the cylinder axis $\phi$ can be expressed as $$\phi = \frac{1}{4}\tan^{-1}\left(\frac{c_2^{-2}}{c_2^2}\right). \quad (A55)$$

Without loss of generality, we use a plus cylinder notation in this section. Therefore, the sphere and cylinder of this wavefront can be derived as $$S = -\frac{4\sqrt{3}\,c_2^0}{R^2} - \frac{\sqrt{6}\,\sqrt{(c_2^{-2})^2+(c_2^2)^2}}{R^2}, \qquad \text{(A56a)}$$

$$C = \frac{4\sqrt{6}\,\sqrt{(c_2^{-2})^2+(c_2^2)^2}}{R^2}. \qquad \text{(A56b)}$$

Writing Eq. (A54) in Cartesian coordinates, we have $$W(u,v) = 2\sqrt{6}\,c_2^{-2}uv + \sqrt{3}\,c_2^0(2u^2+2v^2-1) + \sqrt{6}\,c_2^2(u^2-v^2). \qquad \text{(A57)}$$

Therefore, $$\left[\frac{\partial W(u,v)}{\partial u}\right]^2 + \left[\frac{\partial W(u,v)}{\partial v}\right]^2 = \left(2\sqrt{6}\,c_2^{-2}v + 4\sqrt{3}\,c_2^0 u + 2\sqrt{6}\,c_2^2 u\right)^2 + \qquad \text{(A58)}$$
$$2\sqrt{6}\,c_2^{-2}u + 4\sqrt{3}\,c_2^0 v - 2\sqrt{6}\,c_2^2 v)^2 =$$
$$24[(c_2^{-2})^2 + 2(c_2^0)^2 + (c_2^2)^2]\rho^2 +$$
$$48\sqrt{2}\,c_2^0\sqrt{(c_2^{-2})^2+(c_2^2)^2}\,\rho^2\cos2(\theta-\phi) =$$
$$16\sqrt{3}\,c_2^0 c_2^{-2}Z_2^{-2} + 4\sqrt{3}\,[(c_2^{-2})^2+2(c_2^0)^2+(c_2^2)^2]Z_2^0 +$$
$$16\sqrt{3}\,c_2^0 c_2^2 Z_2^2 + 12[(c_2^{-2})^2+2(c_2^0)^2+(c_2^2)^2]Z_0^0$$

Substituting Eq. (A58) into Eq. (A11), we obtain $$W'(\rho',\theta') = c_2^{-2}Z_2^{-2} + c_2^0 Z_2^0 + c_2^2 Z_2^2 - \frac{d}{2R^2}\{16\sqrt{3}\,c_2^0 c_2^{-2}Z_2^{-2} + \qquad \text{(A59)}$$
$$4\sqrt{3}\,[(c_2^{-2})^2+2(c_2^0)^2+(c_2^2)^2]Z_2^0 +$$
$$16\sqrt{3}\,c_2^0 c_2^2 Z_2^2 + 12[(c_2^{-2})^2+2(c_2^0)^2+(c_2^2)^2]Z_0^0\}$$
$$= b_2^{-2}Z_2^{-2} + b_2^0 Z_2^0 + b_2^2 Z_2^2 + b_0^0 Z_0^0,$$

where $$b_2^{-2} = \left(1 - d\frac{8\sqrt{3}\,c_2^0}{R^2}\right)c_2^{-2} \qquad \text{(A60a)}$$

$$b_2^0 = \left\{1 - d\frac{2\sqrt{3}}{c_2^0 R^2}\left[(c_2^{-2})^2+(c_2^2)^2\right]\right\}c_2^0 \qquad \text{(A60b)}$$

$$b_2^2 = \left(1 - d\frac{8\sqrt{3}\,c_2^0}{R^2}\right)c_2^2 \qquad \text{(A60c)}$$

$$b_0^0 = 12[(c_2^{-2})^2 + 2(c_2^0)^2 + (c_2^2)^2]. \qquad \text{(A60d)}$$

Hence, the sphere and cylinder of the propagated wavefront are $$S' = \frac{4\sqrt{3}\,b_2^0}{R'^2} - \frac{2\sqrt{6}\,\sqrt{(b_2^{-2})^2+(b_2^2)^2}}{R'^2}, \qquad \text{(A61a)}$$

$$C' = \frac{4\sqrt{6}\,\sqrt{(b_2^{-2})^2+(b_2^2)^2}}{R'^2}. \qquad \text{(A61b)}$$

For the new wavefront radius, we can calculate $\tan\psi$ from Eq. (A58)

$$\tan\psi = \frac{2\sqrt{6}}{R}\{[c_2^{-2})^2 + 2(c_2^0)^2 + (c_2^2)^2] + \qquad \text{(A62)}$$

-continued
$$2\sqrt{2}\,c_2^0 + \sqrt{(c_2^{-2})^2+(c_2^2)^2}\,\cos2(\theta-\phi)\}^{1/2}.$$

Apparently, the shape of the wavefront becomes elliptical from the original circular shape after it propagates a distance d. When $\theta=\phi$, the orientation has the minimum power, which corresponds to the sphere power, Eq. (A62) can be written as $$\tan\psi = \frac{1}{R}\left[4\sqrt{3}\,c_2^0 + 2\sqrt{6}\,\sqrt{(c_2^{-2})^2+(c_2^2)^2}\,\right]. \qquad \text{(A63)}$$

Therefore, the semiminor axis of the ellipse is $$R_{min} = R\left\{1 - \frac{d}{R^2}\left[4\sqrt{3}\,c_2^0 + 2\sqrt{6}\,\sqrt{(c_2^{-2})^2+(c_2^2)^2}\,\right]\right\} \qquad \text{(A64)}$$
$$= R(1 + dS).$$

Substituting Eq. (A64) and Eq. (A60) into Eq. (A61a) with some algebra, we obtain $$S = \frac{1}{R_{min}^2}4\sqrt{3}\,b_2^0 + 2\sqrt{6}\,\sqrt{(b_2^{-2})^2+(b_2^2)^2} \qquad \text{(A65)}$$
$$= -\frac{1}{R_{min}^2}\left[4\sqrt{3}\,c_2^0 + 2\sqrt{6}\,\sqrt{(c_2^{-2})^2+(c_2^2)^2}\, - \right.$$
$$\left.\frac{d}{R^2}\left(4\sqrt{3}\,c_2^0 + 2\sqrt{6}\,\sqrt{(c_2^{-2})^2+(c_2^2)}\,\right)^2\right]$$
$$= \frac{1}{R^2(1+dS)^2}[-R^2 S(1+dS)]$$
$$= \frac{S}{1+dS}.$$

When $\theta=\phi$, $+\pi/2$, the orientation has the maximum power, which corresponds to combined power of sphere and cylinder, we have $$\tan\psi = \frac{1}{R}\left[4\sqrt{3}\,c_2^0 - 2\sqrt{6}\,\sqrt{(c_2^{-2})^2+(c_2^2)^2}\,\right]. \qquad \text{(A66)}$$

Therefore, the semimajor axis of the ellipse is $$R_{max} = R\left\{1 - \frac{d}{R^2}\left[4\sqrt{3}\,c_2^0 - 2\sqrt{6}\,\sqrt{(c_2^{-2})^2+(c_2^2)^2}\,\right]\right\} \qquad \text{(A67)}$$
$$= R[1 + d(S+C)].$$

Substituting Eq. (A67) and Eq. (A60) into Eq. (A61) with some algebra, we obtain $$S' + C = -\frac{1}{R_{max}^2}\left[4\sqrt{3}\,b_2^0\right] - 2\sqrt{6}\,\sqrt{(b_2^{-2})^2+(b_2^2)^2} \qquad \text{(A68)}$$
$$= -\frac{1}{R_{max}^2}\left[4\sqrt{3}\,c_2^0\right] - 2\sqrt{6}\,\sqrt{(c_2^{-2})^2+(c_2^2)^2}$$
$$\left. -\frac{d}{R^2}\left(4\sqrt{3}\,c_2^0\right) - 2\sqrt{6}\,\sqrt{(c_2^{-2})^2+(c_2^2)^2}\,\right)^2\right]$$

-continued $$= -\frac{1}{R^2[1+d(S+C)]^2} - [R^2(S+C)[1+d(S+C)]$$

$$= \frac{S+C}{1+d(S+C)}$$

Equations (A65) and (A68) are identical to Eqs. (A5a) and (A5b), respectively, hence proving Eq. (A5b).

IX. Electromagnetic Fields

Embodiments of the present invention also encompass methods and systems for evaluating or characterizing an electromagnetic field that is propagated from a first surface or plane to a second surface or plane. An electromagnetic wave can be represented in a four dimensional space, where one dimensional is the time, and the three other dimensions represent the space. The electric field vector and the magnetic field vector are orthogonal to each other, and both of them are orthogonal to the direction of the propagation of the electromagnetic field. A three-dimensional field that is defined by the electric field vector and the magnetic field vector can be written as $$\Psi(x, y) = A(x, y)\exp\left[-j\frac{2\pi}{\lambda}\Phi(x, y)\right], \quad (A69)$$

where $A(x,y)$ stands for the modulus, or magnitude, $\lambda$ is the wavelength, and $\Phi(x,y)$ is the phase of the electromagnetic field. In the three-dimensional space, if the points where the electromagnetic wave has the same phase are connected, the resulting surface is often referred to as a wavefront. According to some embodiments, if an original plane wave propagates through an isotropic and homogeneous medium, the electromagnetic wave in a new plane that is parallel to the original plane is in-phase, and consequently there is no wavefront error. However, if a plane wave propagates through a lens or other optical or ocular system, the electromagnetic wave in a new plane that is parallel to or corresponds to the original plane is typically no longer in-phase. The difference in terms of the optical path (OPD) in the three-dimensional space can define a wavefront error.

The energy, or the strength, of the electromagnetic wave may change when the wave propagates through a certain medium. Depending upon the properties of the medium, either or both the magnitude $A(x,y)$ and phase $\Phi(x,y)$ may change. For example, in astronomy, both scintillation and phase fluctuation occur when a plane wave passes through the atmospheric turbulence as both $A(x,y)$ and $\Phi(x,y)$ change. For ocular aberrations, $A(x,y)$ in general does not change, or the change can be negligible. Therefore, ocular aberrations are dominated by phase error. For older eyes, $A(x,y)$ may change significantly, as scattering occurs in the crystalline lens.

Thus, embodiments of the present invention can involve the characterization or evaluation of the phase of an electromagnetic field, or in other words a wavefront. Similarly, the magnitude of the electromagnetic field is related to scattering in vision application. In some embodiments, the combination of the magnitude and the phase of the field can be referred to as an electromagnetic strength, or as a strength of an electromagnetic field. The phase aspect of the electromagnetic strength involves what is often referred to as a wavefront.

As noted above, $A(x,y)$ can represent the magnitude of a complex electromagnetic field (or wave). In vision analysis, this term is often ignored or considered to be negligible. That is, $A(x,y)$ is considered as a constant of space and time that does not change as the wave propagates. On the other hand, $\Phi(x,y)$, which is the phase of the complex electromagnetic wave, typically defines the wavefront, and can also be referred to as $W(x,y)$. When a wavefront propagates, or in other words when an electromagnetic field or wave propagates, both $A(x,y)$ and $\Phi(x,y)$ (or $W(x,y)$) can be expected to change. Embodiments of the present invention encompass methods and systems that can evaluate or characterize how $\Phi(x,y)$ or $W(x,y)$ changes with a propagation distance (d).

Because $\Phi(x,y)$ can represent the wavefront aspect of an electromagnetic wave, and can also be referred to as $W(x,y)$, Eq. (A69) can also be written as:

$$\Psi(x, y) = A(x, y)\exp\left[-j\frac{2\pi}{\lambda}W(x, y)\right], \quad (A70)$$

where $A(x,y)$ stands for the modulus, or magnitude, $\lambda$ is the wavelength, and $W(x,y)$ is the phase of the electromagnetic field. The energy, or the strength, of the electromagnetic wave may change when the wave propagates through a certain medium. Depending upon the properties of the medium, either or both the magnitude $A(x,y)$ and phase $W(x,y)$ may change. For example, in astronomy, both scintillation and phase fluctuation occur when a plane wave passes through the atmospheric turbulence as both $A(x,y)$ and $W(x,y)$ change. The wavefront $W(x,y)$ can change as a function of the propagation distance d. In addition, the boundary of $W(x,y)$ can also changes as it propagates. Similarly, the magnitude of the phase $\Phi(x,y)$ or $W(x,y)$ can change as a result of propagation. The magnitude of $\Phi(x,y)$ or $W(x,y)$ can refer to the numerical values of $\Phi(x,y)$ or $W(x,y)$ at each point of a 2-dimensional grid.

$A(x,y)$ can refer to the numerical values of $A(x,y)$ at each point of a 2-dimensional grid. As an illustration of one exemplary embodiment, it is helpful to consider a plane wave which can propagate from the retina towards the pupil of a human eye. If the pupil is sampled with 100×100 discrete points, the electromagnetic field at each point is a complex number, the modulus $A(i,j)$ with the phase $W(i,j)$, where i and j stand for the indices in this 2-D matrix. If there are no ocular aberrations, the values A and W would be constant. If there are ocular aberrations but no scattering, then A can still remain constant but W can be different for different pairs of (i,j). For example, $W(i,j)$ can change as follows. First, the magnitude (numerical values) can change as the propagation distance d changes. Second, the boundary can change, or in other words the original 2-dimensional grid can change. The boundary change can be somewhat like a distortion.

Thus, embodiments of the present invention which encompass methods and systems for evaluating or characterizing an electromagnetic field that is propagated from a first surface or plane to a second surface or plane can involve determining a first surface characterization of the electromagnetic field corresponding to the first surface. The first surface characterization can include a first surface field strength. These techniques can also involve determining a propagation distance between the first surface and a second surface, and determining a second surface characterization of the electromagnetic field based on the first surface characterization and the propagation distance, where the second surface characterization includes a second surface field strength. In some cases, the first surface field strength includes a first surface field phase, and the second surface field strength includes a second surface field phase.

Each of the calculations or operations disclosed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patent filings, scientific journals, books, treatises, and other publications and materials discussed in this application are hereby incorporated by reference for all purposes. Although embodiments of the invention have often been described herein with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with embodiments of the current invention. The above systems are available from TRACEY Technologies of Bellaire, Tex., Wavelight of Erlangen, Germany, and Nidek, Inc. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method of generating a refractive treatment shape for ameliorating a vision condition in an eye of a patient, the method comprising:
   determining a first wavefront measurement corresponding to the pupil plane of the eye, the first wavefront measurement comprising a first wavefront boundary and a first set of wavefront coefficients;
   determining a propagation distance between the pupil plane of the eye and a treatment surface;
   determining a propagated wavefront measurement corresponding to the treatment surface based on the first wavefront measurement and the propagation distance, the propagated wavefront measurement comprising a second wavefront boundary and a second set of wavefront coefficients; and
   generating the refractive treatment shape based on the propagated wavefront measurement,
   wherein the refractive treatment shape is configured to ameliorate a high order aberration of the first wavefront measurement which comprises the first set of wavefront coefficients; and
   wherein a difference between the first set of wavefront coefficients and the second set of wavefront coefficients is proportional to a value selected from the group consisting of the propagation distance, a direction factor, an inverse of a dimension of the first wavefront boundary, and an inverse of a squared radius of the first wavefront boundary.

2. The method of claim 1, wherein the treatment surface corresponds to a member selected from the group consisting of a corneal surface, a spectacle lens surface, a scleral lens surface, a contact lens surface, and an intraocular lens surface.

3. The method of claim 1, further comprising applying the refractive treatment shape to the eye of the patient to ameliorate the vision condition.

4. The method of claim 3, wherein the refractive treatment shape is applied to the eye of the patient in a treatment modality selected from the group consisting of:
   ablating a corneal surface of the eye to provide a corneal surface shape that corresponds to the refractive treatment shape;
   providing the patient with a contact lens that has a shape that corresponds to the refractive treatment shape;
   providing the patient with a spectacle lens that has a shape that corresponds to the refractive treatment shape;
   providing the patient with a scleral lens that has a shape that corresponds to the refractive treatment shape; and
   providing the patient with an intraocular lens that has a shape that corresponds to the refractive treatment shape.

5. The method of claim 3, wherein the treatment surface corresponds to a member selected from the group consisting of a corneal surface, a spectacle lens surface, a scleral lens surface, a contact lens surface, and an intraocular lens surface, and wherein the refractive treatment shape is applied to the eye of the patient in a treatment modality selected from the group consisting of:
   ablating a corneal surface of the eye to provide a corneal surface shape that corresponds to the refractive treatment shape;
   providing the patient with a contact lens that has a shape that corresponds to the refractive treatment shape;
   providing the patient with a spectacle lens that has a shape that corresponds to the refractive treatment shape;
   providing the patient with a scleral lens that has a shape that corresponds to the refractive treatment shape; and
   providing the patient with an intraocular lens that has a shape that corresponds to the refractive treatment shape.

6. A method of generating a refractive treatment shape for ameliorating a vision condition in an eye of a patient, the method comprising:
   determining a first wavefront measurement corresponding to the pupil plane of the eye, the first wavefront measurement comprising a first wavefront boundary and a first set of wavefront coefficients;
   determining a propagation distance between the pupil plane of the eye and a treatment surface;
   determining a propagated wavefront measurement corresponding to the treatment surface based on the first wavefront measurement and the propagation distance, the propagated wavefront measurement comprising a second wavefront boundary and a second set of wavefront coefficients; and generating the refractive treatment shape based on the propagated wavefront measurement, wherein the refractive treatment shape is configured to ameliorate a high order aberration of the propagated wavefront measurement; and wherein a difference between the first set of wavefront coefficients and the second set of wavefront coefficients is proportional to a value selected from the group consisting of the propagation distance, a direction factor, an inverse of a dimension of the first wavefront boundary, and an inverse of a squared radius of the first wavefront boundary.

7. The method of claim 6, wherein the treatment surface corresponds to a member selected from the group consisting of a corneal surface, a spectacle lens surface, a scleral lens surface, a contact lens surface, and an intraocular lens surface.

* * * * *